(12) United States Patent
Butlin et al.

(10) Patent No.: US 8,507,199 B2
(45) Date of Patent: Aug. 13, 2013

(54) MULTI-COLOR TIME RESOLVED FLUOROPHORES BASED ON MACROCYCLIC LANTHANIDE COMPLEXES

(75) Inventors: Nathaniel G. Butlin, Pacifica, CA (US); Todd M. Corneillie, Campbell, CA (US); Jide Xu, Berkeley, CA (US)

(73) Assignee: Lumiphore, Inc., Berkeley, CA (US)

( * ) Notice: Subject to any disclaimer, the term of this patent is extended or adjusted under 35 U.S.C. 154(b) by 728 days.

(21) Appl. No.: 12/521,910

(22) PCT Filed: Jan. 25, 2008

(86) PCT No.: PCT/US2008/052116
§ 371 (c)(1),
(2), (4) Date: Mar. 15, 2010

(87) PCT Pub. No.: WO2008/092120
PCT Pub. Date: Jul. 31, 2008

(65) Prior Publication Data
US 2010/0167289 A1   Jul. 1, 2010

Related U.S. Application Data

(60) Provisional application No. 60/886,530, filed on Jan. 25, 2007, provisional application No. 60/982,670, filed on Oct. 25, 2007.

(51) Int. Cl.
*C12Q 1/68*   (2006.01)
*C07D 259/00*  (2006.01)

(52) U.S. Cl.
USPC ............................................................ 435/6.1

(58) Field of Classification Search
USPC ................... 435/6.1; 536/22.1; 540/452, 460
See application file for complete search history.

(56) References Cited

U.S. PATENT DOCUMENTS

| | | | |
|---|---|---|---|
| 4,855,225 A | 8/1989 | Fung et al. | |
| 5,047,519 A | 9/1991 | Hobbs, Jr. et al. | |
| 5,049,280 A | 9/1991 | Raymond et al. | |
| 5,252,462 A | 10/1993 | Drevin et al. | |
| 5,435,990 A | 7/1995 | Cheng et al. | |
| 5,470,896 A | 11/1995 | Wegmann et al. | |
| 5,820,849 A | 10/1998 | Schmitt-Willich et al. | |
| 5,989,823 A | 11/1999 | Jayasena et al. | |
| 6,406,297 B1 | 6/2002 | Raymond et al. | |
| 6,515,113 B2 | 2/2003 | Raymond et al. | |
| 6,864,103 B2 | 3/2005 | Raymond et al. | |
| 7,018,850 B2 | 3/2006 | Raymond et al. | |
| 7,442,558 B2 | 10/2008 | Raymond et al. | |
| 8,173,800 B2 * | 5/2012 | Raymond et al. | 540/145 |
| 2002/0128451 A1 | 9/2002 | Raymond et al. | |
| 2002/0188111 A1 | 12/2002 | Raymond et al. | |
| 2003/0199688 A1 | 10/2003 | Kriesel et al. | |
| 2005/0058604 A1 | 3/2005 | Raymond et al. | |
| 2007/0134160 A1 | 6/2007 | Leif et al. | |
| 2008/0213780 A1 | 9/2008 | Butlin et al. | |
| 2008/0213917 A1 | 9/2008 | Raymond et al. | |
| 2009/0023928 A1 | 1/2009 | Raymond et al. | |
| 2009/0036537 A1 | 2/2009 | Raymond et al. | |
| 2010/0151591 A1 | 6/2010 | Butlin et al. | |
| 2010/0167289 A1 | 7/2010 | Butlin et al. | |

FOREIGN PATENT DOCUMENTS

| | | |
|---|---|---|
| CA | 2099542 | 7/1993 |
| EP | 0578067 | 6/1993 |
| WO | WO 92/11039 | 7/1992 |
| WO | WO 97/45539 | 4/1997 |
| WO | WO 00/48990 | 8/2000 |
| WO | WO 2005/030711 | 4/2005 |
| WO | WO 2008/063721 A2 | 5/2008 |
| WO | WO 2008-092120 A1 | 7/2008 |

OTHER PUBLICATIONS

Petoud, et al., Stable Lanthanide Luminescence Agents Highly Emissive in Aqueous Solution: Multidentate 2-Hydroxyisophthalamide Complexes of $Sm^{3+}$, $EU^{3+}$, $Tb^{3+}$, $Dy^{3+}$, *J. Am. Chem. Soc.*, 2003, 125:13324-13325.

Johansson et al., *J. Am. Chem. Soc.*, 2004, 126(50):16451-16455.

Chen, et al., *J. Am. Chem. Soc.*, 122:657-660 (2000).

Arnaud, et al., "Synthesis of macrocyclic tetralactams from L-tartaric acid and *beta*-hydroxyglutaric acid," *Tetrahedron*, 53(40):13757-13768, XP002537292 (1997).

Blomberg, et al., "Terbium and rhodamine as labels in a homogeneous time resolved fluorometric energy transfer assay of the β subunit of human chorionic gonadotropin in serum", *Clinical Cehmistry*, 45(6):855-861 (1999).

Brooker, S. et al., Chemical Abstract 2002: 593344 (2002).

Bünzli, et al., "Towards materials with planned properties : dinuclear f-f helicates and d-f non-convalent podates based on benzimidazole-pyridine binding units", *Journal of Alloys and Compounds*, 249:14-24 (1997).

Cardullo, R. et al., "Detection of nucleic acid hybridization by nonradiative fluorescence resonance energy transfer", *Proc. Natl. Acad. Sci. USA* 85:8790-8794 (1988).

Cohen, et al., "A Novel Salicylate-Based Macrobicycle with a "Split Personality"", *Inorg. Chem.*, 38(20):4522-4529, XP002537288 (Sep. 15, 1999).

(Continued)

*Primary Examiner* — Joseph Kosack
(74) *Attorney, Agent, or Firm* — Morgan, Lewis & Bockius LLP; Jeffry S. Mann

(57) ABSTRACT

The present invention provides a novel class of macrocyclic compounds as well as complexes formed between a metal (e.g., lanthanide) ion and the compounds of the invention. Preferred complexes exhibit high stability as well as high quantum yields of lanthanide ion luminescence in aqueous media without the need for secondary activating agents. Preferred compounds incorporate hydroxy-isophthalamide moieties within their macrocyclic structure and are characterized by surprisingly low, non-specific binding to a variety of polypeptides such as antibodies and proteins as well as high kinetic stability. These characteristics distinguish them from known, open-structured ligands.

25 Claims, 20 Drawing Sheets

(56) References Cited

OTHER PUBLICATIONS

Dahlén "Detection of Biotinylated DNA Probes by Using Eu-Labeled Streptavidin and Time-Resolved Fluorometry" *Anal. Biochem.*, 164:78-83 (1987).
De Sá, et al., "Spectroscopic properties and design of highly luminescent lanthanide coordination complexes", *Coordination Chemistry Reviews*, 196:165-195 (2000).
Dexter, D.L., "A Theory of Sensitized Luminescence in Solids", *Journal of Chemical Physics* 21: 836-850 (1953).
Dickins, et al., "Synthesis, time-resolved luminescence, NMR spectroscopy, circular dichroism and circularly polarised luminescence studies f enantiopure macrocyclic lanthanide tetraamide complexes", *Chem. Eur. J.*, 5(3):1095-1105 (1999).
Dickson, et al., "Time-resolved detection of lanthanide luminescence of ultrasensitive bioanalytical assays", *Journal of Photochemistry and Photobiology, B: Biology*, 27:3-19 (1995).
Galaup, et al., "Mono(di)nuclear eropium(III) complexes of macrobi(tri)cyclic cryptands derived from diazatetralactams as luminophores in aqueous solution", *Helvetica Chimica Acta*, 82:543-560 (1999).
Gong, B., "Crescent oligoamides: From acyclic "Macrocycles" to folding nanotubes," *Chem. Eur. J.*, 7(20):4336-4342, XP002537290 (2001).
Heid, C. et al., "Real time quantitative PCR", *Genome Res.* 6:986-994 (1996).
Hemmilä, et al., "Development of luminescent lanthanide chelate labels for diagnostic assays", *Journal of Alloys and Compounds*, 249:158-162 (1997).
Higuchi, R. et al., "Simultaneous Amplification and Detection of Specific DNA Sequences", *Bio/Technology* 10:413-417 (1992).
Hochstrasser, R. et al., "Distance distribution in a dye-linked oligonucleotide dtermined by time-resolved fluorescence energy transfer", *Biophysical Chemistry* 45:133-141 (1992).
Holland, P. et al., "Detection of specific polymerase chain reaction product by utilizing the 5'→3' exonuclease activity of *Thermus aquaticus* DNA polymerase", *Proc. Nat. Acad. Sci. USA*, 88:7276-7280 (1991).
Jagannathan, R. et al. "Complexes of lanthanide perchlorated with N,N,N'n'-tetra amethyl-α-carboxamido-o-anisamide and N, N'-di-t-butyl-α-carboxamido-o-anisamide" Inorganica Chimica Acta, 1979, vol. 37, No. 1 L449-L451.
Knight, C.G., "Fluorimetric Assays of Proteolytic Enzymes", *Methods in Enzymology* 248: 18-34 (1995).
Kostrikis, L. et al., "Spectral Genotyping of Human Alleles", *Science* 279:1228-1229 (1998).
Lee, L. et al., "Allelic discrimination by nick-translation PCR with fluorogenic probes", *Nucleic Acids Res.* 21:3761-3766 (1993).
Lee, L. G. et al., "Seven-Color, Homogeneous Detection of Six PCR Products" *BioTechniques* 27:342-349 (1999).
Li, et al., "Shape-persistent aromatic amide oligomers: New tools for supramolecular chemistry," *Chem. Asian J.*, 1:766-778, XP002537289 (2006).
Nazarenko, I.A. et al., "A closed tube format for amplification and detection of DNA based on energy transfer", *Nucleic Acids Res.* 25:2516-2521 (1997).
Okawa, et al., "Binuclear metal complexes. V. Template synthesis of a binuclear copper(II) complex of a macrocycle containing amido groups," *Chem. Lett..*, pp. 1027-1030, XP009120043 (1972).
Ost, H., *Journal Prakt. Chem.* 2:110-111 (1876).
Sabbatini, et al., "Luminescent lanthanide complexes as photochemical supramolecular devices", *Coordination Chemistry Reviews*, 123:201-228 (1993).
Saha, et al., "Time-resolved fluorescence of a new europium chelate complex: Demonstration of highly sensitive detection of protein and DNA samples", *J. Am. Chem. Soc.*, 115:11032-11033 (1993).
Selvin, P., "Fluorescence Resonance Energy Transfer", *Methods in Enzymology* 246:300-334 (1995).
Soini, et al., "Time-resolved fluorescence of lanthanide probes and applications in biotechnology", *CRC Critical Reviews in Analytical Chemistry*, 18(2):105-154 (1987).
Steemers, et al., "Water-soluble neutral calix[4]arene-lanthanide complexes: Synthesis and luminescence properties", *J. Org. Chem.*, 62:4229-4235 (1997).
Steinberg, I., "Long-Range Nonradiative Transfer of Electronic Excitation Energy in Proteins and Polypeptides", *Ann. Rev. Biochem.* 40:83-114 (1971).
Stenroos, et al., "Homogeneous time-resolved IL-21L-Rα assay using fluorescence resonance energy transfere", *Cytokine* 10(7):495-499 (Jul. 1998).
Stryer, L., "Fluorescence Energy Transfer as a Spectroscopic Ruler", *Ann. Rev. Biochem.* 47:819-846 (1978).
Syvänen et al., "Time-resolved fluorometry: a sensitive method to quantify DNA-hybrids" *Nucleic Acids Research*, 14:1017-1028 (1986).
Tyagi, S. et al., "Molecular Beacons: Probes that Fluoresce upon Hybridization", *Nature Biotechnology* 14: 303-308 (1996).
Tyagi, S. et al., "Multicolor molecular beacons for allele discrimination", *Nature Biotechnology* 16:49-53 (1998).
Veiopoulou, et al., "Comparative study of fluorescent ternary terbium complexes. Application in enzyme amplified fluorimetric immunoassay for α-fetoprotein", *Analytica Chimica Acta*, 335:177-184 (1996).
Vicentini, et al., "Luminescence and structure of europium compounds", *Coordination Chemistry Reviews*, 196:353-382 (2000).
Voss, H. et al., "Direct genomic fluorescent on-line sequencing and analysis using in vivo amplification of DNA", *Nucleic Acids Research* 17:2517 (1989).
Wang, G. et al., "Design and Synthesis of New Fluorogenic HIV Protease Substrates Based on Resonance Energy Transfer", *Tetrahedron Letters* 31: 6493-6496 (1990).
Wang, Y. et al., "Rapid Sizing of Short Tandem Repeat Alleles Using Capillary Array Electrophoresis and Energy-Transfer Fluorescent Primers", *Anal. Chem.* 67:1197-1203 (1995).
Whitcombe, D. et al., "Detection of PCR products using self-probing amplicons and fluorescence", *Nature Biotechnology* 17:804-807 (1999).

* cited by examiner

FIGURE 13

| Acceptor | Absorbance (nm) | Emission (nm) |
|---|---|---|
| Fluorescein (FITC) | 494 | 518 |
| Eosin | 524 | |
| TRITC | 543 | |
| Rhodamine 101 | 496 | 520 |
| Rhodamine Red | 570 | |
| Texas Red | 595 | 615 |
| Alexa 488 | 495 | 519 |
| Alexa 532 | 530 | |
| Alexa 546 | 555 | 573 |
| Cy2 | 489 | 506 |
| Cy3 | 548 | 562 |
| Cy5 | 649 | 670 |
| Malachite Green | 630 | |
| TAMRA | 555 | 580 |
| Acridine orange | 500 | 530 |
| Bodipy 530/550 | 534 | 554 |
| BODIPY TR-X | 588 | 616 |
| GFP | 489 | 509 |
| Nile Red | 485 | 525 |
| Oregon Green 488 | 493 | 520 |
| YOYO-1 | 491 | 509 |
| YOYO-2 | 612 | 631 |
| Ca-Green | 506 | 534 |
| Ca-Orange | 555 | 576 |
| Ca-Crimson | 588 | 610 |
| Mg-Green | 506 | 532 |
| Na-Green | 507 | 532 |

MULTI-COLOR TIME RESOLVED FLUOROPHORES BASED ON MACROCYCLIC LANTHANIDE COMPLEXES

CROSS-REFERENCE TO RELATED APPLICATIONS

This application is a U.S. national phase of PCT Patent Application No. PCT/US2008/052116, filed Jan. 25, 2008 and claims priority under 35 U.S.C. §119(e) to U.S. Provisional Patent Application No. 60/886,530, filed on Jan. 25, 2007 and U.S. Provisional Patent Application No. 60/982,670, filed on Oct. 25, 2007, the disclosures of which are incorporated by reference herein in their entirety for all purposes.

FIELD OF THE INVENTION

This invention relates to compound fluorophores that have tunable emission wavelengths and tunable excited-state lifetimes. Exemplary fluorophores of the invention include macrocyclic ligands and lanthanide complexes thereof bound to an organic fluorophore through a linker moiety.

BACKGROUND OF THE INVENTION

There is a continuous and expanding need for rapid, highly specific methods of detecting and quantifying chemical, biochemical and biological substances as analytes in research and diagnostic mixtures. Of particular value are methods for measuring small quantities of nucleic acids, peptides, pharmaceuticals, metabolites, microorganisms and other materials of diagnostic value. Examples of such materials include small molecular bioactive materials (e.g., narcotics and poisons, drugs administered for therapeutic purposes, hormones), pathogenic microorganisms and viruses, antibodies, and enzymes and nucleic acids, particularly those implicated in disease states.

The presence of a particular analyte can often be determined by binding methods that exploit the high degree of specificity, which characterizes many biochemical and biological systems. Frequently used methods are based on, for example, antigen-antibody systems, nucleic acid hybridization techniques, and protein-ligand systems. In these methods, the existence of a complex of diagnostic value is typically indicated by the presence or absence of an observable "label" which is attached to one or more of the interacting materials. The specific labeling method chosen often dictates the usefulness and versatility of a particular system for detecting an analyte of interest. Preferred labels are inexpensive, safe, and capable of being attached efficiently to a wide variety of chemical, biochemical, and biological materials without significantly altering the important binding characteristics of those materials.

A wide variety of labels are known, each with particular advantages and disadvantages. For example, radioactive labels are quite versatile, and can be detected at very low concentrations. Such labels are, however, expensive, hazardous, and their use requires sophisticated equipment and trained personnel. Thus, there is wide interest in non-radioactive labels, particularly labels observable by spectrophotometric, spin resonance, and luminescence techniques, and reactive materials, such as enzymes that produce such molecules.

Labels that are detectable using fluorescence spectroscopy are of particular interest, because of the large number of such labels that are known in the art. Moreover, the literature is replete with syntheses of fluorescent labels that are derivatized to allow their facile attachment to other molecules, and many such fluorescent labels are commercially available.

In addition to being directly detected, many fluorescent labels operate to quench the fluorescence of an adjacent second fluorescent label. Because of its dependence on the distance and the magnitude of the interaction between the quencher and the fluorophore, the quenching of a fluorescent species provides a sensitive probe of molecular conformation and binding, or other, interactions. An excellent example of the use of fluorescent reporter quencher pairs is found in the detection and analysis of nucleic acids.

Conventional organic fluorophores generally have short fluorescence lifetimes, on the order of nanoseconds (ns) which is generally too short for optimal discrimination from background fluorescence. An alternative detection scheme, which is theoretically more sensitive than conventional fluorescence, is time-resolved fluorimetry. According to this method, a chelated lanthanide metal with a long radiative lifetime is attached to a molecule of interest. Pulsed excitation combined with a gated detection system allows for effective discrimination against short-lived background emission. For example, using this approach, the detection and quantification of DNA hybrids via an europium-labeled antibody has been demonstrated (Syvanen et al., *Nucleic Acids Research* 14: 1017 1028 (1986)). In addition, biotinylated DNA was measured in microtiter wells using Eu-labeled strepavidin (Dahlen, *Anal. Biochem.* (1982), 164: 78 83). A disadvantage, however, of these types of assays is that the label must be washed from the probe and its fluorescence developed in an enhancement solution.

Lanthanide chelates, particularly coordinatively saturated chelates that exhibit excellent fluorescence properties are highly desirable. Alternatively, coordinatively unsaturated lanthanide chelates exhibiting acceptable fluorescence in the presence of water are also advantageous. Such chelates that are derivatized to allow their conjugation to one or more components of an assay, find use in a range of different assay formats. The present invention provides these and other such compounds and assays using these compounds. Hydroxyisophthalamide (IAM) complexes of lanthanide ions such as $Tb^{3+}$ are potentially useful in a variety of biological applications. Of particular importance for biological applications is that these complexes exhibit kinetic stability at high dilution in aqueous solutions, i.e., concentrations at or below nM levels.

Hydroxyisophthalamide ligands useful in applications requiring luminescence have been described (Petoud et al., *J. Am. Chem. Soc.* 2003, 125, 13324-13325; U.S. Pat. No. 7,018,850 to Raymond et al.), and Johansson et al., *J. Am. Chem. Soc.* 2004, 126(50):16451-16455).

However, a need for luminescent complexes, which are stable under biological relevant conditions and at low concentrations, and which simultaneously exhibit low non-specific interactions with proteins, remains. Moreover, multiplex assays in which more than one fluorophore undergoes excitation and detection are of use in many fields. Thus, there is a continuing need for fluorescent systems amenable to incorporation in such mulitplex assays. The current invention addresses these and other needs.

SUMMARY OF THE INVENTION

The invention provides a new class of macrocyclic ligands and metal complexes of these ligands. Also provided are conjugates of these ligands with carrier moieties, which are of use in single fluorophore and multiplex applications. The invention also provides mixtures of carrier moieties, each conjugated to a chelate of the invention. Moreover, there are provided mixtures of carrier moieties in which one or more of a first carrier moiety species is conjugated to a chelate of the invention and one or more of a second carrier moiety species is conjugated to a fluorophore different in structure from the chelate attached to the first carrier moiety species. The invention also provides single fluorophore and multiplex assays incorporating one or more chelate of the invention. It is generally preferred that the chelates be bound to a metal ion, which, together with the chelate, forms a luminescent metal ion complex.

In particular, the invention provides luminescent complexes, e.g., lanthanide (e.g., terbium and europium) complexes and conjugates of these complexes with a carrier moiety. These complexes exhibit high stability and solubility in aqueous media as well as high quantum yields of luminescence in water without external augmentation (e.g., by micelles or fluoride). The complexes are formed between a metal ion, e.g., of the lanthanide series and a new class of macrocyclic ligands provided by the invention. Preferred ligands incorporate a hydroxy-containing aromatic building block, such as a 2-hydroxy-1,3-amine or -amide (e.g., hydroxy-isophthalamide) moieties within their structure and are characterized by surprisingly low non-specific binding to a variety of different polypeptides such as antibodies and proteins. Due to their unique chemical and physicochemical properties the complexes of the present invention find use in any application requiring luminescence, particularly in aqueous media, including medical diagnostics and bioanalyical assay systems.

In a first embodiment, the invention provides a compound that includes a chelate structure according to Formula I:

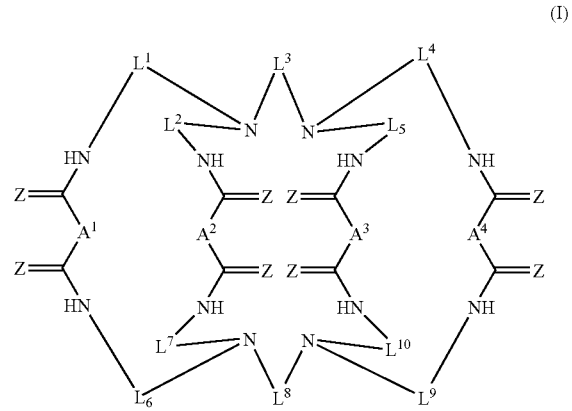

(I)

wherein the compound preferably includes at least one acceptor-linker, which is optionally covalently bound to a fluorophore, e.g., through a linkage fragment. In another embodiment, the compound of the invention includes at least one functional moiety. In a still further embodiment, a reactive functional group on the functional moiety is converted to a linkage fragment by reaction with a complementary reactive group on a carrier moiety, e.g., a nucleic acid, a peptide, an antibody, a saccharide, lectin, receptor or antigen, or a solid support.

In Formula I, each Z is a member independently selected from O and S. $L^1$, $L^2$, $L^3$, $L^4$, $L^5$, $L^6$, $L^7$, $L^8$, $L^9$ and $L^{10}$ ("$L^x$" moieties) are linker groups independently selected from substituted or unsubstituted alkyl, substituted or unsubstituted heteroalkyl, substituted or unsubstituted aryl, substituted or unsubstituted heteroaryl and substituted or unsubstituted heterocycloalkyl.

$A^1$, $A^2$, $A^3$ and $A^4$ are members independently selected from substituted or unsubstituted aryl and substituted and unsubstituted heteroaryl (e.g., an azulene group) moieties. In an exemplary embodiment, these moieties are independently selected from the following structure:

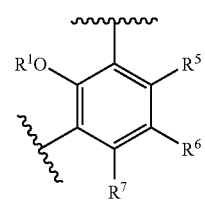

wherein each $R^1$ is a member independently selected from H, an enzymatically labile group, a hydrolytically labile group, a metabolically labile group and a single negative charge. Each $R^5$, $R^6$ and $R^7$ is a member independently selected from H, substituted or unsubstituted alkyl, substituted or unsubstituted heteroalkyl, halogen, CN, $CF_3$, acyl, —$SO_2NR^{17}R^{18}$, —$NR^{17}R^{18}$, —$OR^{17}$, —$S(O)_2R^{17}$, —$C(O)R^{18}$, —$COOR^{17}$, —$CONR^{17}R^{18}$, —$S(O)_2OR^{17}$, —$OC(O)R^{17}$, —$C(O)NR^{17}R^{18}$, —$NR^{17}C(O)R^{18}$, —$NR^{17}SO_2R^{18}$, and —$NO_2$, wherein $R^6$ and a member selected from $R^5$, $R^7$ and combinations thereof are optionally joined to form a ring system which is a member selected from substituted or unsubstituted cycloalkyl, substituted or unsubstituted heterocycloalkyl, substituted or unsubstituted aryl and substituted or unsubstituted heteroaryl.

$R^{17}$ and $R^{18}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and $R^{17}$ and $R^{18}$, together with the atoms to which they are attached, are optionally joined to form a 5- to 7-membered ring.

In an exemplary embodiment, a compound according to Formula I is covalently attached through the functional moiety to a carrier molecule.

Exemplary compounds according to any of the embodiments discussed above, are those in which at least one $L^x$ moiety is functionalized with a acceptor-linker, optionally bound to a fluorophore, e.g., through a linkage fragment. In another embodiment, at least one of $L^x$ moiety is functionalized with a functional moiety (optionally bound to a carrier moiety or solid support, e.g., through a linkage fragment). In yet another exemplary embodiment, one of these $L^x$ groups is functionalized with a acceptor-linker (optionally bound to a fluorophore) and the same or a different $L^x$ moiety is functionalized with a functional moiety (optionally bound to a carrier moiety or solid support). As will be appreciated by those of skill in the art, a fluorophore coupled to a acceptor-linker can be an organic fluorophore or a macrocyclic chelate, e.g., such as the structure set forth in Formula I. Moreover, a branched fluorophore with more than one reactive functional group can be use to couple more than one fluorophore through the reactive functional groups, whether the fluorophore is a wholly organic species or is a metal chelate.

In a second aspect, the invention provides a luminescent complex formed between at least one metal ion and a chelate according to Formula I. In contrast to organic fluorophores that have a fluorescence lifetime of about 10 ns, lanthanide chelates of the invention preferably have emission lifetimes greater than 100 microseconds, preferably at least 500 microseconds and even more preferably at least 1 ms. The mechanism that is responsible for the long lifetime emission of lanthanide chelates involves energy transfer from the triplet state of the aromatic ligand. Specifically, upon excitation the ligand is excited to its singlet state and then undergoes an intersystem transition to its triplet state, transferring the energy to the lanthanide ion. Fluorescence is then emitted from the lanthanide ion as it returns to the ground state. Since such fluorescence emission does not result from a singlet-to-singlet transition, the use of lanthanide chelates as a donor results in luminescent resonance energy transfer (LRET). Therefore, by using pulse excitation and time-gating techniques, emission from the fluorophore can be selectively recorded after the background fluorescence from organic dyes, scattering, and autofluorescence has decayed. The only signals remaining in this long-time domain are the emission from the lanthanide chelate and from acceptor fluorophores that have participated in LRET. In this case the narrow emission peaks of a lanthanide chelate render the background fluorescence close to zero at certain wavelengths, leading to extremely large signal-to-background ratio.

In another aspect, the invention provides a compound according to Formula I in a mixture with an analyte. Exemplary analytes include nucleic acids, peptides, antibodies, antigens, lectins, saccharides, cells and receptors.

In a fourth aspect, the invention provides a method of detecting the presence or absence of an analyte in a sample. The method comprises (a) combining the sample and a composition including a luminescent complex of the invention; (b) exciting the complex; and (c) detecting luminescence (e.g., fluorescence) from the complex. In one example, the presence or absence of the analyte is indicated by the presence or absence of luminescence from the complex. In an exemplary embodiment, the excited complex transfers energy to a fluorophore other than the complex and luminescence from the excited fluorophore is detected and indicates the presence or absence of an analyte in the sample. The analyte can be quantitated by quantitating the luminescence from the complex or the fluorophore. The fluorophore can also serve as a quencher or other luminescence modifying group, alternatively, the acceptor-linker can be conjugated to a non-fluorescent quencher or other luminescence modifying moeity that forms an energy transfer pair with a luminescent complex of the invention.

In a fifth aspect, the invention provides a method of detecting the presence or absence of an analyte in a sample. The method includes (a) combining the sample and a composition including a luminescent complex of the invention, and a luminescence modifying group, wherein energy can be transferred between the complex and the luminescence modifying group when the complex is excited, and wherein the complex and the luminescence modifying group can be part of the same molecule or part of different molecules; and (b) exciting the complex; and (c) determining a luminescent property of the sample, wherein the presence or absence of the analyte is indicated by the luminescent property of the sample. In one example, the presence or absence of the analyte in the sample is indicated by a change in the luminescent property of the sample (e.g., change in lifetime, change in emission wavelength, change in amount of luminescence). The amount of analyte in the sample can be quantitated by quantitating the luminescent property or the change in the luminescent property.

In yet a further example, the luminescence modifying group and/or the fluorophore and/or the complex of the invention is a component covalently bound to the analyte.

Other aspects, objects and advantages of the invention will be apparent from the detailed description that follows.

BRIEF DESCRIPTION OF THE DRAWINGS

FIG. 13 is a table of exemplary fluorophores of use in the compounds of the invention.

DETAILED DESCRIPTION OF THE INVENTION

Definitions

Figure 1A:
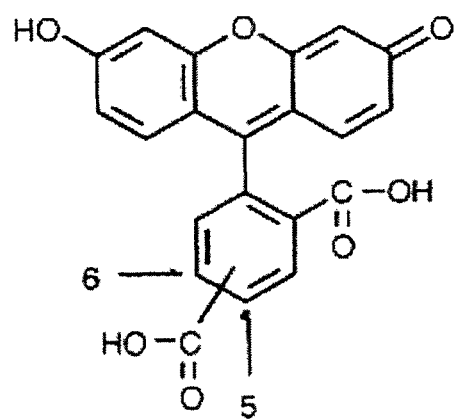
FIG. 1 Structures of exemplary acceptors for the four major 4-Tb Donor peaks. A) Structure of 5/6 Carboxy Fluorscein (FAM) with 494 nm excitation by Tb Donor Peak at 492 nm and a 518 nm emission. B) 5/6 tetramethylrhodamine Isothiocyanate (TRITC) with 544 nm excitation by Tb Donor Peak at 545 nm and a 572 nm emission. C) Texas Red Sulfonyl Chloride with 588 nm excitation by Tb Donor Peak at 590 nm and a 612 nm emission. D) Cy5 with 649 nm excitation by Tb Donor Peak at 620 nm and a 670 nm emission.
Figure 1B:
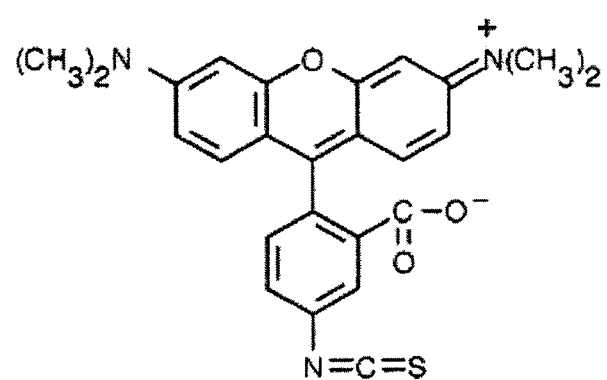
Figure 1C:
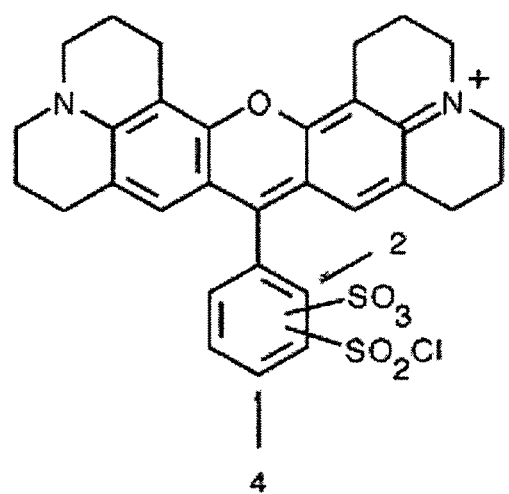
Figure 1D:
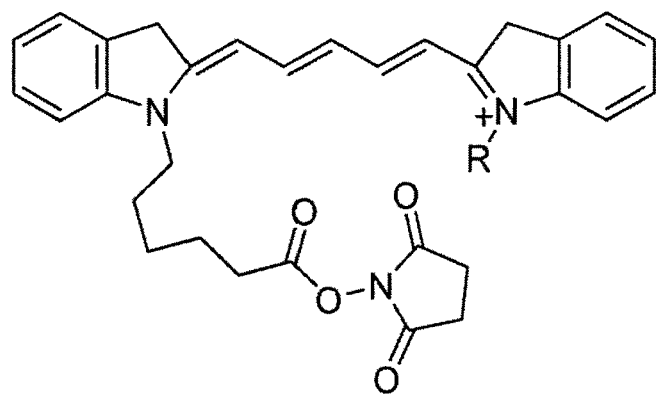
Figure 2:
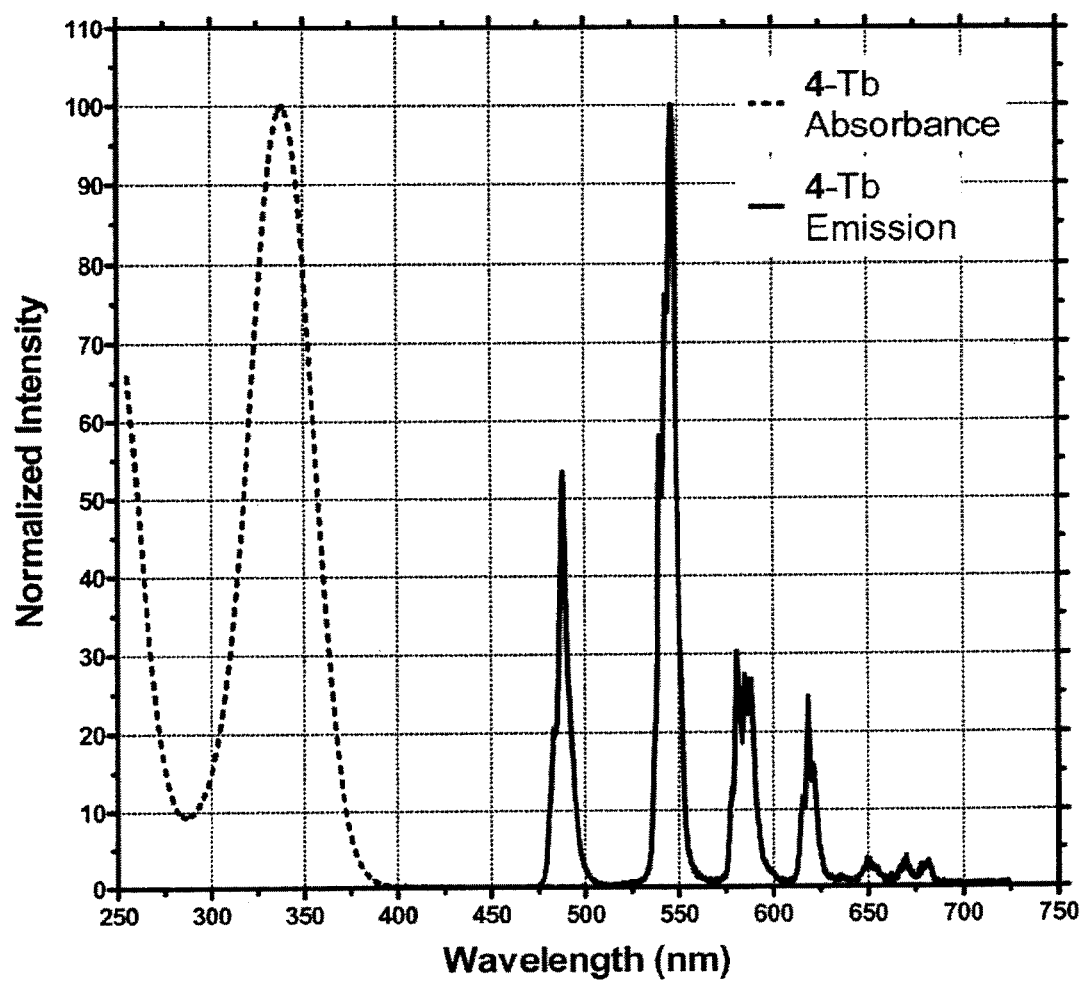
FIG. 2 Absorption and emission spectra of 4-Tb fluorophore. The four emission peaks (A, B, C, and D) characteristic of terbium offer the potential for multicolor emission based on fluorescent resonance energy transfer.

"Analyte", as used herein, means any compound or molecule of interest for which a diagnostic test is performed, such as a biopolymer or a small molecular bioactive material. An analyte can be, for example, a cell, a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, nucleic acid, lipid, without limitation. An analyte can have bound thereto a fluorophore as defined herein and/or a compound according to Formula I. An analyte can be bound to a carrier moiety or to a solid support.

As used herein, "energy transfer" refers to the process by which energy emission of an excited donor (e.g., a luminescent group) is altered by an acceptor (e.g., a luminescence-modifying group). When the luminescence-modifying group is a quenching group then the energy emission from the luminescent group is attenuated (quenched). Energy transfer mechanisms include luminescence resonance energy transfer, e.g., by dipole-dipole interaction (e.g., in longer range energy transfer) or electron transfer (e.g., across shorter distances). An exemplary mechanism involves transfer of energy from a metal chelate to a fluorophore (or a quencher or other luminescence modifying group) covalently bound to the chelating moiety through a linker, such as the compounds of the invention described herein. While energy transfer is often based on spectral overlap of the emission spectrum of the luminescent group and the absorption spectrum of the luminescence-modifying group, (in addition to distance between the groups) it has been demonstrated that spectral overlap is not necessarily required for energy transfer to occur (see, e.g., Latva et al., U.S. Pat. No. 5,998,146, which is incorporated herein by reference) and this type of energy transfer is encompassed within the present invention. Energy transfer between members of an energy transfer pair occurs when the members of the pair are in "operative proximity," which is defined herein as a distance between the members of the pair that allows detectable energy transfer to occur. It is to be understood that any reference to "energy transfer" in the instant application encompasses all mechanistically-similar phenomena.

"Energy transfer pair" is used to refer to a group of molecules that participate in energy transfer. Such complexes may comprise, for example, two luminescent groups, which may be different from one-another and one quenching group, two quenching groups and one luminescent group, or multiple luminescent groups and multiple quenching groups. In cases where there are multiple luminescent groups and/or multiple quenching groups, the individual groups may be different from one another. Typically, one of the molecules acts as a luminescent group, and another acts as a luminescence-modifying group. The preferred energy transfer pair of the invention comprises a luminescent group of the invention and a fluorophore (e.g., an organic fluorophore). The fluorophore can act as a quencher or other luminescence modifying group or, rather than a fluorophore, the acceptor-linker can be conjugated to a quencher or other luminescence modifying moiety. There is no limitation on the identity of the individual members of the energy transfer pair in this application. Generally preferred energy transfer pairs are characterized by a change in the spectroscopic properties of the pair if the distance between the individual members is altered by some critical amount. An exemplary energy transfer pair is a luminescent complex of the invention and an organic fluorophore.

As used herein, "luminescence-modifying group" refers to a molecule of the invention that can alter in any way the luminescence emission from a luminescent group. A luminescence-modifying group generally accomplishes this through an energy transfer mechanism. Depending on the identity of the luminescence-modifying group, the luminescence emission can undergo a number of alterations, including, but not limited to, attenuation, complete quenching, enhancement, a shift in wavelength, a shift in polarity, and a change in luminescence lifetime. One example of a luminescence-modifying group is a fluorophore that participates with a metal complex component of a complex of the invention in fluorescence resonance energy transfer. Another exemplary luminescence-modifying group is a quenching group.

As used herein, "quenching group" refers to any luminescence-modifying group of the invention that can attenuate at least partly the light emitted by a luminescent group. This attenuation is referred to herein as "quenching". Hence, excitation of the luminescent group in the presence of the quenching group leads to an emission signal that is less intense than expected, or even completely absent. Quenching typically occurs through energy transfer between the luminescent group and the quenching group.

"Fluorescence resonance energy transfer" or "FRET" is used interchangeably with and "LRET" and refers to an energy transfer phenomenon in which the excited state energy (e.g., light) emitted by an excited luminescent group is absorbed at least partially by a luminescence-modifying group of the invention and re-emitted at a different (e.g., longer) wavelength by the luminescence-modifying group. FRET depends on energy transfer between the luminescent group and the luminescence-modifying group. The efficiency of FRET depends at least in part on the distance between the luminescence modifying group and the luminescent group. In contrast to excimers and exciplex fluorescence, FRET pairs do not require the dye molecules forming the complexes to be in very close proximity. FRET is commonly used in several detection modes to detect, characterize or identify a variety of biologically active molecules including nucleic acids, e.g., oligonucleotides, peptides (e.g., peptides including one or more protease cleaveage site) and proteins (e.g., antibodies, antigens, receptors). One of the advantages of FRET is that fluorescence arises under physiologically relevant conditions (e.g., pH between about 7 and about 8, e.g., 7.3-7.5) in comparison to exciplex fluorescence which is typically weak under aqueous conditions, requiring the addition of organic solvents or formation in a similar molecular microenvironment. In an exemplary embodiment, the compound according to Formula I is incorporated into a nucleic acid having a motif of a known dual- or multiple-labeled nucleic acid probe (e.g., Molecular Beacons, Scorpion probes, TaqMan, and the like). The compound according to Formula I and the fluorophore can be positioned analogously to the donor and acceptor moieties of such probes.

"Moiety" refers to the radical of a molecule that is attached to another moiety.

The term "targeting moiety" is intended to mean any moiety conjugated to the complexes of the invention that targets the complex to a selected target (e.g., a complementary nucleic acid, a receptor structure, an antibody, an antigen, a lectin). The targeting moiety can be a small molecule (e.g., MW<500D), which is intended to include both non-peptides and peptides. The targeting group can also be a macromolecule, which includes saccharides, lectins, receptors, ligands for receptors, proteins such as BSA, antibodies, nucleic acids, solid supports and so forth. The targeting moiety can be a component of the complex of the invention. For example, in one embodiment, the targeting moiety is the acceptor-linker (e.g., the acceptor-linker is a nucleic acid with a sequence sufficiently complementary to the target to allow hybridization between the acceptor-linker and the target). In another embodiment, the targeting moiety is a group conjugated to the functional moiety (e.g., a nucleic acid, antibody, antigen, biotin, avidin, streptavidin, etc.).

"Carrier moiety" as used herein refers to a species to which a compound according to Formula I is covalently bound through reaction of a reactive functional group on a functional moiety with a reactive functional group of complementary reactivity on the carrier moiety. Exemplary carrier moieties include nucleic acids (DNA, RNA), peptides, antibodies, antobody fragments, antigens, receptors, lectins, saccharides, lipids and the like. Further exemplary carriers include biotin, avidin, streptavidin. A "carrier moiety" can function as a "targeting moiety."

The term, "fluorophore," as used herein refers to a species of excited energy acceptors capable of generating fluorescence when excited, which has a structure other than that shown in Formula I or a luminescent metal complex of Formula I. Complexes of different metal ions incorporating the structure according to Formula I are considered to be different compounds. Thus, for example, if a Tb chelate is a complex according to Formula I, an identical Eu complex can be a "fluorophore" according to the present invention. A fluorophore can be covalently bound to a compound according to Formula I through a acceptor-linker. Alternatively, the fluorophore can be bound to a first component of an assay, and the compound according to Formula I bound to a second component of an assay. Generally, it is preferred that the fluorophore is bound to the first assay component at a position and in a manner that allows energy transfer between the compound according to Formula I and the fluorophore when the first and second assay components interact in the assay. An exemplary assay is a hybridization assay in which a fluorophore is bound to a first nucleic acid and a compound according to Formula I is bound to a second nucleic acid. Other exemplary acceptors include quenchers and luminescence modifying moieties.

As used herein, "linker" refers to a moiety that links the chelating moiety of a compound of the invention to another species (e.g., carrier moiety or solid support). Exemplary linkers join a reactive functional group ("functional moiety") or a fluorophore ("acceptor-linker") to the chelating moiety of a compound of the invention. A linker can be any useful structure including, but not limited to 0 order linkers, acyl, substituted or unsubstituted alkyl, substituted or unsubstituted aryl, substituted or unsubstituted heteroalkyl, and substituted or unsubstituted heterocycloalkyl. Further exemplary linkers include substituted or unsubstituted branched or linear $C_1$-$C_{10}$ substituted or unsubstituted alkyl and substituted or unsubstituted heterolkyl. Other linkers include nucleic acids and peptides, such as PCR probes, hybridization probes and peptides that include protease cleaveage sites. Still further linkers include antibodies, lectins, haptens and saccharides.

As used herein, "nucleic acid" means DNA, RNA, single-stranded, double-stranded, or more highly aggregated hybridization motifs, and any chemical modifications thereof. Exemplary modifications include, but are not limited to, those providing chemical groups that incorporate additional charge, polarizability, hydrogen bonding, electrostatic interaction, and fluxionality to the nucleic acid ligand bases or to the nucleic acid ligand as a whole. Such modifications include, but are not limited to, peptide nucleic acids, phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Modifications can also include 3' and 5' modifications such as capping with a quencher, a fluorophore, an intercalator, a minor groove binder or another moiety. Exemplary nucleic acids will bind, preferably under stringent conditions, to a nucleic acid of diagnostic interest. Preferred nucleic acids of diagnostic interest are those that are correlated with a disease, condition or syndrome, or progression, amelioration or treatment of a disease, condition or syndrome. Nonlimiting examples of nucleic acids include those that are sufficiently complementary, to bind under stringent conditions, to a nucleic acid from hepatitis (e.g., A, B or C), human papilloma virus (HPV), human immunodeficiency virus (HIV), influenza, Severe Acute Respiratory Syndrome Virus (SARS), gram positive and gram negative bacteria, and antibiotic resistant bacterial infections, e.g., multiple resistant Staphylococcus (MRS).

"Peptide" refers to a homo- or hetero-polymer or oligomer in which the monomers are amino acids and are joined together through amide bonds, alternatively referred to as a polypeptide. When the amino acids are alpha-amino acids, either the L-optical isomer or the D-optical isomer can be used. Additionally, unnatural amino acids, for example, beta,-alanine, phenylglycine and homoarginine are also included. Commonly encountered amino acids that are not gene-encoded may also be used in the present invention. All of the amino acids used in the present invention may be either the D- or L-isomer. The L-isomers are generally preferred. The term "peptide" or "polypeptide", as used herein, refers to naturally occurring as well as synthetic peptides. In addition, peptido-mimetics are also useful in the present invention. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

"Reactive functional group," as used herein, has the meaning generally recognized in the art of synthetic chemistry, particularly bioconjugate chemistry. Exemplary reactive functional groups included, without limitation, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Methods to prepare each of these functional groups are well-known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989).

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "alkyl," by itself or as part of another substituent, means, unless otherwise stated, a straight or branched chain, or cyclic hydrocarbon radical, or combination thereof, which may be fully saturated, mono- or polyunsaturated and includes mono-, di- and multivalent radicals, having the number of carbon atoms designated (i.e. C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds (i.e., alkenyl and alkynyl moieties). Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. Alkyl groups that are limited to hydrocarbon groups are termed "homoalkyl".

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl and heteroalkyl groups attached to the remainder of the molecule via an oxygen atom, a nitrogen atom (e.g., an amine group), or a sulfur atom, respectively.

The term "heteroalkyl," by itself or in combination with another term, means, unless otherwise stated, a stable straight or branched chain, or cyclic alkyl moiety, or combinations thereof, consisting of a number (e.g., a stated number) of carbon atoms and at least one heteroatom selected from the group consisting of O, N, Si, B and S, and wherein the nitrogen and sulfur atoms may optionally be oxidized and the nitrogen heteroatom may optionally be quaternized. The heteroatom(s) O, N, S, B and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$,—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "acyl" refers to a species that includes the moiety —C(O)R, where R has the meaning defined herein.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: substituted or unsubstituted aryl, substituted or unsubstituted heteroaryl, substituted or unsubstituted heterocycloalkyl, —OR', =O, =NR', =N—OR', —NR'R", —SR', -halogen, —SiR'R''R''', —OC(O)R', —C(O)R', —CO$_2$R', —CONR'R'', —OC(O)NR'R'', —NR''C(O)R', —NR'—C(O)NR''R''', —NR''C(O)$_2$R', —NR—C(NR'R''R''')=NR'''', —NR—C(NR'R'')=NR''', —S(O)R', —S(O)$_2$R', —S(O)$_2$NR'R'', —NRSO$_2$R', —CN and —NO$_2$ in a number ranging from zero to (2m'+1), where m' is the total number of carbon atoms in such radical. R', R'', R''' and R'''' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R'', R''' and R'''' groups when more than one of these groups is present. When R' and R'' are attached to the same nitrogen atom, they can be combined with the nitrogen atom to form a 5-, 6-, or 7-membered ring. For example, —NR'R'' is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: substituted or unsubstituted alkyl, substituted or unsubstituted heteroalkyl, substituted or unsubstituted heterocycloalkyl, substituted or unsubstituted aryl, substituted or unsubstituted heteroaryl, halogen, —OR', =O, =NR', =N—OR', —NR'R'', —SR', -halogen, —SiR'R''R''', —OC(O)R', —C(O)R', —CO$_2$R', —CONR'R'', —OC(O)NR'R'', —NR''C(O)R', —NR'—C(O)NR''R''', —NR''C(O)$_2$R', —NR—C(NR'R''R''')=NR'''', —NR—C(NR'R'')=NR''', —S(O)R', —S(O)$_2$R', —S(O)$_2$NR'R'', —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R'', R''' and R'''' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R'', R''' and R'''' groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR''R''')$_d$—, where s and d are independently integers of from 0 to 3, and X is —O—, —NR'—, —S—, —S(O)—, —S(O)$_2$—, or —S(O)$_2$NR'—.

The substituents R, R', R'' and R''' are preferably independently selected from hydrogen or substituted or unsubstituted (C$_1$-C$_6$)alkyl.

As used herein, the term "heteroatom" includes oxygen (O), nitrogen (N), sulfur (S), silicon (Si) and boron (B).

A "linkage fragment" is formed by reaction of a reactive functional group on one species with reactive functional group of complementary reactivity on another species (e.g., a fluorophore and a acceptor-linker, a functional moiety and a carrier moiety (or solid support). Exemplary linkage fragments formed by such reactions include, but are not limited to S, SC(O)NH, SC(O)(NH)$_2$, HNC(O)S, SC(O)O, O, NH, NHC(O), (NH)$_2$C(O), (O)CNH and NHC(O)O, and OC(O)NH, CH$_2$S, CH$_2$O, CH$_2$CH$_2$O, CH$_2$CH$_2$S, (CH$_2$)$_o$O, (CH$_2$)$_o$S or (CH$_2$)$_o$Y'-PEG wherein, Y' is S, NH, NHC(O), C(O)NH, NHC(O)O, OC(O)NH, or O and o is an integer from 1 to 50.

The symbol "R" is a general abbreviation that represents a substituent group that is selected from acyl, substituted or unsubstituted alkyl, substituted or unsubstituted heteroalkyl, substituted or unsubstituted aryl, substituted or unsubstituted heteroaryl, and substituted or unsubstituted heterocyclyl groups.

The present invention includes all salt forms of those molecules that contain ionizable functional groups, such as basic and acidic groups. The term "pharmaceutically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *Journal of Pharmaceutical Science*, 66: 1-19 (1977)). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

When a residue (such as "R") is defined herein as a single negative charge, then the residue can include a cationic counterion. The resulting salt form of the compound is encompassed in the structure as presented.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The graphic representations of racemic, ambiscalemic and scalemic or enantiomerically pure compounds used herein are taken from Maehr, *J. Chem. Ed.,* 62: 114-120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but not implying any absolute stereochemistry; and wedge outlines and dotted or broken lines denote enantiomerically pure compounds of indeterminate absolute configuration.

The terms "enantiomeric excess" and diastereomeric excess" are used interchangeably herein. Compounds with a single stereocenter are referred to as being present in "enantiomeric excess," those with at least two stereocenters are referred to as being present in "diastereomeric excess." Preferred "excesses are at least 90%, 92%, 94%, 96% or 98%.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Introduction

The present invention provides a class of luminescent probes that are based on metal ion (e.g., lanthanide, such as terbium and europium) chelates, which are formed between the metal ion and a novel class of macrocyclic ligands, such as those set forth in Formula I. These complexes exhibit high stability as well as high quantum yields of luminescence in aqueous media without the need for secondary activating agents such micelles or fluoride. Preferred ligands are macrocyclic structures incorporating an aromatic moiety, e.g., phthalamidyl, salicylamidyl, within their macrocyclic framework. The macrocycles of the invention are characterized by surprisingly high kinetic stability and unexpectedly low, nonspecific binding to a variety of different polypeptides such as antibodies and proteins. These characteristics distinguish the macrocyclic structures of the invention from known, open-structured ligands.

Lanthanide complexes of the invention exhibit high quantum efficiencies and relatively high absorption coefficients. These properties make metal complexes of ligands of the invention useful for time resolved luminescence resonance energy transfer (TR-LRET) applications (e.g., homogeneous TR-LRET) in which donor and acceptor molecules are used at low concentrations. Complexes of the present invention find use in any application requiring strong luminescence under aqueous conditions including medical diagnostics and bioanalytical assay systems, such as immunoassays, peptide cleavage assays, DNA reporter assays and the like. In addition, these complexes and their derivatives have wide applicability in nanotechnology (incorporation into particles) and material science. In an exemplary embodiment, a complex of the invention is embedded in a solid material, allowing for the transmission of light.

Luminescent metal chelates of the invention can be used with other fluorophores or quenchers as components of energy transfer probes. Many fluorescent labels are useful in combination with the complexes of the invention and many such labels are available from commercial sources, such as SIGMA (Saint Louis) or Invitrogen, that are known to those of skill in the art. Furthermore, those of skill in the art will recognize how to select an appropriate fluorophore for a particular application and, if it is not readily available, will be able to synthesize the necessary fluorophore de novo or synthetically modify commercially available fluorescent compounds to arrive at the desired fluorescent label.

In addition to small-molecule fluorophores, naturally occurring fluorescent proteins and engineered analogues of such proteins are useful with the compounds of the present invention. Such proteins include, for example, green fluorescent proteins of cnidarians (Ward et al., *Photochem. Photobiol.* 1982, 35:803-808; Levine et al., *Comp. Biochem. Physiol.* 1982, 72B:77 85), yellow fluorescent protein from Vibrio fischeri strain (Baldwin et al., *Biochemistry* 1990, 29:5509 15), Peridinin-chlorophyll from the *dinoflagellate Symbiodinium* sp. (Morris et al., *Plant Molecular Biology* 1994, 24:673:77), phycobiliproteins from marine cyanobacteria, such as *Synechococcus*, e.g., phycoerythrin and phycocyanin (Wilbanks et al., *J. Biol. Chem.* 1993, 268:1226 35), and the like.

The compounds of the invention can be used as probes, as tools for separating particular ions from other solutes, as probes in microscopy, enzymology, clinical chemistry, molecular biology and medicine. The compounds of the invention are also useful as therapeutic agents and as diagnostic agents in imaging methods. Moreover, the compounds of the invention are useful as components of optical amplifiers of light, waveguides and the like. Furthermore, the compounds of the invention can be incorporated into inks and dyes, such as those used in the printing of currency and other instruments.

In one embodiment, the compounds of the invention show luminescence after exciting them in any manner known in the art, including, for example, with light or electrochemical energy (see, for example, Kulmala et al, *Analytica Chimica Acta* 1999, 386:1). The luminescence can, in the case of chiral compounds of the invention, be circularly polarized (see, for example, Riehl et al., *Chem. Rev.* 1986, 86:1). The present invention provides chiral chelates according to Formula I that are enantiomerically or diastereomerically enriched with respect to one enantionmer or diastereomer.

The compounds, probes and methods discussed in the following sections are generally representative of the compositions of the invention and the methods in which such compositions can be used. The following discussion is intended as illustrative of selected aspects and embodiments of the present invention and it should not be interpreted as limiting the scope of the present invention.

Compositions

In a first embodiment, the invention provides a compound that includes a chelate structure according to Formula I:

(I)

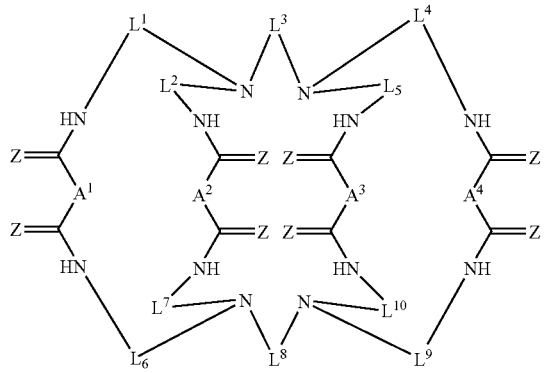

wherein the compound preferably includes at least one acceptor-linker, which is optionally covalently bound to a fluorophore, e.g., through a linkage fragment. In another embodiment, the compound of the invention includes at least one functional moiety. In a still further embodiment, a reactive functional group on the functional moiety is converted to a linkage fragment by reaction with a complementary reactive group on a carrier moiety, e.g., a nucleic acid, a peptide, an antibody, a saccharide, lectin, receptor or antigen, or a solid support.

In Formula I, each Z is a member independently selected from O and S. $L^1$, $L^2$, $L^3$, $L^4$, $L^5$, $L^6$, $L^7$, $L^8$, $L^9$ and $L^{10}$ ("$L^x$" moieties) are linker groups independently selected from substituted or unsubstituted alkyl, substituted or unsubstituted heteroalkyl, substituted or unsubstituted aryl, substituted or unsubstituted heteroaryl and substituted or unsubstituted heterocycloalkyl.

$A^1$, $A^2$, $A^3$ and $A^4$ are members independently selected from substituted or unsubstituted aryl and substituted or unsubstituted heteroaryl (e.g., azulene) moieties. In an exemplary embodiment, these moieties are independently selected from the following structure:

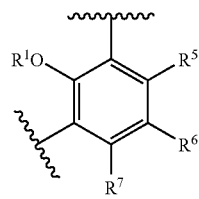

wherein each $R^1$ is a member independently selected from H, an enzymatically labile group, a hydrolytically labile group, a metabolically labile group and a single negative charge. Each $R^5$, $R^6$ and $R^7$ ("an Rx moiety") is a member independently selected from H, substituted or unsubstituted alkyl, substituted or unsubstituted heteroalkyl, halogen, CN, $CF_3$, acyl, $-SO_2NR^{17}R^{18}$, $-NR^{17}R^{18}$, $-OR^{17}$, $-S(O)_2R^{17}$, $CONR^{17}R^{18}$, $-S(O)_2OR^{17}$, $-OC(O)R^{17}$, $-C(O)NR^{17}R^{18}$, $-NR^{17}C(O)R^{18}$, $-NR^{17}SO_2R^{18}$, and $-NO_2$, wherein $R^6$ and a member selected from $R^5$, $R^7$ and combinations thereof are optionally joined to form a ring system which is a member selected from substituted or unsubstituted cycloalkyl, substituted or unsubstituted heterocycloalkyl, substituted or unsubstituted aryl and substituted or unsubstituted heteroaryl.

$R^{17}$ and $R^{18}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and $R^{17}$ and $R^{18}$, together with the atoms to which they are attached, are optionally joined to form a 5- to 7-membered ring.

In an exemplary embodiment, a compound according to Formula I is covalently attached through the functional moiety to a carrier molecule.

Exemplary compounds according to any of the embodiments discussed above, are those in which at least one $L^x$ or $R^x$ moiety is functionalized with a acceptor-linker, optionally bound to a fluorophore, e.g., through a linkage fragment. In another embodiment, at least one of $L^x$ or $R^x$ moiety is functionalized with a functional moiety (optionally bound to a carrier moiety or solid support, e.g., through a linkage fragment). In yet another exemplary embodiment, one of these $L^x$ or $R^x$ groups is functionalized with a acceptor-linker (optionally bound to a fluorophore) and the same or a different $L^x$ or $R^x$ moeity is functionalized with a functional moiety (optionally bound to a carrier moiety or solid support).

Thus, the present invention provides compounds according to Formula I in which at least one $L^x$ moiety is substituted with a group selected from:

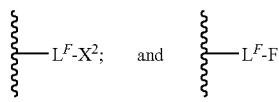

in which $L^F$ is a acceptor-linker as described herein, and $X^2$ is a reactive functional group. F is a fluorophore bound to $L^F$ through a linkage fragment formed as described herein.

In another embodiment, the invention provides compounds according to Formula I in which at least one $L^x$ moiety is substituted with a group selected from:

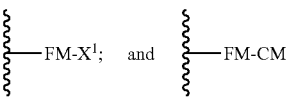

in which FM is a functional moiety as described herein, having as a component a reactive functional group, $X^1$. CM is a carrier moiety (or solid support) bound to FM through a linkage fragment formed as described herein.

In still a further embodiment, the invention provides a compound according to Formula I in which at least one $L^x$ moiety is substituted with a group selected from:

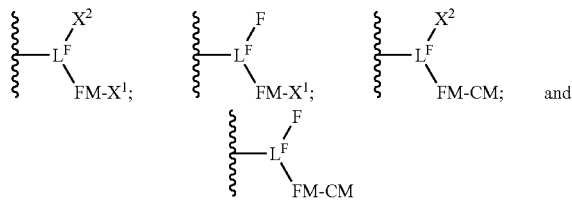

in which the moieties are as described above. As will be appreciated by those of skill in the art, rather than a fluorophore, the acceptor-linker can be conjugated to one or more quencher or other luminescence modifying moiety.

In an exemplary embodiment, the present invention provides a composition comprising a chelate according to Formula I, combined with a fluorophore. The chelate and the fluorophore are preferably both linked to a carrier moiety: each can be linked to the same carrier moiety or to a different carrier moiety. It is generally preferred that the chelate be complexed with a metal ion selected such that the chelate forms an energy transfer pair with the fluorophore. In general, the metal complex will serve as the donor fluorophore, and will have a longer excited state lifetime than the acceptor fluorophore. In an exemplary embodiment, the donor fluorophore is a lanthanide chelate. In another exemplary embodiment, the acceptor fluorophore is an organic fluorophore, e.g., a polyaromatic hydrocarbon (e.g., a hetrocyclic compound).

Transfer of excited state energy from the donor fluorophore to the acceptor fluorophore, provides an acceptor fluorophore with a longer excited state lifetime than and identical fluorophore that is not excited by the donor. The acceptor fluorophore generally luminesces at a wavelength longer than that of the energy incoming from the donor.

In another exemplary embodiment, the compositions of the invention include multiple donor fluorophores. In a further embodiment, the compositions of the invention include multiple acceptor fluorophores. The compositions can include both multiple donor and multiple acceptor fluorophores (or quenchers or other luminescence modifying moieties).

In one embodiment, the compound according to Formula I attached to a carrier molecule or solid support is combined with a carrier moiety or solid support bound to a fluorescent species. It is generally preferred that at least one of the carrier moieties or solid supports is an assay component. An example of this embodiment is a first nucleic acid conjugated to a luminescent metal complex according to Formula I, which is combined in an assay with a fluorophore that is conjugated to a second nucleic acid, which is complementary to the first nucleic acid (e.g., the two hybridize under stringent conditions). Preferably, when the two nucleic acids hybridize the luminescent metal complex according to Formula I and the fluorophore are in operative proximity and are positioned to allow energy exchange between them (preferably from the luminescent metal complex to the fluorophore).

The luminescent complexes according to Formula I, in conjunction (e.g., operative contact allowing exchange of energy) with energy transfer to a fluorophore, provides a luminescent system that is tunable with respect to emission wavelength. The emission wavelength is tunable because, when energy transfer is chosen to be large, emission color is principally determined by the emission wavelength of the fluorophore, which can be selected for its output color.

The complexes in conjunction with the fluorophore are also tunable with respect to emission lifetime because the lifetime is determined by the efficiency of energy transfer from the complex of Formula I to the fluorophore. The fluorophore typically has a short lifetime. Because it is continuously excited by the luminescent complex of Formula I, its emission intensity decays with a lifetime related to the lifetime of the luminescent complex. The lifetime can be tuned by altering the distance between the luminescent complex and the fluorophore. The Foerster equation is of use to predict the lifetime of the energy transfer pair.

In another exemplary embodiment, the compound of the invention has the structure:

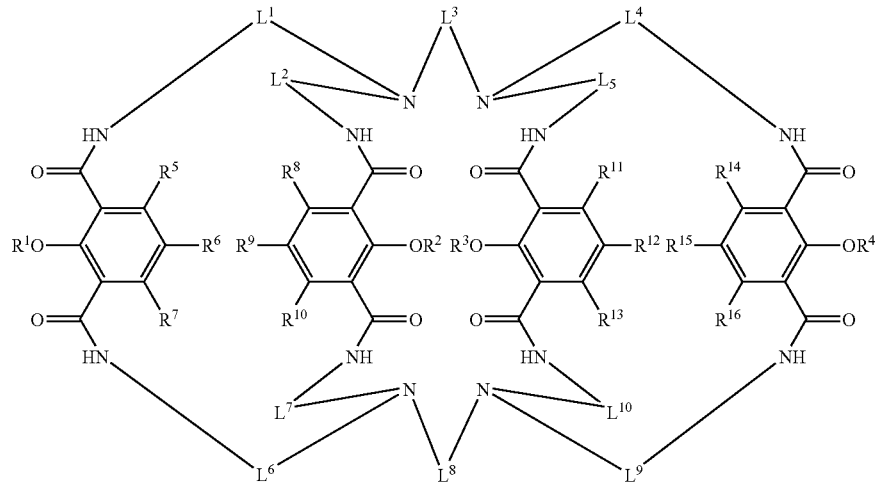

wherein $R^1$, $R^2$, $R^3$ and $R^4$ are members independently selected from H, an enzymatically labile group, a hydrolytically labile group, a metabolically labile group, a group that is cleaved by incident light and a single negative charge. The substituents and attributes of compounds according to this embodiment are as described above with reference to Formula I. Any one or more than one of $L^1$, $L^2$, $L^3$, $L^4$, $L^5$, $L^6$, $L^7$, $L^8$, $L^9$ and $L^{10}$ can be substituted with one or more functional moiety and/or acceptor-linker.

In another exemplary embodiment, the linker moieties $L^1$, $L^2$, $L^3$, $L^4$, $L^5$, $L^6$, $L^7$, $L^8$, $L^9$ and $L^{10}$ are members independently selected from substituted or unsubstituted $C_1$ to $C_6$ alkyl. Exemplary compounds include those in which $L^1$, $L^2$, $L^3$, $L^4$, $L^5$, $L^6$, $L^7$, $L^8$, $L^9$ and $L^{10}$ are members independently selected from substituted or unsubstituted ethyl. An exemplary ligand according to this embodiment has the structure:

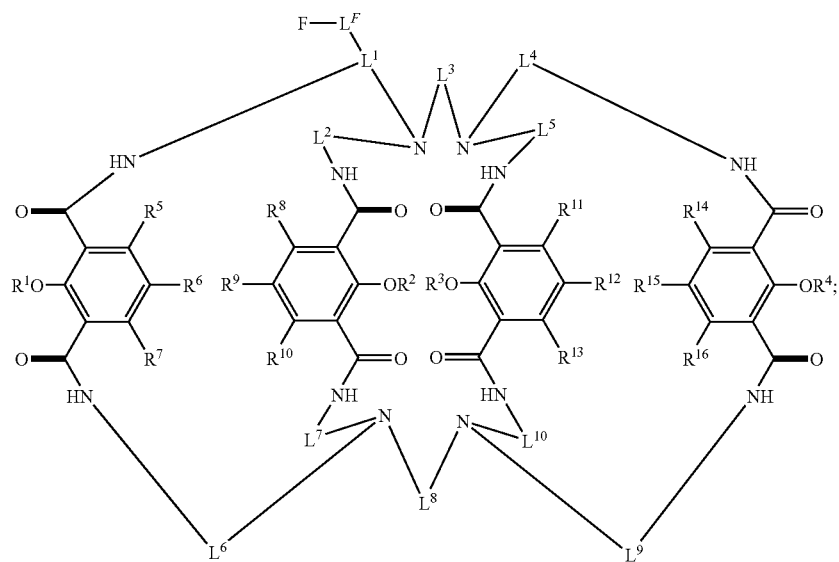
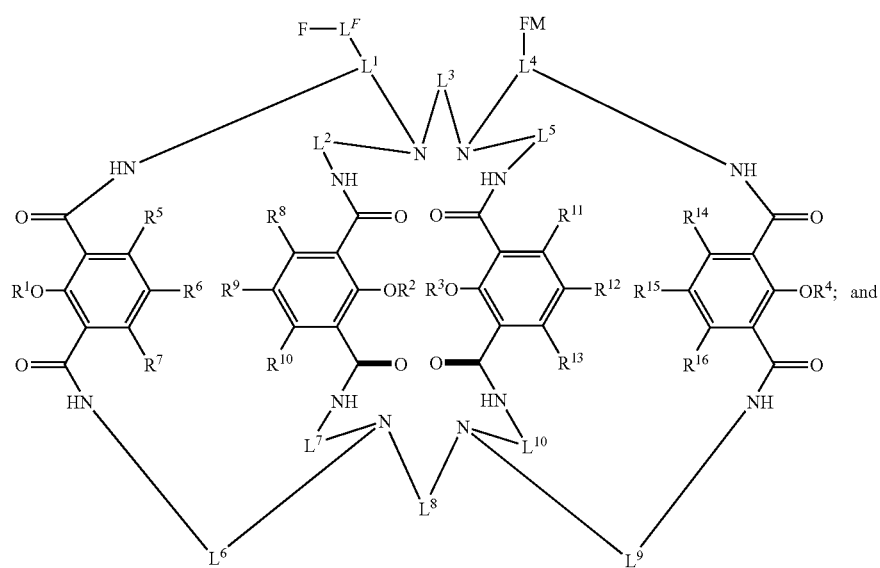

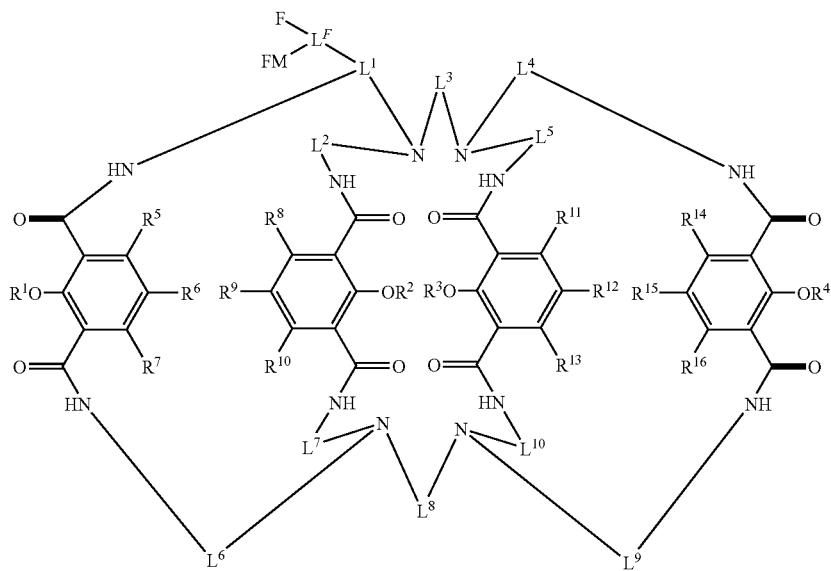

wherein $L^F$ is the acceptor-linker, F represents the fluorophore and FM is the functional moiety. As will be appreciated by those of skill, the acceptor-linker and functional moiety can be attached to any one or more than one of $L^1$, $L^2$, $L^3$, $L^4$, $L^5$, $L^6$, $L^7$, $L^8$, $L^9$ and $L^{10}$.

In another embodiment, the compound of the invention has a formula selected from:

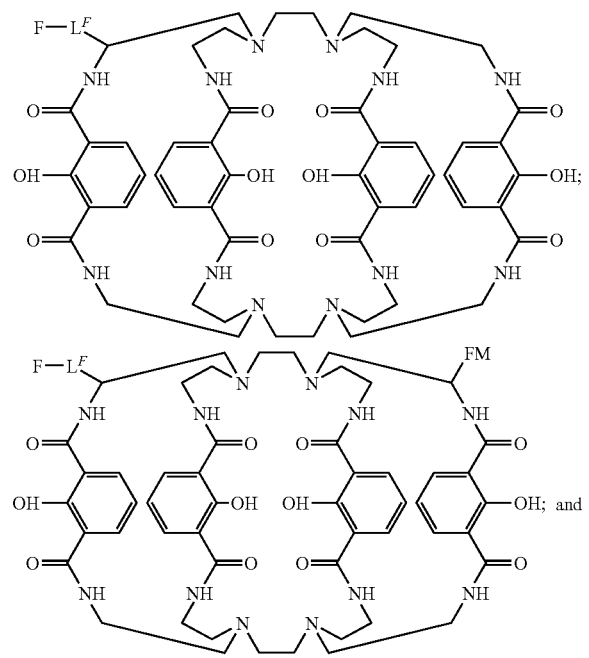

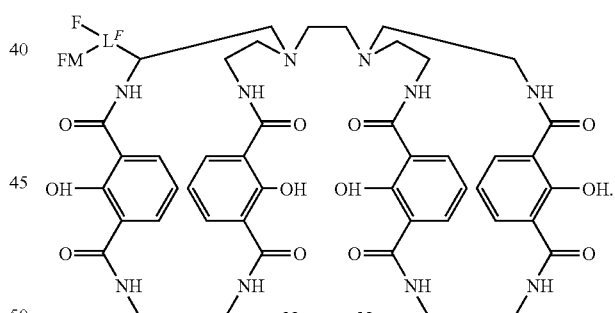

Each of the structures above is intended to include those derivatives in which the acceptor-linker is not conjugated to a fluorophore as well as those conjugated to a fluorophore. Also included are those derivatives in which the functional moiety is conjugated to a carrier moiety (CM) as well as those that are conjugated to a carrier moiety or solid support.

In another exemplary embodiment, the invention provides a compounds having the formula:

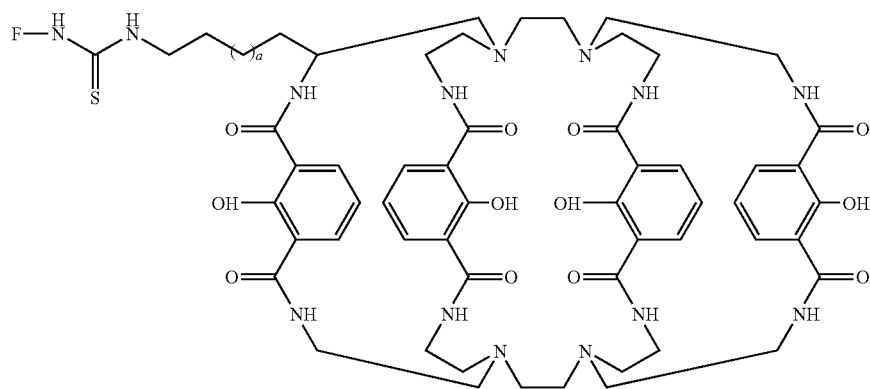
in which a is an integer greater than or equal to 0, e.g., from 0 to 10.
An exemplary compound according to this embodiment has the formula:
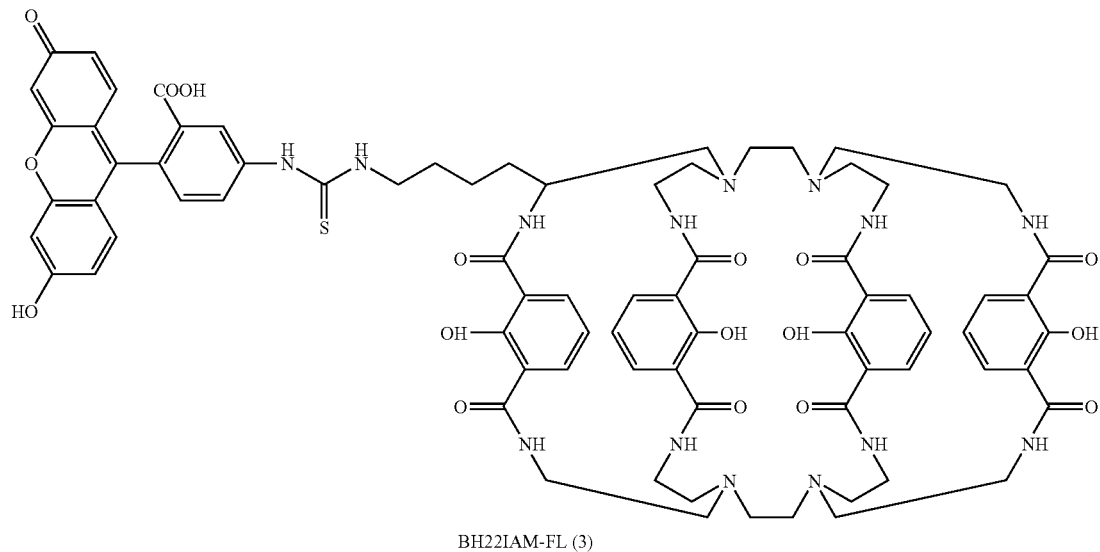 [SMILES: O=C(O)c1cc(NC(=S)NCCCCC2CN3CCNC(=O)c4cccc(c4O)C(=O)NCCN(CCNC(=O)c4cccc(c4O)C(=O)N2)CCN2CCNC(=O)c4cccc(c4O)C(=O)NCCN(CCNC(=O)c4cccc(c4O)C(=O)NCC2)CC3)ccc1-c1c2ccc(=O)cc-2oc2cc(O)ccc12]
BH22IAM-FL (3)
In another exemplary embodiment, the compound of the invention includes and amide linkage, which is more stable than the thiourea:
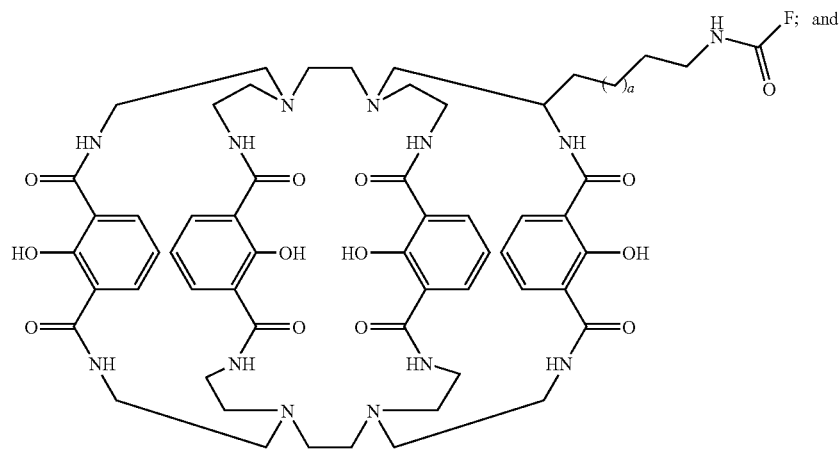

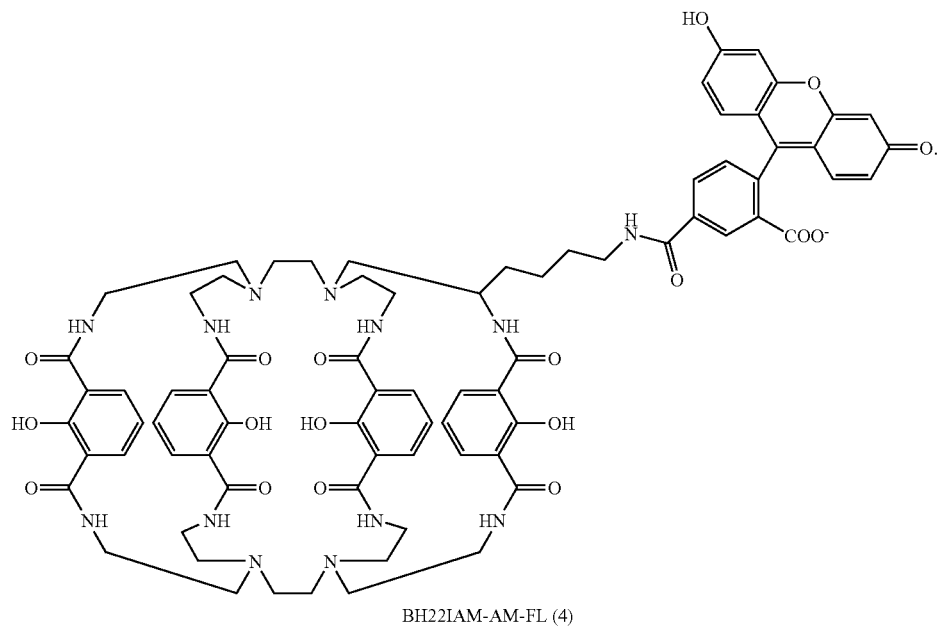
BH22IAM-AM-FL (4)
Compounds of the inventions including both a acceptor-linker moiety, optionally attached to a fluorophore, and a functional moiety, optionally attached to a carrier moiety (or solid support) are exemplified by the following compounds:
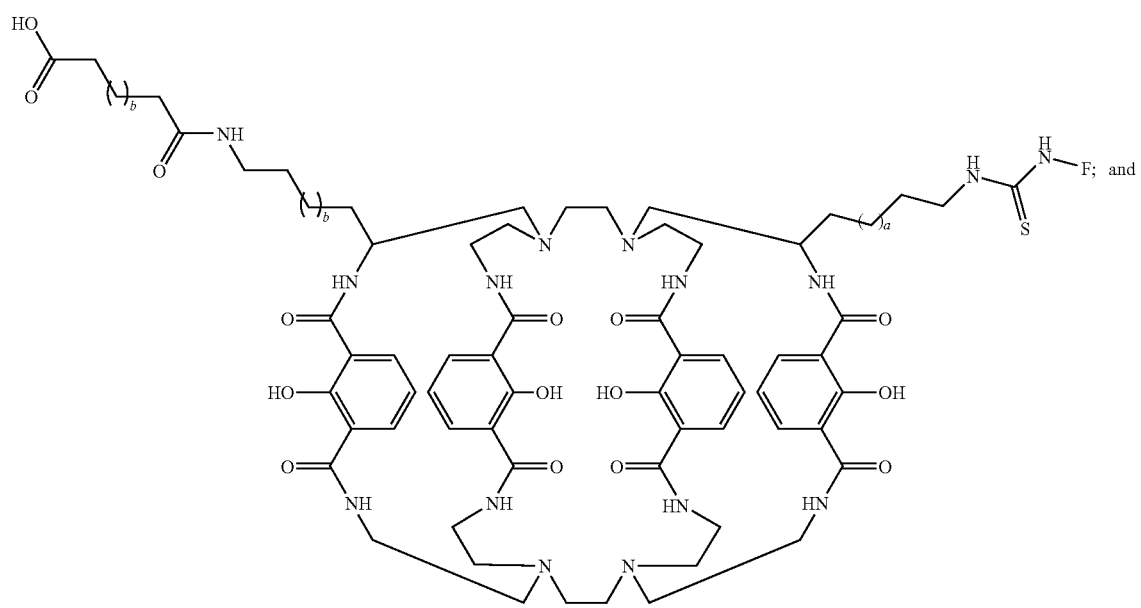

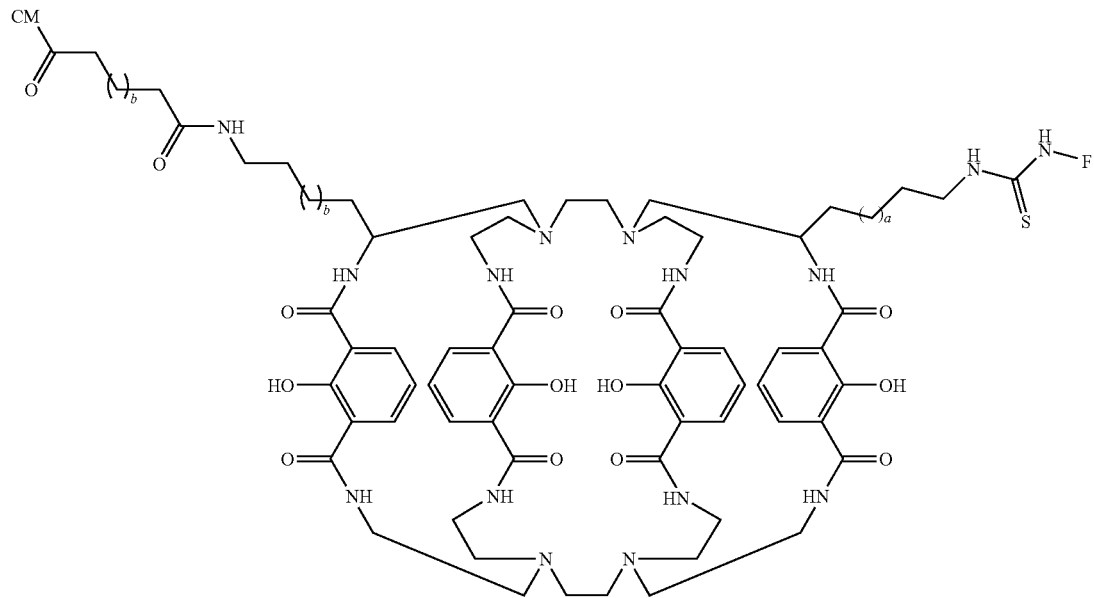
in which a and b are independently selected from integers greater than 0, e.g., integers from 0 to 15; and CM and F are as described above.
Other exemplary compound of the invention in which F is an organic fluorophore and the acceptor-linker and FM are attached at different sites on the compound according to Formula I have the formulae:
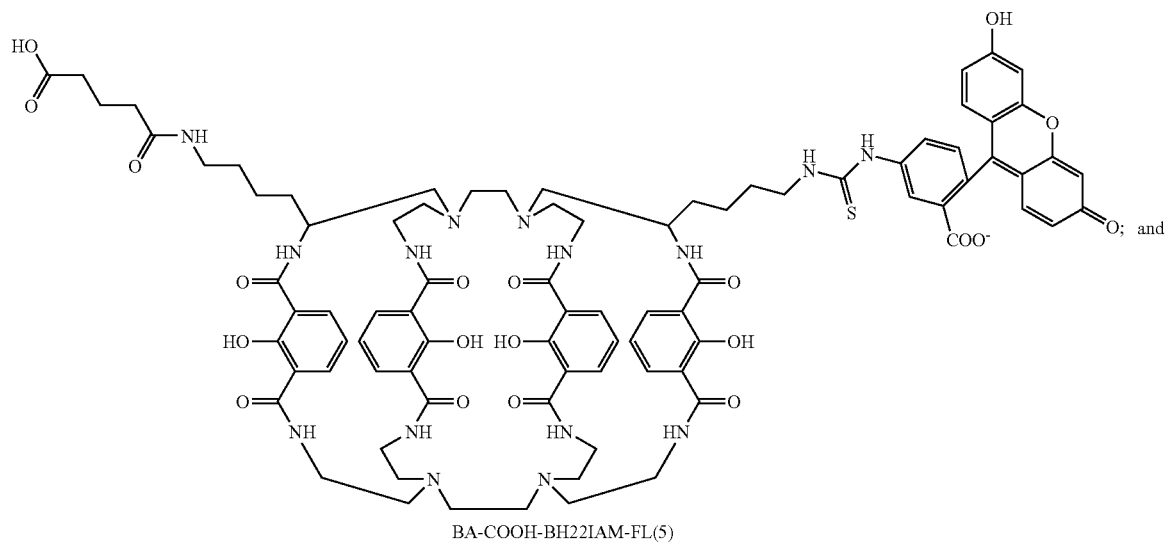
BA-COOH-BH22IAM-FL(5)

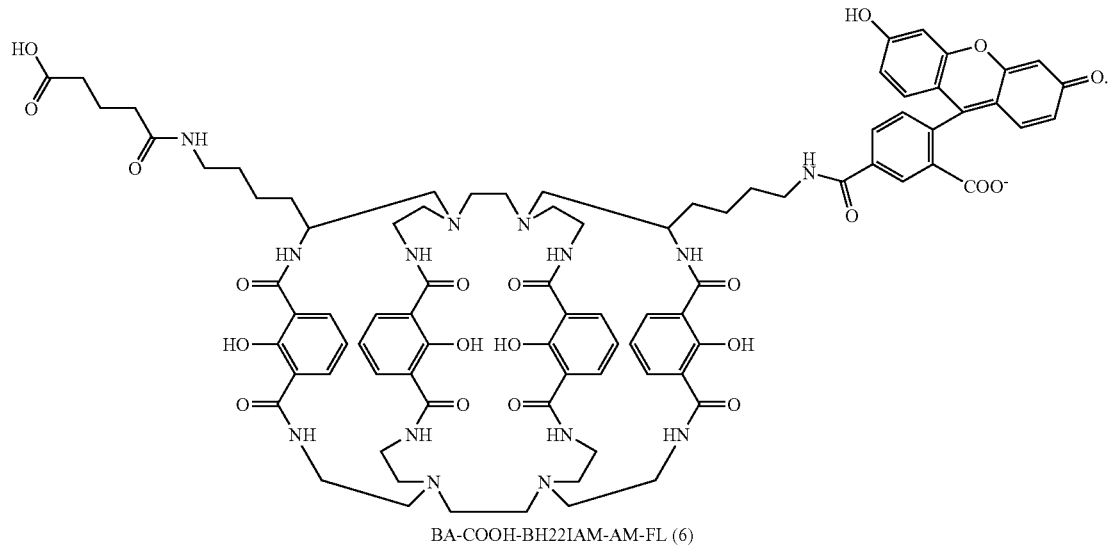
BA-COOH-BH22IAM-AM-FL (6)
In still other exemplary embodiments, the functional moiety and the acceptor-linker are components of a structure bonded at the same point (e.g., the same atom) of the chelate, providing exemplary compounds having the formulae:
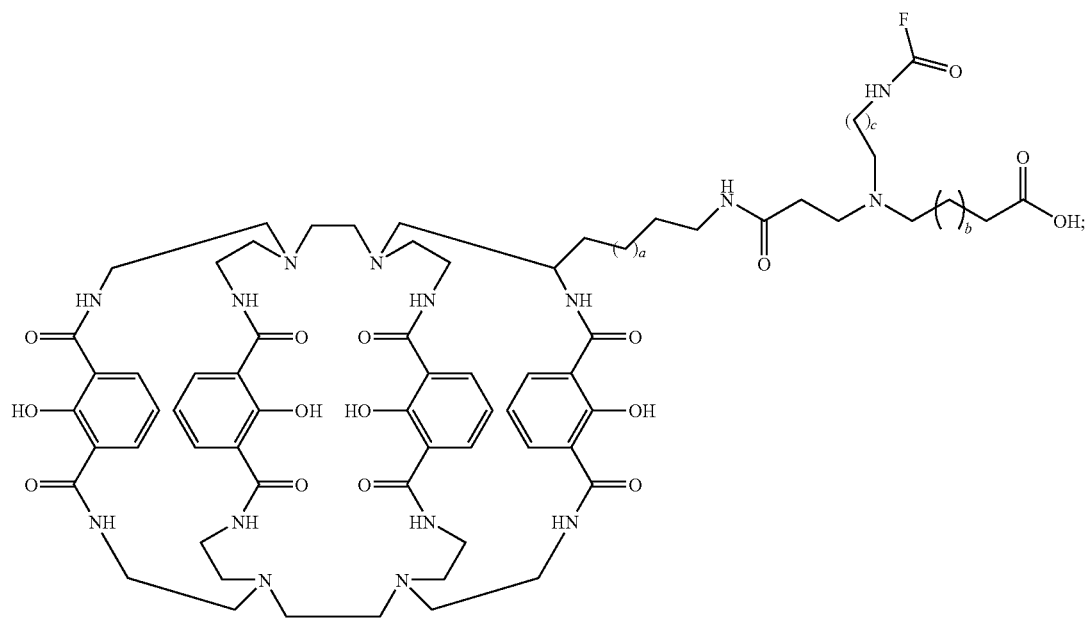

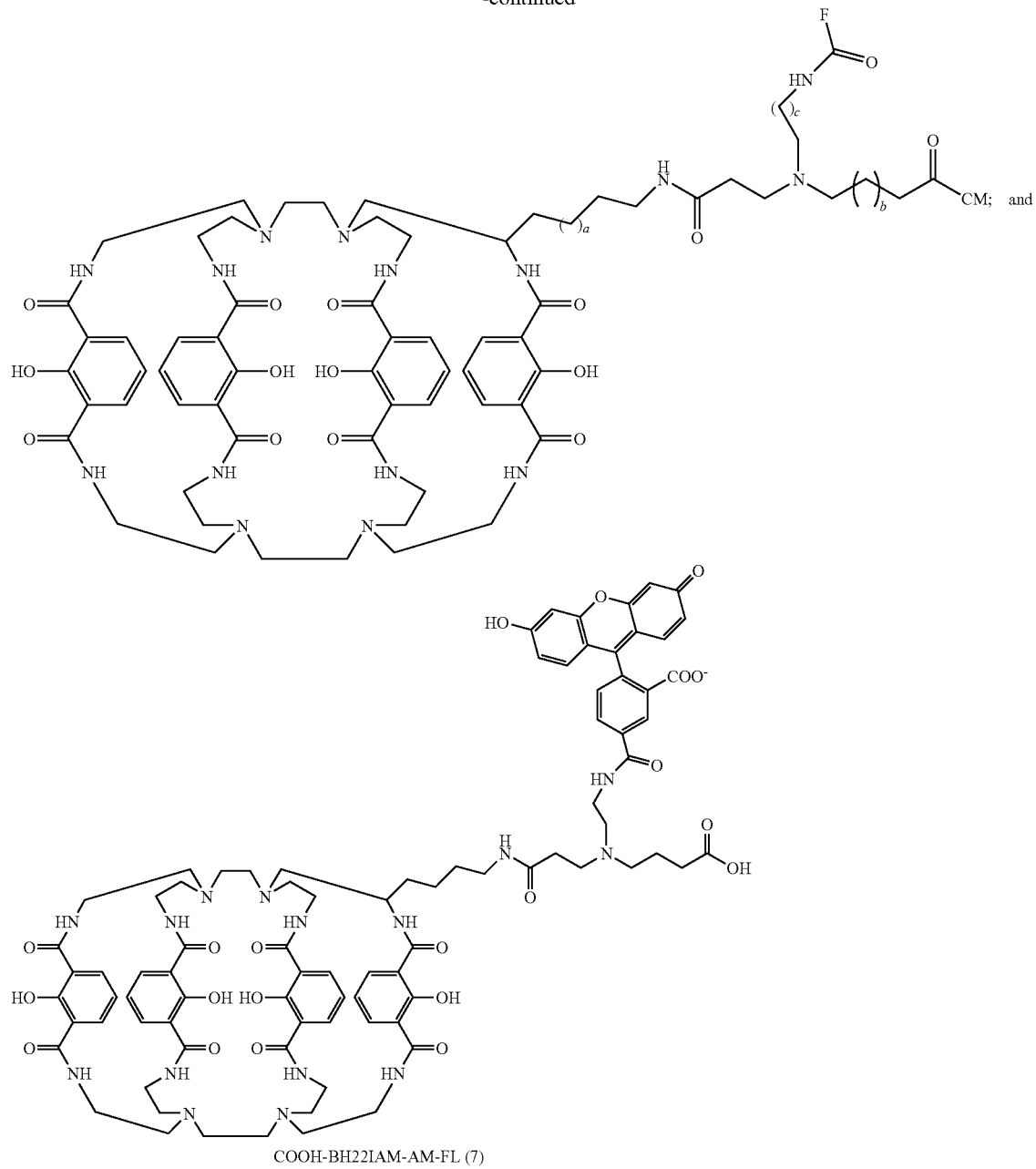

COOH-BH22IAM-AM-FL (7)

in which a, b and c are integers independently selected from integers greater than 0, e.g., integers from 0 to 15; CM is a carrier moiety (or solid support) and F is a fluorophore.

Also provided are metal complexes formed from each of the above-described chelates of the invention. In an exemplary embodiment, the metal ion is selected to provide a metal chelate that is capable of transferring energy to the fluorophore. Exemplary metal ions of use in to transfer energy to a fluorophore in compounds of this invention are lanthanide ions.

In another exemplary embodiment, the compounds of the invention emit light at an emission wavelength of the fluorophore attached to the metal chelate through the acceptor-linker. Exemplary compounds of the invention are characterized by emitting at a wavelength characteristic of the fluorophore, and the emission having a significantly enhanced lifetime. For example, compound 3, when coordinated to terbium and excited at a BH22IAM absorption wavelength (~340 nm), the metal chelate emits at 520 nm, the characteristic wavelength of fluorescein with a lifetime of 524 nsec. The new lifetime is over 100-fold longer than the lifetime for a fluorescein solution that is directly excited (<5 nsec).

In a further exemplary embodiment, the invention provides a nucleic acid probe that includes a chelate of the invention. Preferred nucleic acid probes of the invention utilize the principle of resonance energy transfer between a donor moiety and an acceptor moiety. The donor and acceptor moiety are on the same nucleic acid or are each on a different nucleic acid. A luminescent complex of the invention is generally preferred as a donor.

In one embodiment, the resonance energy transfer is fluorescence resonance energy transfer (FRET), in which a first and a second probe is labeled with a donor and an acceptor moiety. When the two probes are hybridized with each other, or are each hybridized to a common target nucleic acid sequence such that the donor and acceptor are within operative proximity, energy emitted by the donor moiety is absorbed by the acceptor moiety. In a preferred embodiment, the acceptor moiety is a fluorophore that releases the energy absorbed from the donor at a different wavelength; the emissions of the acceptor may then be measured to assess the progress of the hybridization reaction. The acceptor emission may also be characterized by a different lifetime than the emission of either the donor or acceptor in the absence of the donor.

In another exemplary embodiment, the probe is a hairpin stem-loop structure (often referred to in the art as a molecular beacon) that contains a donor which is a complex according to Formula I and an acceptor (fluorophore) moiety. The probe optionally includes a quencher moiety, such that the quencher moiety reduces the fluorescence of the donor or acceptor when the probe is in the stem-loop structure (i.e., not hybridized). When the probe is hybridized to a target nucleic acid, its conformation changes, eliminating the quenching effect, and the resulting fluorescence of the donor or acceptor moiety may be detected.

In an alternative embodiment, the present invention provides a nucleic acid probe that forms a hairpin stem-loop structure in which resonance energy transfer between the donor according to Formula I and the acceptor will decrease when the probe is hybridized with the target nucleic acid.

In another embodiment, the present invention provides that one of the nucleic acid probes is linear (non-stem-loop) and the probes are separately labeled with a luminescent chelate donor (Formula I) and an organic acceptor moiety, such that resonance energy transfer will occur when the nucleic acid probes are hybridized.

Probes based on the nucleotide sequences can be used to detect or amplify transcripts or genomic sequences encoding the same or homologous proteins. In other embodiments, the probe further comprises a label group attached thereto, e.g., the label group can be a radioisotope, an enzyme, or an enzyme co-factor. Such probes can be used as a part of a genomic marker test kit for identifying cells which express a particular protein, such as by measuring a level of the protein-encoding nucleic acid in a sample of cells, e.g., detecting the target nucleic acid mRNA levels or determining whether the gene encoding the mRNA has been mutated or deleted.

In generality, a nucleic acid probe of the invention comprises a nucleic acid probe sequence that hybridizes, e.g., hybridizes under stringent conditions, to a target nucleotide sequence of interest. These hybridization conditions include washing with a solution having a salt concentration of about 0.02 molar at pH 7 at about 60° C. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to those skilled in the art and can be found in Current Protocols in Molecular Biology, John Wiley & Sons, N.Y. (1989) 6.3.1 6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50-65° C. As used herein, a "naturally-occurring" nucleic acid molecule refers to a RNA or DNA molecule having a nucleotide sequence that occurs in nature (e.g., encodes a natural protein).

The nucleic acid probes of the invention can be DNA or RNA or chimeric mixtures or derivatives or modified versions thereof, so long as it is still capable of hybridizing to the desired target nucleic acid. In addition to being labeled with a resonance energy transfer moiety, the nucleic acid sequence can be modified at the base moiety, sugar moiety, or phosphate backbone, and may include other appending groups or labels, so long as it is still capable of priming the desired amplification reaction, or functioning as a blocking oligonucleotide, as the case may be.

For example, a nucleic acid probe of the present invention can be chemically synthesized using naturally occurring nucleotides or variously modified nucleotides designed to increase the biological stability of the molecules or to increase the physical stability of the duplex formed between the complimentary nucleic acids, e.g., phosphorothioate derivatives and acridine substituted nucleotides can be used. A preferred example of a class of modified nucleotides which can be used to generate the nucleic acid probes is a 2'-O-methyl nucleotide. Additional examples of modified nucleotides which can be used to generate the nucleic acid probes include for example 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

In another embodiment, the nucleic acid probe of the present invention comprises at least one modified sugar moiety selected from the group including but not limited to arabinose, 2-fluoroarabinose, xylulose, and hexose. In yet another embodiment, the nucleic acid probe of the present invention comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof. As stated above, a preferred example of a modified nucleotide which can be used to generate the nucleic acid probes is a 2'-O-methyl nucleotide.

Nucleic acid probes of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, *Nucl. Acids Res.* 16:3209), methylphosphonate oligonucleotides can be prepared by use of controlled pore glass polymer supports (Sarin et al., 1988, *Proc. Natl. Acad. Sci. U.S.A.* 85: 7448 7451), etc.

Once the desired oligonucleotide is synthesized, it is cleaved from the solid support on which it was synthesized and treated, by methods known in the art, to remove any protecting groups present. The oligonucleotide may then be purified by any method known in the art, including extraction and gel purification. The concentration and purity of the oligonucleotide may be determined by examining oligonucleotide that has been separated on an acrylamide gel, or by measuring the optical density at 260 nm in a spectrophotometer.

Nucleic acid probes of the invention may be labeled with donor and acceptor moieties during chemical synthesis or the label may be attached after synthesis by methods known in the art. In a specific embodiment, the following donor and acceptor pairs are used: a luminescent lanthanide chelate, e.g., terbium chelate or lanthanide chelate, is used as the donor, and an organic dye such as fluorescein, rhodamine or CY-5, is used as the acceptor. Preferably, terbium is used as a donor and fluorescein or rhodamine as an acceptor, or europium is used as a donor and CY-5 as an acceptor. In another specific embodiment, the donor is fluorescent, e.g. fluorescein, rhodamine or CY-5, and the acceptor is luminescent, e.g. a lanthanide chelate. In yet another embodiment, the energy donor is luminescent, e.g., a lanthanide chelate, and the energy acceptor may be non-fluorescent.

One of ordinary skill in the art can easily determine, using art-known techniques of spectrophotometry, which fluorophores will make suitable donor-acceptor FRET pairs. For example, FAM (which has an emission maximum of 525 nm) is a suitable donor for TAMRA, ROX, and R6G (all of which have an excitation maximum of 514 nm) in a FRET pair. Probes are preferably modified during synthesis, such that a modified T-base is introduced into a designated position by the use of Amino-Modifier C6 dT (Glen Research), and a primary amino group is incorporated on the modified T-base, as described by Ju et al. (1995, *Proc. Natl. Acad. Sci. USA* 92:4347 4351). These modifications may be used for subsequent incorporation of fluorescent dyes into designated positions of the nucleic acid probes of the present invention.

The optimal distance between the donor and acceptor moieties will be that distance wherein the emissions of the donor moiety are maximally absorbed by the acceptor moiety. This optimal distance varies with the specific moieties used, and may be easily determined by one of ordinary skill in the art using well-known techniques. The lifetime of the luminescence of the compounds of the invention is readily tuned by varying the distance between the luminescent complex and the fluorophore. For energy transfer in which the fluorophore that emits energy is to be detected, the donor and acceptor fluorophores are preferably separated when hybridized to target nucleic acid by a distance of up to 30 nucleotides, more preferably from about 1 to about 20 nucleotides, and still more preferably from about 2 to about 10 nucleotides and more preferably separated by 3, 4, 5, 6, 7, 8 or 9 nucleotides. For energy transfer wherein it is desired that the acceptor moiety quench the emissions of the donor, the donor and acceptor moieties are preferably separated by a distance of less than 10, 9, 8, 7, 6, 5, 4, 3, 2, or 1 nucleotide(s) (e.g., on the opposite strand, complementary nucleotides of a duplex structure), although a 5 nucleotide distance (one helical turn) is also advantageous for use.

The nucleic acid probes of the invention have use in nucleic acid detection, or amplification reactions as primers, or in the case of triamplification, blocking oligonucleotides, to detect or measure a nucleic acid product of the amplification, thereby detecting or measuring a target nucleic acid in a sample that is complementary to a 3' primer sequence. Accordingly, the nucleic acid probes of the invention can be used in methods of diagnosis, wherein a sequence is complementary to a sequence (e.g., genomic) of an infectious disease agent, e.g. of human disease including but not limited to viruses, bacteria, parasites, and fungi, thereby diagnosing the presence of the infectious agent in a sample of nucleic acid from a patient. The target nucleic acid can be genomic or cDNA or mRNA or synthetic, human or animal, or of a microorganism, etc.

Functional Moiety/Acceptor-Linker

The compounds of the invention include one or more structure referred to herein as a functional moiety and acceptor-linker. These moieties have a structure appropriate to allow their covalent attachment to a fluorophore (e.g., an organic fluorophore) or a carrier moiety (or solid support), respectively. Prior to conjugation with a fluorophore or carrier moiety (or solid support), the acceptor-linker and the functional moiety include a reactive functional group.

In a further embodiment, the acceptor-linker and/or the functional moiety is bound to a fluorophore or carrier moiety (or solid support), respectively. Binding of the fluorophore or carrier moiety is effected through reaction of complementary functional groups on the fluorophore, or carrier moiety, and the acceptor-linker or functional moiety, respectively, thereby forming a linkage fragment which joins the two components. Exemplary linkage fragments include: S, SC(O)NH, SC(O)(NH)$_2$, HNC(O)S, SC(O)O, O, NH, NHC(O), (NH)$_2$C(O), (O)CNH and NHC(O)O, and OC(O)NH, CH$_2$S, CH$_2$O, CH$_2$CH$_2$O, CH$_2$CH$_2$S, (CH$_2$)$_o$O, (CH$_2$)$_o$S or (CH$_2$)$_o$Y'-PEG wherein, Y' is S, NH, NHC(O), C(O)NH, NHC(O)O, OC(O)NH, or O and o is an integer from 1 to 50.

The acceptor-linker and functional moiety can be of any useful structure including, but not limited to, acyl, substituted or unsubstituted alkyl, substituted or unsubstituted heteroalkyl, substituted or unsubstituted aryl, substituted or unsubstituted heteroaryl, substituted or unsubstituted heterocycloalkyl, peptide (e.g., a peptide including a protease site), nucleic acid (e.g., hybridization probes, PCR primers), saccharide (e.g., dextran, starch, cyclodextrin). In one preferred embodiment, the linker $L^{11}$ of the functional moiety is long enough to avoid side reactions during synthesis (e.g. intramolecular reactions, such as intra-molecular peptide bond formation), to allow coupling of the compound or complex of the invention to a targeting moiety and to allow the targeting moiety to fulfill its intended function. Useful linkers include those with about 2 to about 50 linear atoms, preferably about 4 to about 20 linear atoms.

In an exemplary embodiment, the acceptor-linker is a nucleic acid and the invention provides a probe based on the nucleic acid. In an example according to this embodiment, an oligonucleotide probe is labeled with a luminescent chelate of the invention as the donor, and an organic fluorophore as the acceptor (reporter) moiety. The nucleic acid probe in a LRET pair can be a simple linear probe, i.e., neither a quencher nor a hairpin structure is necessary.

In one exemplary embodiment, the compounds of the invention are derivatized with a functional moiety. The functional moiety can, for example, be attached to one of the linker units or to one of the building blocks. When two or more functional moieties are used, each can be attached to any of the available linking sites.

The acceptor-linker and/or the functional moiety is preferably attached, so that the resulting functionalized ligand will be able to undergo formation of stable metal ion complexes. In an exemplary embodiment, the macrocyclic ligand is derivatized with a functional moiety. Formula II below shows preferred sites for derivatization with a functional group and/or a acceptor-linker of the chelates of the invention.

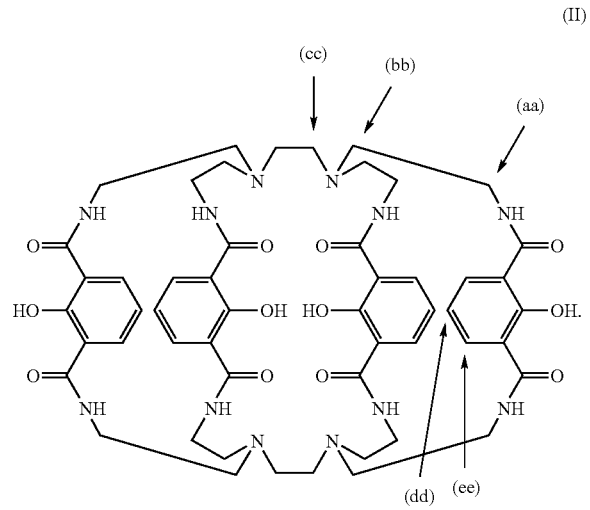 [SMILES: O=C1NCCN2CCNC(=O)c3cccc(c3O)C(=O)NCCN(CCNC(=O)c3cccc1c3O)CCN1CCNC(=O)c3cccc(c3O)C(=O)NCCN(CCNC(=O)c3cccc(c3O)C(=O)NCC1)CC2]

In one exemplary embodiment, a compound according to Formula II is derivatized at position (aa), (bb) or (cc). However, ligands, in which alternative positions within the core structure of the ligand (e.g., positions (dd) and (ee)) are derivatized with a functional moiety and/or a acceptor-linker have similarly useful properties and are encompassed within the instant invention. Those of skill will appreciate that the substitution strategy set forth above is broadly relevant to all compounds according to Formula I, including those compounds set forth hereinbelow.

In an exemplary embodiment, the functional moiety (or acceptor-linker) has the structure:

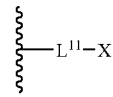

wherein $L^{11}$ is a linker moiety, which is a member selected from substituted or unsubstituted alkyl, substituted or unsubstituted heteroalkyl, substituted or unsubstituted heterocycloalkyl, substituted or unsubstituted aryl and substituted or unsubstituted heteroaryl. X is a reactive functional group, which can be reacted with a carrier moiety (or solid support) or a fluorophore, conjugating this species to the linker through a linkage fragment.

Exemplary ligands that include a functional moiety have the structure:

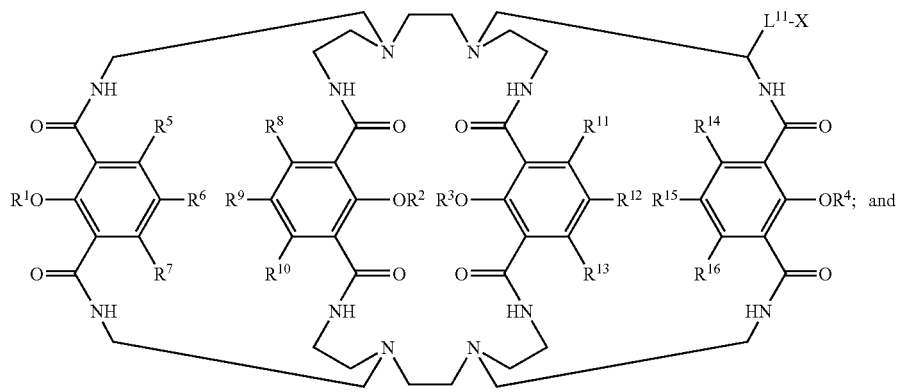

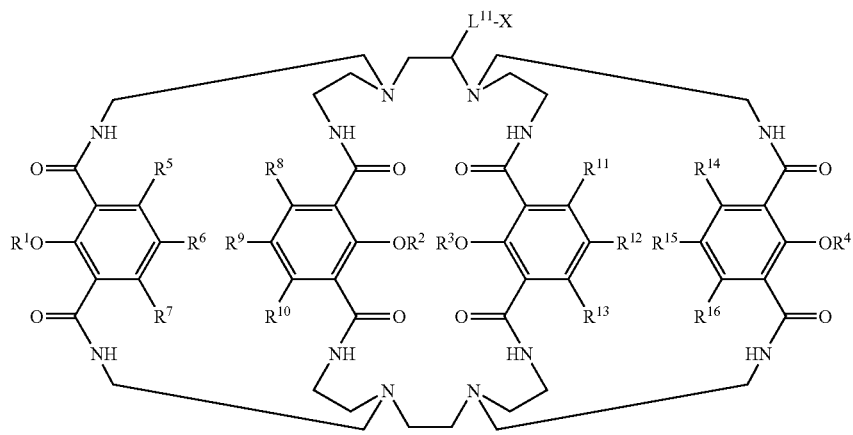

wherein $L^{11}$, X, $R^5$, $R^6$, $R^7$, $R^8$, $R^9$, $R^{10}$, $R^{11}$, $R^{12}$, $R^{13}$, $R^{14}$, $R^{15}$ and $R^{16}$ are as defined above.

In one example, $R^5$ to $R^{16}$ are H. Exemplary ligands have the structure:

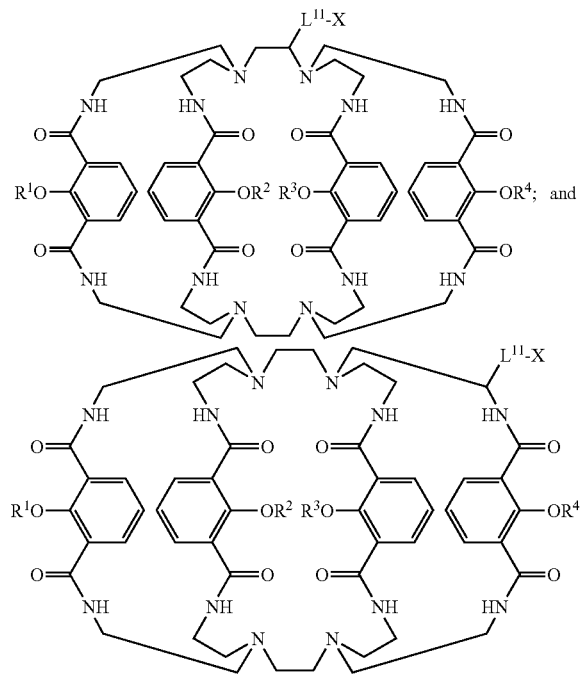

Functionalization of a compound according to Formula II at position (aa) with a $(CH_2)_4NH_2$ group leads to the macrocyclic derivative:

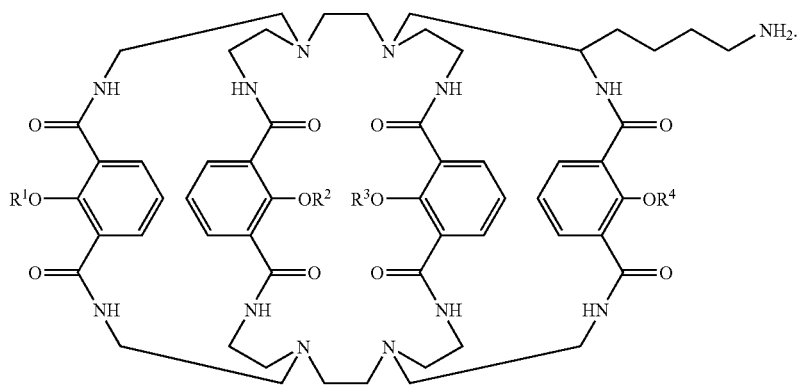

Reactive Functional Groups

In one embodiment, the functional moiety includes a reactive functional group, which can be used to covalently attach the ligand to another species, e.g. a carrier moiety or solid support. Alternatively, the reactive functional group can be used to link the ligand to a nano-particle of any kind Reactive groups and classes of reactions useful in practicing the present invention are generally those that are well known in the art of bioconjugate chemistry. Currently favored classes of reactions available with reactive functional groups of the invention are those which proceed under relatively mild conditions. These include, but are not limited to nucleophilic substitutions (e.g., reactions of amines and alcohols with acyl halides and activated esters), electrophilic substitutions (e.g., enamine reactions) and additions to carbon-carbon and carbon-heteroatom multiple bonds (e.g., Michael reactions and Diels-Alder reactions). These and other useful reactions are discussed, for example, in: March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

a) Amines and Amino-Reactive Groups

In one embodiment, the reactive functional group is a member selected from amines, such as a primary or secondary amine, hydrazines, hydrazides, and sulfonylhydrazides. Amines can, for example, be acylated, alkylated or oxidized. Useful non-limiting examples of amino-reactive groups include N-hydroxysuccinimide (NHS) esters, sulfur-NHS esters, imidoesters, isocyanates, isothiocyanates, acylhalides, arylazides, p-nitrophenyl esters, aldehydes, sulfonyl chlorides and carboxyl groups.

NHS esters and sulfur-NHS esters react preferentially with the primary (including aromatic) amino groups of the reaction partner. The imidazole groups of histidines are known to compete with primary amines for reaction, but the reaction products are unstable and readily hydrolyzed. The reaction involves the nucleophilic attack of an amine on the acid carboxyl of an NHS ester to form an amide, releasing the N-hydroxysuccinimide.

Imidoesters are the most specific acylating reagents for reaction with the amine groups of e.g., a protein. At a pH between 7 and 10, imidoesters react only with primary amines. Primary amines attack imidates nucleophilically to produce an intermediate that breaks down to amidine at high pH or to a new imidate at low pH. The new imidate can react with another primary amine, thus crosslinking two amino groups, a case of a putatively monofunctional imidate reacting bifunctionally. The principal product of reaction with primary amines is an amidine that is a stronger base than the original amine. The positive charge of the original amino group is therefore retained. As a result, imidoesters do not affect the overall charge of the conjugate.

Isocyanates (and isothiocyanates) react with the primary amines of the conjugate components to form stable bonds. Their reactions with sulfhydryl, imidazole, and tyrosyl groups give relatively unstable products.

Acylazides are also used as amino-specific reagents in which nucleophilic amines of the reaction partner attack acidic carboxyl groups under slightly alkaline conditions, e.g. pH 8.5.

Arylhalides such as 1,5-difluoro-2,4-dinitrobenzene react preferentially with the amino groups and tyrosine phenolic groups of the conjugate components, but also with its sulfhydryl and imidazole groups.

p-Nitrophenyl esters of carboxylic acids are also useful amino-reactive groups. Although the reagent specificity is not very high, α- and ε-amino groups appear to react most rapidly.

Aldehydes react with primary amines of the conjugate components (e.g., ε-amino group of lysine residues). Although unstable, Schiff bases are formed upon reaction of the protein amino groups with the aldehyde. Schiff bases, however, are stable, when conjugated to another double bond. The resonant interaction of both double bonds prevents hydrolysis of the Schiff linkage. Furthermore, amines at high local concentrations can attack the ethylenic double bond to form a stable Michael addition product. Alternatively, a stable bond may be formed by reductive amination.

Aromatic sulfonyl chlorides react with a variety of sites of the conjugate components, but reaction with the amino groups is the most important, resulting in a stable sulfonamide linkage.

Free carboxyl groups react with carbodiimides, soluble in both water and organic solvents, forming pseudoureas that can then couple to available amines yielding an amide linkage. Yamada et al., *Biochemistry* 1981, 20: 4836-4842, e.g., teach how to modify a protein with carbodiimides.

b) Sulfhydryl and Sulfhydryl-Reactive Groups

In another embodiment, the reactive functional group is a member selected from a sulfhydryl group (which can be converted to disulfides) and sulfhydryl-reactive groups.

Useful non-limiting examples of sulfhydryl-reactive groups include maleimides, alkyl halides, acyl halides (including bromoacetamide or chloroacetamide), pyridyl disulfides, and thiophthalimides.

Maleimides react preferentially with the sulfhydryl group of the conjugate components to form stable thioether bonds. They also react at a much slower rate with primary amino groups and the imidazole groups of histidines. However, at pH 7 the maleimide group can be considered a sulfhydryl-specific group, since at this pH the reaction rate of simple thiols is 1000-fold greater than that of the corresponding amine.

Alkyl halides react with sulfhydryl groups, sulfides, imidazoles, and amino groups. At neutral to slightly alkaline pH, however, alkyl halides react primarily with sulfhydryl groups to form stable thioether bonds. At higher pH, reaction with amino groups is favored.

Pyridyl disulfides react with free sulfhydryl groups via disulfide exchange to give mixed disulfides. As a result, pyridyl disulfides are relatively specific sulfhydryl-reactive groups.

Thiophthalimides react with free sulfhydryl groups to also form disulfides.

c) Other Reactive Functional Groups

Other exemplary reactive functional groups include:
(a) carboxyl groups and various derivatives thereof including, but not limited to, N-hydroxybenztriazole esters, acid halides, acyl imidazoles, thioesters, p-nitrophenyl esters, alkyl, alkenyl, alkynyl, including succinic and maleic active esters and aromatic esters;
(b) hydroxyl groups, which can be converted to esters, ethers, aldehydes, etc.;
(c) haloalkyl groups, wherein the halide can be displaced with a nucleophilic group such as, for example, an amine, a carboxylate anion, thiol anion, carbanion, or an alkoxide ion, thereby resulting in the covalent attachment of a new group at the site of the halogen atom;
(d) dienophile groups, which are capable of participating in Diels-Alder reactions such as, for example, maleimido groups;
(e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;
(f) alkenes, which can undergo, for example, cycloadditions, acylation, Michael addition, etc;
(g) epoxides, which can react with, for example, amines and hydroxyl groups;
(h) phosphoramidites and other standard functional groups useful in nucleic acid synthesis and
(i) any other functional group useful to form a covalent bond between the functionalized ligand and a molecular entity or a surface.

d) Functional Groups with Non-specific Reactivities

In addition to the use of site-specific reactive moieties, the present invention contemplates the use of non-specific reactive groups to link the ligand to a targeting moiety. Non-specific groups include photoactivatable groups, for example.

Photoactivatable groups are ideally inert in the dark and are converted to reactive species in the presence of light. In one embodiment, photoactivatable groups are selected from precursors of nitrenes generated upon heating or photolysis of azides. Electron-deficient nitrenes are extremely reactive and can react with a variety of chemical bonds including N—H, O—H, C—H, and C=C. Although three types of azides (aryl, alkyl, and acyl derivatives) may be employed, arylazides are presently preferred. The reactivity of arylazides upon photolysis is better with N—H and O—H than C—H bonds. Electron-deficient arylnitrenes rapidly ring-expand to form dehydroazepines, which tend to react with nucleophiles, rather than form C—H insertion products. The reactivity of arylazides can be increased by the presence of electron-withdrawing substituents such as nitro or hydroxyl groups in the ring. Such substituents push the absorption maximum of arylazides to longer wavelength. Unsubstituted arylazides have an absorption maximum in the range of 260-280 nm, while hydroxy and nitroarylazides absorb significant light beyond 305 nm. Therefore, hydroxy and nitroarylazides are most preferable since they allow to employ less harmful photolysis conditions for the affinity component than unsubstituted arylazides.

In another preferred embodiment, photoactivatable groups are selected from fluorinated arylazides. The photolysis products of fluorinated arylazides are arylnitrenes, all of which undergo the characteristic reactions of this group, including C—H bond insertion, with high efficiency (Keana et al., *J. Org. Chem.* 55: 3640-3647, 1990).

In another embodiment, photoactivatable groups are selected from benzophenone residues. Benzophenone reagents generally give higher crosslinking yields than arylazide reagents.

In another embodiment, photoactivatable groups are selected from diazo compounds, which form an electron-deficient carbene upon photolysis. These carbenes undergo a variety of reactions including insertion into C—H bonds, addition to double bonds (including aromatic systems), hydrogen attraction and coordination to nucleophilic centers to give carbon ions.

In still another embodiment, photoactivatable groups are selected from diazopyruvates. For example, the p-nitrophenyl ester of p-nitrophenyl diazopyruvate reacts with aliphatic amines to give diazopyruvic acid amides that undergo ultraviolet photolysis to form aldehydes. The photolyzed diazopyruvate-modified affinity component will react like formaldehyde or glutaraldehyde forming intraprotein crosslinks.

It is well within the abilities of a person skilled in the art to select a reactive functional group, according to the reaction partner. As an example, an activated ester, such as an NHS ester will be useful to label a protein via lysine residues. Sulfhydryl reactive groups, such as maleimides can be used to label proteins via amino acid residues carrying an SH-group (e.g., cystein). Antibodies may be labeled by first oxidizing their carbohydrate moieties (e.g., with periodate) and reacting resulting aldehyde groups with a hydrazine containing ligand.

The reactive functional groups can be chosen such that they do not participate in, or interfere with, the reactions necessary to assemble the reactive ligand. Alternatively, a reactive functional group can be protected from participating in the reaction by means of a protecting group. Those of skill in the art understand how to protect a particular functional group so that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

With respect to each of the functional groups set forth above, when the functional group is on a linker, it is generally preferred that the functional group is located at a terminus of the linker. Thus, it is generally preferred that the functional group on the functional moiety and the acceptor-linker are found at a terminus of the functional moiety and the acceptor-linker, respectively.

Targeting Moieties

Exemplary targeting moieties include carrier molecules as discussed herein; including small-molecule ligands, lipids, linear and cyclic peptides, polypeptides (e.g., EPO, insulin etc.), enzymes, antibodies and receptors. Other targeting moieties include antibody fragments (e.g., those generated to recognize small-molecules and receptor ligands), antigens, nucleic acids (e.g. RNA and cDNA), carbohydrate moieties (e.g., polysaccharides), and pharmacologically active molecules, such as toxins, pharmaceutical drugs and drugs of abuse (e.g. steroids). Additional targeting moieties are selected from solid supports and polymeric surfaces (e.g., polymeric beads and plastic sample reservoirs, such as plastic well-plates), sheets, fibers and membranes. Targeting moieties also include particles (e.g., nano-particles) and drug-delivery vehicles.

In one embodiment, the targeting moiety includes at least one unit of a macrocyclic compound. In an exemplary embodiment, the macrocyclic compound of the targeting moiety has a structure according to Formula (I). In another exemplary embodiment, the compound of the invention has a dendrimeric structure and encompasses several ligands having a structure according to Formula (I). In a further exemplary embodiment, according to this aspect, a complex based on such dendrimer includes at least two metal ions.

In one exemplary embodiment, the targeting moiety is substituted with a luminescence modifying group that allows luminescence energy transfer between a complex of the invention and the luminescence modifying group when the complex is excited.

In another exemplary embodiment, the Linker moiety $L^{11}$ or the targeting moiety include a polyether, such as polyethylene glycol (PEG) and derivatives thereof. In one example, the polyether has a molecular weight between about 50 to about 10,000 daltons.

In further embodiments, the compounds and luminescent complexes of the invention can be used in any assay format aimed at detecting a lipid in a sample (e.g., in the blood of a patient). An exemplary complex according to this embodiment, includes a targeting moiety, which is a protein containing a lipid recognition motif. Exemplary lipid binding proteins include those that bind to phosphatidylinositol, phosphatidylinositol phosphates or other biological lipids.

In another example, the targeting moiety is an antibody that recognizes and binds to an analyte. In an exemplary assay system an analyte may be detected in a sample by first incubating the sample with a complex of the invention, wherein the complex is covalently bound to an antibody that includes a binding site for the analyte. To the mixture can then be added an excess of a probe molecules that binds to the same binding site as the analyte and includes a luminescence modifying group (e.g. an acceptor). The presence and concentration of analyte in the sample is indicated by the luminescence of the assay mixture. For instance, if the concentration of analyte in the sample is high, many of the antibody binding sites will be occupied with the analyte and less binding sites will be available for the probe molecule. In an exemplary embodiment, the analyte is a lipid molecule.

Exemplary Compounds

Exemplary precursors for compounds of the invention include:

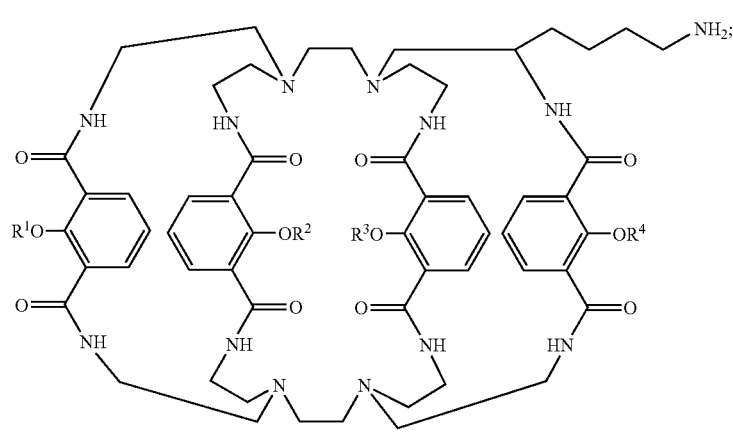

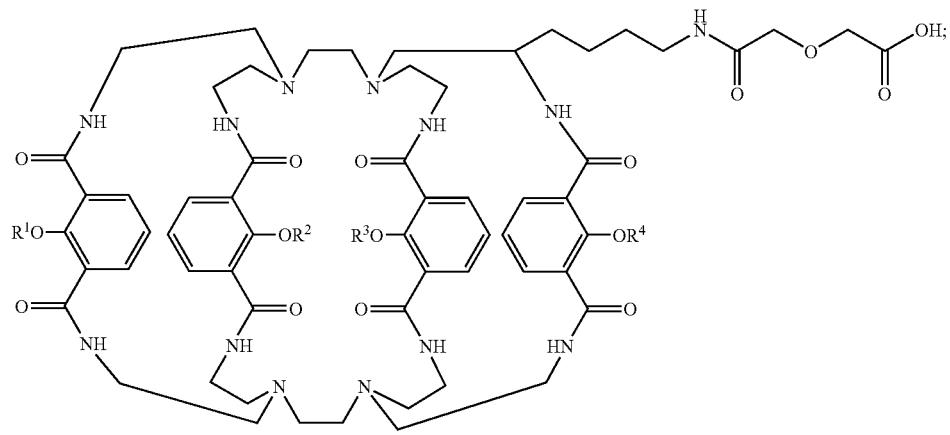
5
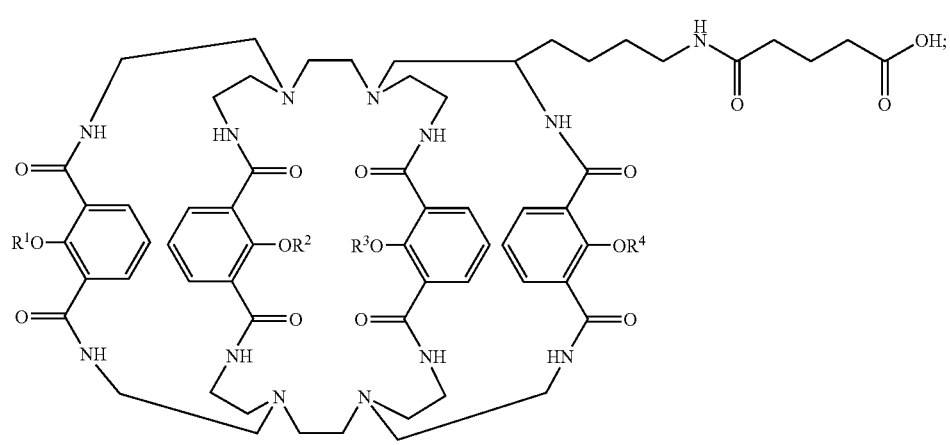
5a
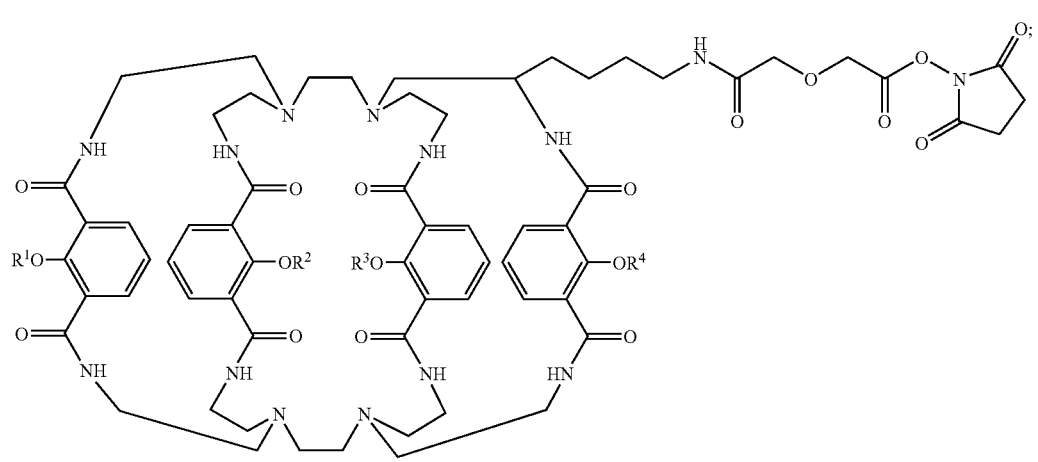
6

-continued
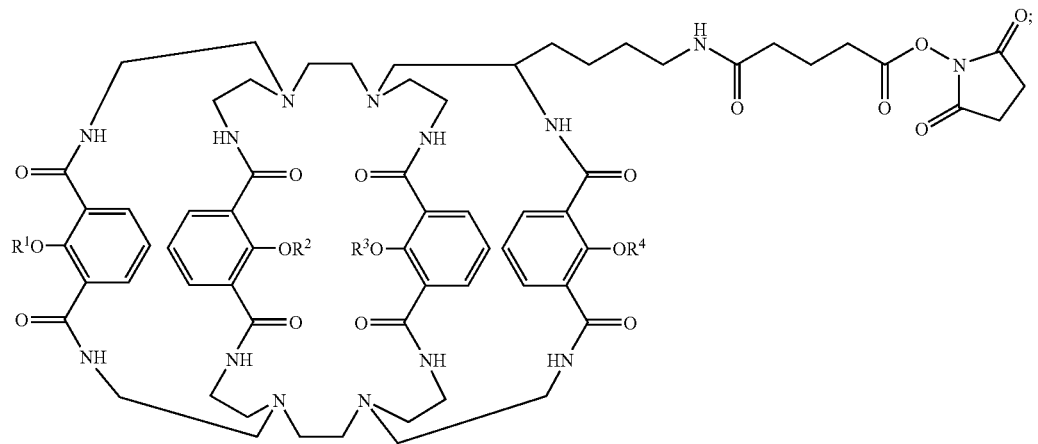
6a
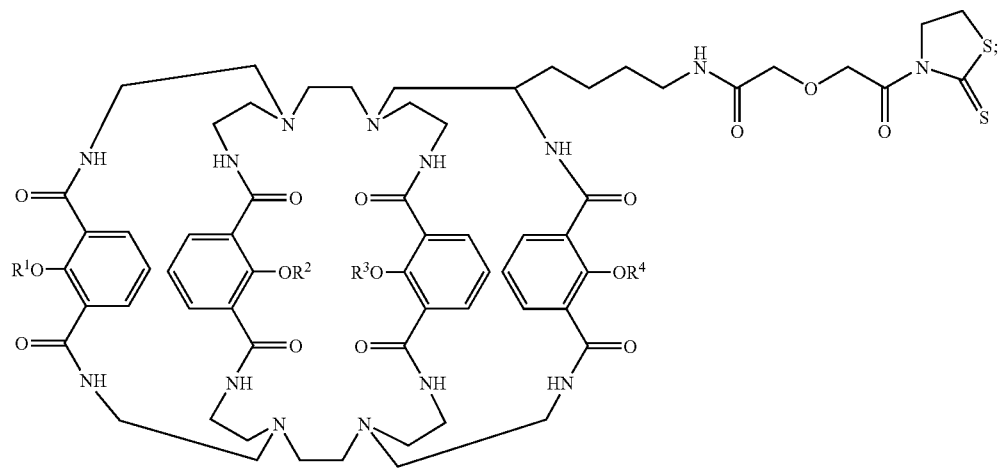
7
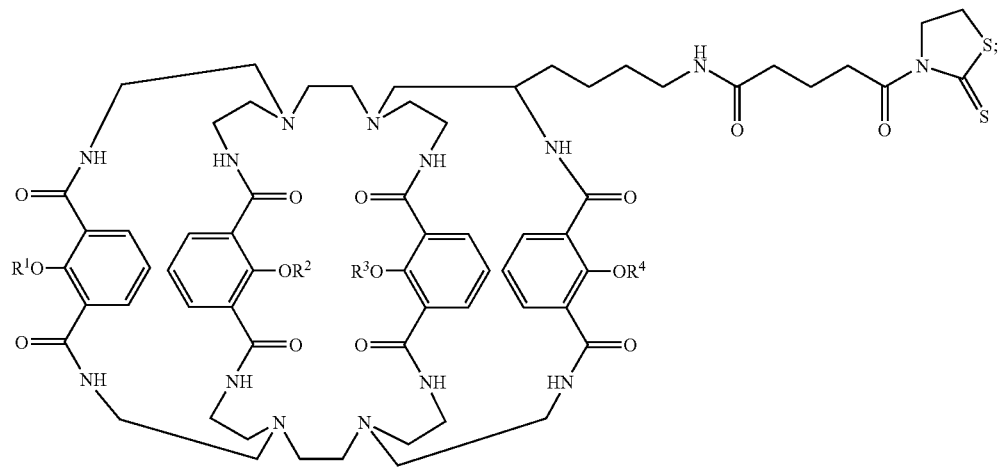
7a

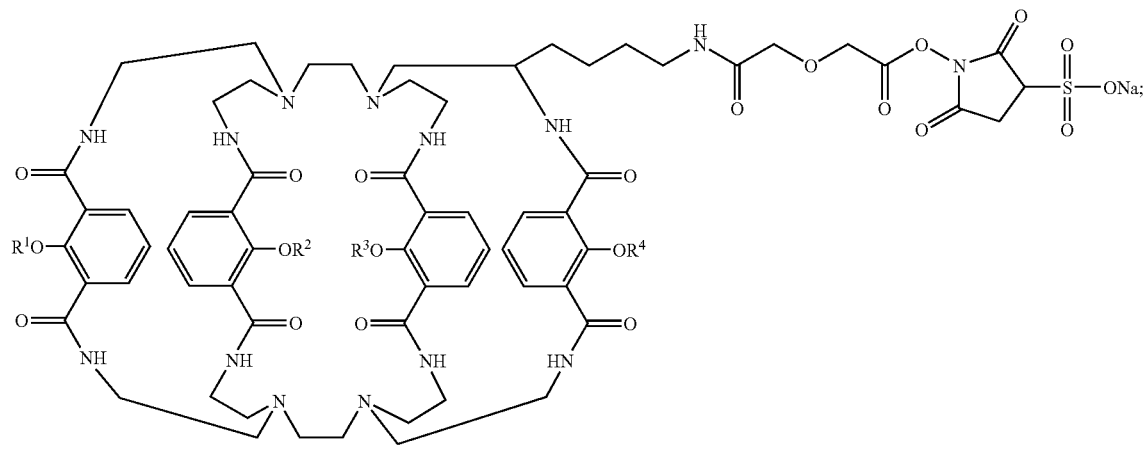
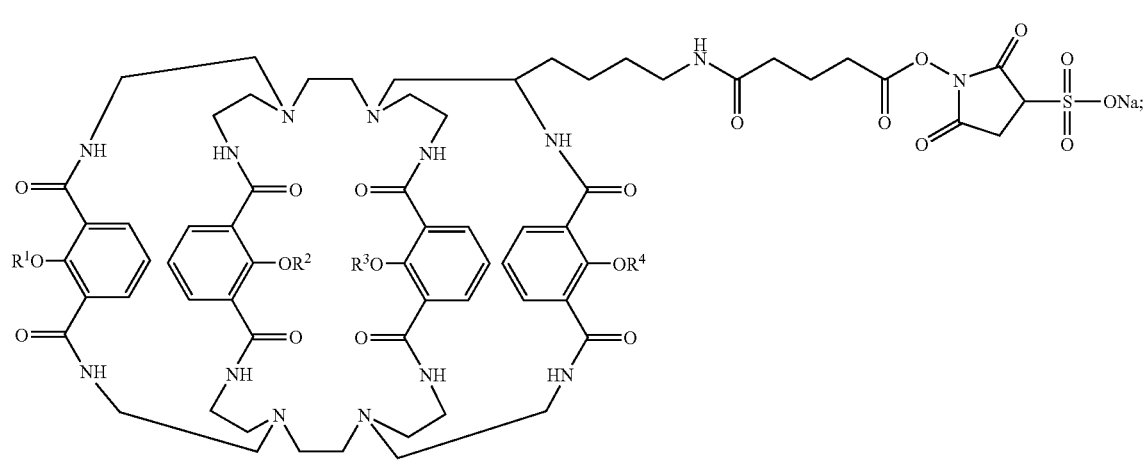
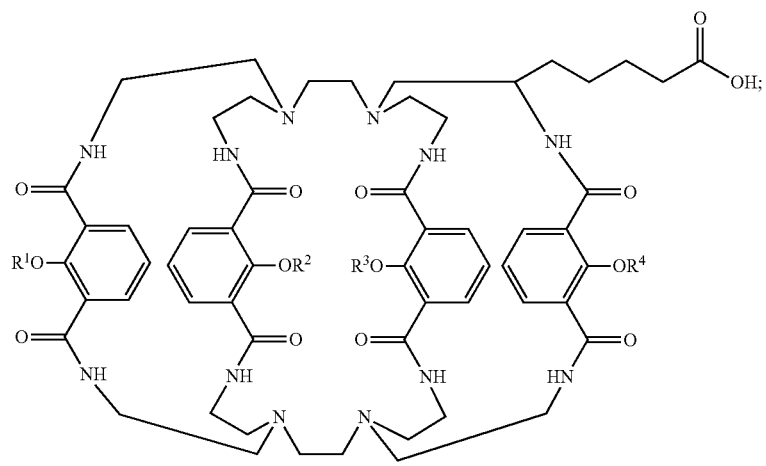

-continued

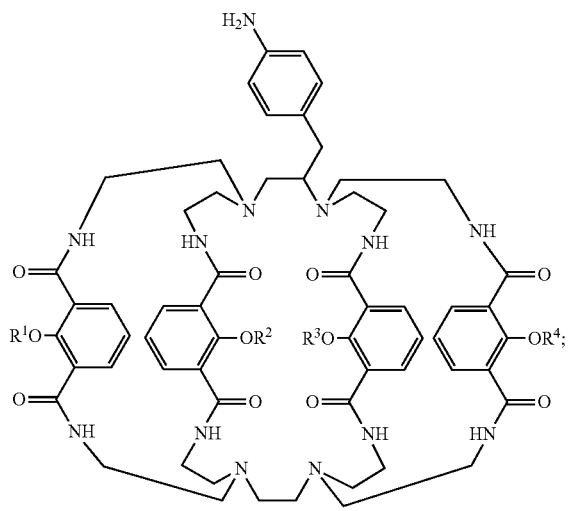

10

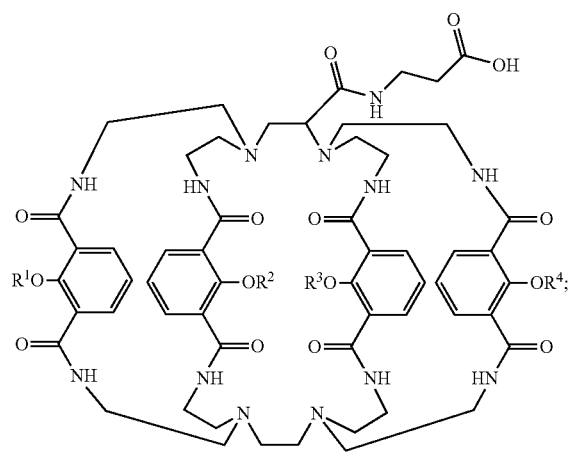

11

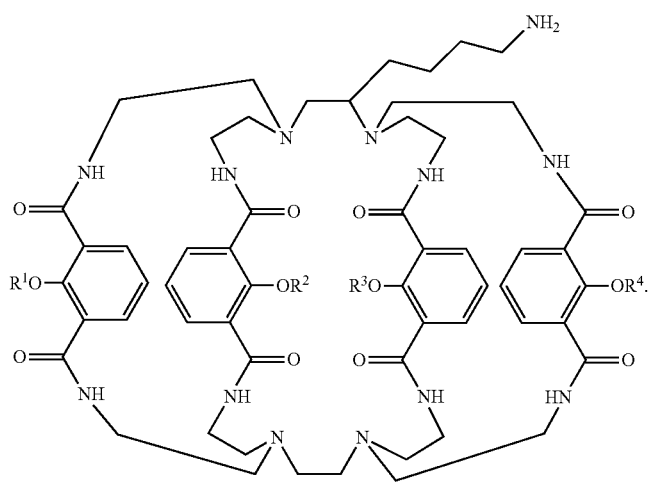

12 wherein $R^1$, $R^2$, $R^3$ and $R^4$ are as defined above. As will be apparent to those of skill in the art, the amines and carboxylic acids of the precursor compounds are readily covalently bound through a linkage fragment to one or more carrier moiety, solid support, or fluorophore.

Complexes

The invention provides complexes formed between at least one metal ion and a compound according to Formula I. Exemplary complexes are luminescent, and the metal ion is chosen according to meeting this criterion. In one exemplary embodiment, the metal is a member selected from the lanthanide group and the complex is preferably luminescent. Exemplary lanthanides include neodynium (Nd), samarium (Sm), europium (Eu), terbium (Tb), dysprosium (Dy) and ytterbium (Yb), of which europium and terbium are presently preferred.

Fluorophore (Donor and Acceptor Moieties)

The luminescent compounds of the invention can be used with a wide range of energy donor and acceptor molecules to construct luminescence energy transfer pairs, e.g., fluorescence energy transfer (FET) probes. Fluorophores useful in conjunction with the complexes of the invention are known to those of skill in the art. See, for example, Cardullo et al., *Proc. Natl. Acad. Sci. USA* 85: 8790-8794 (1988); Dexter, D. L., *J. of Chemical Physics* 21: 836-850 (1953); Hochstrasser et al., *Biophysical Chemistry* 45: 133-141 (1992); Selvin, P., *Methods in Enzymology* 246: 300-334 (1995); Steinberg, I. *Ann. Rev. Biochem.*, 40: 83-114 (1971); Stryer, L. *Ann. Rev. Biochem.*, 47: 819-846 (1978); Wang et al., *Tetrahedron Letters* 31: 6493-6496 (1990); Wang et al., *Anal. Chem.* 67: 1197-1203 (1995).

There is practical guidance available in the literature for selecting appropriate donor-acceptor pairs for particular probes, as exemplified by the following references: Pesce et al., Eds., FLUORESCENCE SPECTROSCOPY (Marcel Dekker, New York, 1971); White et al., FLUORESCENCE ANALYSIS: A PRACTICAL APPROACH (Marcel Dekker, New York, 1970). The literature also includes references providing exhaustive lists of fluorescent and chromogenic molecules and their relevant optical properties, for choosing reporter-quencher pairs (see, for example, Berlman, HANDBOOK OF FLUORESCENCE SPECTRA OF AROMATIC MOLECULES, 2nd Edition (Academic Press, New York, 1971); Griffiths, COLOUR AND CONSTITUTION OF ORGANIC MOLECULES (Academic Press, New York, 1976); Bishop, Ed., INDICATORS (Pergamon Press, Oxford, 1972); Haugland, HANDBOOK OF FLUORESCENT PROBES AND RESEARCH CHEMICALS (Molecular Probes, Eugene, 1992) Pringsheim, FLUORESCENCE AND PHOSPHORESCENCE (Interscience Publishers, New York, 1949);

and the like. Further, there is extensive guidance in the literature for derivatizing reporter and quencher molecules for covalent attachment via readily available reactive groups that can be added to a molecule.

The diversity and utility of chemistries available for conjugating fluorophores to other molecules and surfaces is exemplified by the extensive body of literature on preparing nucleic acids derivatized with fluorophores. See, for example, Haugland (supra); Ullman et al., U.S. Pat. No. 3,996,345; Khanna et al., U.S. Pat. No. 4,351,760. Thus, it is well within the abilities of those of skill in the art to choose an energy exchange pair for a particular application and to conjugate the members of this pair to a probe molecule, such as, for example, a small molecular bioactive material, nucleic acid, peptide or other polymer.

In a FRET pair, it is generally preferred that an absorbance band of the acceptor substantially overlap a fluorescence emission band of the donor. When the donor (fluorophore) is a component of a probe that utilizes fluorescence resonance energy transfer (FRET), the donor fluorescent moiety and the quencher (acceptor) of the invention are preferably selected so that the donor and acceptor moieties exhibit fluorescence resonance energy transfer when the donor moiety is excited. One factor to be considered in choosing the fluorophore-quencher pair is the efficiency of fluorescence resonance energy transfer between them. Preferably, the efficiency of FRET between the donor and acceptor moieties is at least 10%, more preferably at least 50% and even more preferably at least 80%. The efficiency of FRET can easily be empirically tested using the methods both described herein and known in the art.

The efficiency of FRET between the donor-acceptor pair can also be adjusted by changing ability of the donor and acceptor to dimerize or closely associate. If the donor and acceptor moieties are known or determined to closely associate, an increase or decrease in association can be promoted by adjusting the length of a linker moiety, or of the probe itself, between the two fluorescent entities. The ability of donor-acceptor pair to associate can be increased or decreased by tuning the hydrophobic or ionic interactions, or the steric repulsions in the probe construct. Thus, intramolecular interactions responsible for the association of the donor-acceptor pair can be enhanced or attenuated. Thus, for example, the association between the donor-acceptor pair can be increased by, for example, utilizing a donor bearing an overall negative charge and an acceptor with an overall positive charge.

In addition to fluorophores that are attached directly to a probe, the fluorophores can also be attached by indirect means. In this embodiment, a ligand molecule (e.g., biotin) is preferably covalently bound to the probe species. The ligand then binds to another molecules (e.g., streptavidin) molecule, which is either inherently detectable or covalently bound to a signal system, such as a fluorescent compound of the invention, or an enzyme that produces a fluorescent compound by conversion of a non-fluorescent compound. Useful enzymes of interest as labels include, for example, hydrolases, particularly phosphatases, esterases and glycosidases, or oxidotases, particularly peroxidases. Fluorescent compounds include fluorescein and its derivatives, rhodamine and its derivatives, dansyl, umbelliferone, etc., as discussed above. For a review of various labeling or signal producing systems that can be used, see, U.S. Pat. No. 4,391,904.

A non-limiting list of exemplary donor or acceptor moieties that can be used in conjunction with the luminescent complexes of the invention, is provided in Table 1.

TABLE 1

Suitable Moieties Useful
as Acceptors in FRET Pairs 4-acetamido-4'-isothiocyanatostilbene-2,2'disulfonic acid
acridine and derivatives:
    acridine
    acridine isothiocyanate
5-(2'-aminoethyl)aminonaphthalene-1-sulfonic acid (EDANS)
4-amino-N-[3-vinylsulfonyl)phenyl]naphthalimide-3,5 disulfonate
N-(4-anilino-1-naphthyl)maleimide
anthranilamide
BODIPY
Brilliant Yellow
coumarin and derivatives:
coumarin
    7-amino-4-methylcoumarin (AMC, Coumarin 120)
    7-amino-4-trifluoromethylcouluarin (Coumaran 151)
cyanine dyes
cyanosine
4',6-diaminidino-2-phenylindole (DAPI)
5',5''-dibromopyrogallol-sulfonaphthalein (Bromopyrogallol Red)
7-diethylamino-3-(4'-isothiocyanatophenyl)-4-methylcoumarin
diethylenetriamine pentaacetate
4,4'-diisothiocyanatodihydro-stilbene-2,2'-disulfonic acid
4,4'-diisothiocyanatostilbene-2,2'-disulfonic acid
5-[dimethylamino]naphthalene-1-sulfonyl chloride (DNS, dansylchloride)
4-(4'-dimethylaminophenylazo)benzoic acid (DABCYL)
4-dimethylaminophenylazophenyl-4'-isothiocyanate (DABITC)
eosin and derivatives:
    eosin
    eosin isothiocyanate
erythrosin and derivatives:
    erythrosin B
    erythrosin isothiocyanate
ethidium
fluorescein and derivatives:
    5-carboxyfluorescein (FAM)
    5-(4,6-dichlorotriazin-2-yl)aminofluorescein (DTAF)
    2',7'-dimethoxy-4'5'-dichloro-6-carboxyfluorescein (JOE)
    fluorescein
    fluorescein isothiocyanate
    QFITC (XRITC)
fluorescamine
IR144
IR1446
Suitable Moieties Useful
as Donors or Acceptors in FRET Pairs Malachite Green isothiocyanate
4-methylumbelliferone
ortho cresolphthalein
nitrotyrosine
pararosaniline
Phenol Red
B-phycoerythrin
o-phthaldialdehyde
pyrene and derivatives:
    pyrene
    pyrene butyrate
    succinimidyl 1-pyrene butyrate
quantum dots
Reactive Red 4 (Cibacron ™ Brilliant Red 3B-A)
rhodamine and derivatives:
    6-carboxy-X-rhodamine (ROX)
    6-carboxyrhodamine (R6G)
    lissamine rhodamine B sulfonyl chloride rhodamine (Rhod)
    rhodamine B
    rhodamine 123
rhodamine X isothiocyanate
    sulforhodamine B
    sulforhodamine 101
sulfonyl chloride derivative of sulforhodamine 101 (Texas Red)
N,N,N',N'-tetramethyl-6-carboxyrhodamine (TAMRA)
tetramethyl rhodamine
    tetramethyl rhodamine isothiocyanate (TRITC)
riboflavin
rosolic acid
lanthanide chelate derivatives Structures of exemplary functionalized fluorophores of use in the compounds of the invention are set forth in FIG. 1. Similar derivatization strategies for each of the fluorophores set forth in Tables 1-3 are available and applicable to the invention.

Exemplary commercially available acceptors are listed in Table 2 including protein based acceptors and quenchers.

TABLE 2

Exemplary fluorophores

| Acceptor Name | Excitation (nm) | Emission (nm) |
|---|---|---|
| Fluorescein (FITC, FAM) | 494 | 518 |
| Eosin | 524 | |
| TET | 525 | 540 |
| HEX; JOE; VIC; CAL Fluor Orange 560 | 535 | 555 |
| ROX (5/6-carboxy Rhodamine); LC Red 610; Cal Fluor Red 610 | 575 | 605 |
| Rhodamine 101 | 496 | 520 |
| Rhodamine Red | 570 | |
| Texas Red; LC Red 610; CAL Fluor Red 610 | 590 | 610 |
| Cy2 | 489 | 506 |
| Cy3; NED; Quasar 570; Oyster 556 | 550 | 570 |
| Cy5; LC Red 670; Quasar 670; Oyster 645 | 649 | 670 |
| Malachite Green | 630 | |
| Tetramethyl Rhodamine (TAMRA, TMR, TRITC) | 555 | 580 |
| Acridine orange | 500 | 530 |
| Bodipy 530/550 | 534 | 554 |
| BODIPY TR-X | 588 | 616 |
| LC Red 640; Cal Fluor Red 635 | 625 | 640 |
| Nile Red | 485 | 525 |
| Oregon Green 488 | 493 | 520 |
| YOYO-1 | 491 | 509 |
| YOYO-2 | 612 | 631 |
| Ca-Green | 506 | 534 |
| Ca-Orange | 555 | 576 |
| Ca-Crimson | 588 | 610 |
| Mg-Green | 506 | 532 |
| Na-Green | 507 | 532 |
| Oxonol V | 610 | 639 |

PROTEIN FLUOROPHORES

| Acceptor Name | Excitation (nm) | Emission (nm) |
|---|---|---|
| EGFP | 489 | 508 |
| dsRED | 558 | 583 |
| B-Phycoerythrin | 546, 565 | 575 |
| R-Phycoerythrin | 480, 546, 565 | 578 |
| allophycocyanin | 650 | 660 |

FRET QUENCHERS

| Quencher Name | $\epsilon$ (cm$^{-1}$M$^{-1}$) | Absorption Max (nm) |
|---|---|---|
| QSY 7 | 90,000 | 570 |
| QSY-9 | 88,000 | 562 |
| QSY-35 | 23,000 | 475 |
| BHQ-1 | | 535 |
| BHQ-2 | | 580 |
| DDQ-I | | 430 |
| Dabcyl | | 475 |
| Eclipse | | 530 |
| Iowa Black FQ | | 532 |
| DDQ-II | | 630 |
| Iowa Black RQ | | 645 |

In one embodiment, the fluorophore is a member of the Alexa Fluor family, such as those set forth in Table 3.

TABLE 3

Alexa Fluor ® as Exemplary Acceptor Fluorophores for 4-Tb Donor.

| | Color[1] | Ex (nm) | Em (nm) | MW (g/mol) | $\epsilon$ (cm$^{-1}$M$^{-1}$) |
|---|---|---|---|---|---|
| Alexa Fluor 350 | blue | 346 | 442 | 410 | 19,000 |
| Alexa Fluor 405 | violet | 401 | 421 | 1028 | 34,000 |
| Alexa Fluor 430 | green | 434 | 541 | 702 | 16,000 |
| Alexa Fluor 488 | green | 495 | 519 | 643 | 71,000 |
| Alexa Fluor 500 | green | 502 | 525 | 700 | 71,000 |
| Alexa Fluor 514 | green | 517 | 542 | 714 | 80,000 |
| Alexa Fluor 532 | green | 532 | 554 | 721 | 81,000 |
| Alexa Fluor 546 | yellow-green | 556 | 573 | 1079 | 104,000 |
| Alexa Fluor 555 | green | 555 | 565 | ~1250 | 150,000 |
| Alexa Fluor 568 | orange | 578 | 603 | 792 | 91,300 |
| Alexa Fluor 594 | orange-red | 590 | 617 | 820 | 90,000 |
| Alexa Fluor 610 | red | 612 | 628 | 1172 | 138,000 |
| Alexa Fluor 633 | not vis | 632 | 647 | ~1200 | 100,000 |
| Alexa Fluor 647 | not vis | 650 | 665 | ~1300 | 239,000 |
| Alexa Fluor 660 | not vis | 663 | 690 | ~1100 | 132,000 |
| Alexa Fluor 680 | not vis | 679 | 702 | ~1150 | 184,000 |
| Alexa Fluor 700 | not vis | 702 | 723 | ~1400 | 192,000 |
| Alexa Fluor 750 | not vis | 749 | 775 | ~1300 | 240,000 |

[1]Approximate color of the emission spectrum.
$\epsilon$ = extinction coefficient Presently preferred Alexa Fluor fluorophores include 488, 500, 532, 546, 555, 568, 594, 610 and 633.

Means of detecting fluorescent labels are well known to those of skill in the art. Thus, for example, fluorescent labels can be detected by exciting the fluorophore with the appropriate wavelength of light and detecting the resulting fluorescence. The fluorescence can be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product.

Methods

The compounds and complexes of the invention are useful as probes in a variety of biological assay systems and diagnostic applications. An overview of assay systems, such as competitive assay formats, immunological assays, microarrays, membrane binding assays and enzyme activity assays, is given e.g., in U.S. Pat. No. 6,864,103 to Raymond et al., which is incorporated herein in its entirety for all purposes. It is within the ability of one of skill in the art to select and prepare a probe that includes a complex of the invention, and which is suitable for each assay system. In an exemplary embodiment, the luminescent probe molecule is used to detect the presence or absence of an analyte in a sample.

Figure 9:
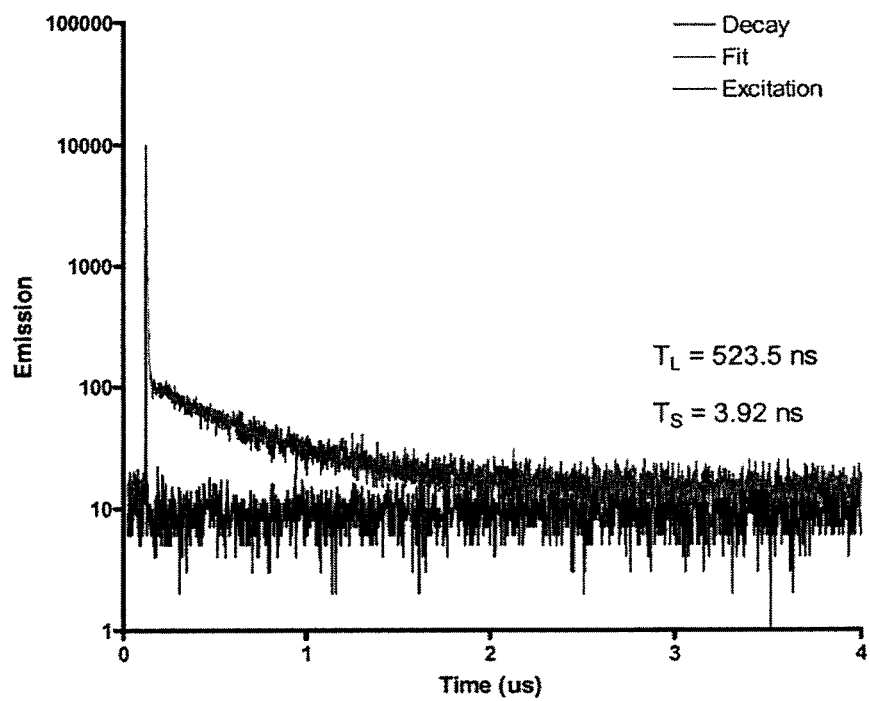
FIG. 9 shows the lifetime decay of FITC-Tb-BH22IAM conjugate. Decay data fitting to biexponential revealed two apparent lifetimes. A short lifetime corresponding to the direct excitation of fluorescein (3.92 nsec) and a long lifetime corresponding to excitation of BH22IAM and energy transfer to fluorescein (524 nsec).

In an exemplary embodiment, the complex according to Formula I is utilized in a procedure wherein emission from the complex excites at least one fluorophore in an assay. In another exemplary embodiment, emission from the complex excites at least two fluorophores in an assay, such that each fluorophore emits light of a characteristic wavelength and lifetime. In this example, each of the at least two fluorophores is distinguishable from the other on the basis of emission wavelength and/or lifetime. See, for example, FIG. 9, and Chen et al., J. Am. Chem. Soc., 122: 657-660 (2000). In a preferred embodiment, the complex of the invention distinguishably excites at least 2, 3, 4, 5, 6, 7, 8, 9 or at least 10 fluorophores essentially simultaneously.

The disclosed lanthanide complexes have particular utility in assays that are intended to detect or quantify binding or other modification of an assay component. These assays may incorporate one or more steps, including (a) contacting at least one member of a plurality of molecules with a binding partner capable of binding one of the molecules, (b) detecting a response indicative of the extent of binding between the at least one member of the plurality and the binding partner, and (c) correlating the response with the extent of binding or modification, or with a the activity of an enzyme that affects the modification. In some embodiments, the assays may include repeating the steps of contacting, detecting, and/or correlating for the same sample and/or a plurality of different samples. The assays may also involve providing a sample holder having a plurality of sample sites containing or supporting a corresponding plurality of samples, and sequentially and/or simultaneously repeating the steps of contacting, detecting, and/or correlating for the plurality of samples. The remainder of this section describes in more detail the steps of (a) contacting, (b) detecting, and (c) correlating.

The step of contacting assay components such as binding partners (e.g., nucleic acids, peptides, enzymes, enzyme modulators, substrates, products) with one another and/or with other species generally comprises any method for bringing any specified combination of these components into functional and/or reactive contact. A preferred method is by mixing and/or forming the materials in solution, although other methods, such as attaching one or more components (e.g., a complex according to Formula I, a species comprising a complex according to Formula I or other assay component) to a bead or surface, also may be used, as long as the components retain at least some function, specificity, and/or binding affinity following such attachment. The assay may be carried out in a device for manipulating fluids. Useful assay apparati having fluidics capability (e.g., microfluidics) suitable for contacting or otherwise preparing assay components are generally known in the art.

One or more of the assay components may comprise a sample, which typically takes the form of a solution containing one or more analyte that are biological and/or synthetic in origin. The sample may be a biological sample that is prepared from a blood sample, a urine sample, a swipe, or a smear, among others. Alternatively, the sample may be an environmental sample that is prepared from an air sample, a water sample, or a soil sample, among others. The sample typically is aqueous but may contain compatible organic solvents, buffering agents, inorganic salts, and/or other components known in the art for assay solutions.

The assay components and/or sample may be supported for contact and/or detection and/or analysis by any substrate or material capable of providing such support. Suitable substrates may include microplates, PCR plates, biochips, and hybridization chambers, among others, where features such as microplate wells and microarray (i.e., biochip) sites may comprise assay sites. Microplates may include 96, 384, 1536, or other numbers of wells. These microplates also may include wells having small (≈50 μL) volumes, elevated bottoms, and/or frusto-conical shapes capable of matching a sensed volume. Suitable PCR plates may include the same (or a similar) footprint, well spacing, and well shape as the preferred microplates, while possessing stiffness adequate for automated handling and thermal stability adequate for PCR. Suitable microarrays include nucleic acid and polypeptide microarrays, which are generally known in the art.

The step of detecting a response indicative of the extent of binding or modification generally comprises any method for effectuating such detection, including detecting and/or quantifying a change in, or an occurrence of, a suitable parameter and/or signal. The method may include luminescence and/or nonluminescence methods, and heterogeneous and/or homogeneous methods, among others.

Luminescence and nonluminescence methods may be distinguished by whether they involve detection of light emitted by a component of the sample. Luminescence assays involve detecting light emitted by a luminescent compound (or luminophore) and using properties of that light to understand properties of the compound and its environment. A typical luminescence assay may involve (1) exposing a sample to a condition capable of inducing luminescence from the sample, and (2) measuring a detectable luminescence response indicative of the extent of binding between the member of interest and a corresponding binding partner. Suitable luminescence assays include, among others, (1) luminescence intensity, which involves detection of the intensity of luminescence, (2) luminescence polarization, which involves detection of the polarization of light emitted in response to excitation by polarized light, (3) luminescence energy transfer, and (4) luminescence lifetime. A single assay mixture may be analyzed by one or more of these techniques. In a preferred embodiment, energy exchange between a luminescent complex of the invention and a fluorophore is utilized to detect the analyte (and optionally its degree of modification or binding to a binding partner) is utilized to determine both the emission wavelength and excitation lifetime of one or more fluorophores.

The detectable luminescence response generally comprises a change in, or an occurrence of, a luminescence signal that is detectable by direct visual observation and/or by suitable instrumentation. Typically, the detectable response is a change in a property of the luminescence, such as a change in the intensity, polarization, energy transfer, lifetime, and/or excitation or emission wavelength distribution of the luminescence. For example, energy transfer may be measured as a decrease in donor luminescence, an increase (often from zero) in acceptor luminescence, and/or a decrease in donor luminescence lifetime, among others. The detectable response may be simply detected, or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence assays, the detectable response may be generated directly using a donor or acceptor associated with an assay component actually involved in binding, or indirectly using a donor or acceptor associated with another (e.g., reporter or indicator) component. Suitable methods and donors and acceptors for luminescently labeling assay components are described in the following materials, which are incorporated herein by reference: Richard P. Haugland, Handbook of Fluorescent Probes and Research Chemicals (6th ed. 1996).

Heterogeneous and homogeneous methods may be distinguished by whether they involve sample separation before detection. Heterogeneous methods generally require bulk separation of bound and unbound species. This separation may be accomplished, for example, by washing away any unbound species following capture of the bound species on a solid phase, such as a bead or microplate surface labeled with a trivalent metal or other suitable binding partner. Such metals may include gallium (Ga, including Ga(III)), iron (Fe), aluminum (Al), and/or zinc (Zn), among others. Suitable metals and other binding partners are described in more detail in U.S. patent application Ser. No. 10/746,797, filed Dec. 23, 2003, which is incorporated herein by reference. The extent of binding then can be determined directly by measuring the amount of captured bound species and/or indirectly by measuring the amount of uncaptured unbound species (if the total amount is known). Homogeneous methods, in contrast, generally do not require bulk separation but instead require a detectable response such as a luminescence response that is affected in some way by binding or unbinding of bound and unbound species without separating the bound and unbound species. Alternatively, or in addition, enzyme activity may result in increased or decreased energy transfer between a donor and acceptor of an energy transfer pair, based on whether the acceptor quenches or not, and based on whether enzyme activity in the assay results in increased or decreased proximity of the donor and acceptor. Homogeneous assays typically are simpler to perform but more complicated to develop than heterogeneous assays.

The step of correlating generally comprises any method for correlating the extent of binding with the extent of modification of the assay component being analyzed, and/or with the presence and/or activity of an enzyme that affects the modification. The nature of this step depends in part on whether the detectable response is simply detected or whether it is quantified. If the response is simply detected, it typically will be used to evaluate the presence of a component such as a substrate, product, and/or enzyme, or the presence of an activity such as an enzyme or modulator activity. In contrast, if the response is quantified, it typically will be used to evaluate the presence and/or quantity of a component such as a substrate, product, and/or enzyme, or the presence and/or activity of a component such as an enzyme or modulator.

The correlation generally may be performed by comparing the presence and/or magnitude of the response to another response (e.g., derived from a similar measurement of the same sample at a different time and/or another sample at any time) and/or a calibration standard (e.g., derived from a calibration curve, a calculation of an expected response, and/or a luminescent reference material). Thus, for example, in a energy transfer assay for cyclic nucleotide concentration, the cyclic nucleotide concentration in an unknown sample may be determined by matching the energy transfer efficiency measured for the unknown with the cyclic nucleotide concentration corresponding to that efficiency in a calibration curve generated under similar conditions by measuring energy transfer efficiency as a function of cyclic nucleotide concentration.

Thus, in one aspect, the invention provides a mixture of a complex of the invention and an analyte.

In another aspect, the invention provides a method of detecting the presence or absence of an analyte in a sample. The method comprises (a) contacting the sample and a composition including a complex of the invention; (b) exciting the complex; and (c) detecting luminescence from the complex. The presence or absence of the analyte can be indicated by the absence or presence of luminescence from the complex.

In a further aspect, the invention provides a method of detecting the presence or absence of an analyte in a sample. The method comprises (a) contacting the sample and a composition comprising a complex of the invention, and a luminescence modifying group, wherein energy can be transferred between the complex and the luminescence modifying group when the complex is excited, and wherein the complex and the luminescence modifying group can be part of the same molecule or be part of different molecules; and (b) exciting said complex; and (c) determining the luminescent property of the sample, wherein the presence or absence of the analyte is indicated by the luminescent property of the sample.

In an exemplary embodiment, the analyte, if present in said sample, competes with a probe molecule that includes a complex of the invention, for binding to a binding site located on a recognition molecule. In another exemplary embodiment, the analyte displaces the probe molecule from the binding site located on a recognition molecule, by binding to the binding site. In a further exemplary embodiment, the probe molecule is a complex of the invention.

In an alternative embodiment, the invention provides a first nucleic acid probe that hybridizes to a first nucleic acid target sequence on the subject nucleic acid, and incorporates a luminescence resonance energy transfer lanthanide chelate donor moiety; and second nucleic acid probe that hybridizes to a second nucleic acid target sequence on the subject nucleic acid, and incorporates an organic resonance energy transfer acceptor moiety, wherein the first nucleic acid target sequence and the second nucleic acid target sequence are separated by a number of nucleotides on the subject nucleic acid such that a luminescence resonance energy transfer signal from interaction between the lanthanide chelate donor moiety of the first nucleic acid probe and the acceptor moiety of the second nucleic acid probe can be detected to determine hybridization of both the first nucleic acid probe and the second nucleic acid probe to the subject nucleic acid. In certain embodiments of this invention, the first nucleic acid probe or second nucleic acid probe is linear or randomly coiled when not hybridized to the first or second nucleic acid target sequences, respectively. In other embodiments of this invention, the first nucleic acid probe or second nucleic acid probe forms a stem-loop structure when not hybridized to the first or second nucleic acid target sequences, respectively.

In certain preferred embodiments of the invention, the first nucleic acid probe further incorporates a quencher moiety, such that an interaction between the donor moiety of the first nucleic acid probe and the quencher moiety can be detected to differentiate between the first nucleic acid probe in the stem-loop structure and non-stem-loop structure. Similarly, in other embodiments, the second nucleic acid probe further incorporates a quencher moiety, such that an interaction between the acceptor moiety of the second nucleic acid probe and the quencher moiety can be detected to differentiate between the second nucleic acid probe in the stem-loop structure and non-stem-loop structure. In embodiments utilizing a quencher moiety on a nucleic acid probe, the invention provides that the quencher moiety can be selected from, for example, dabcyl quencher, black hole quencher or Iowa Black quencher or other moieties well-known in the art to change the resonance energy transfer wavelength emission of an unquenched donor or acceptor moiety.

In certain other embodiments, the first nucleic acid probe further incorporates a resonance energy transfer moiety pair, such that a resonance energy transfer signal from interaction between the donor moiety and the acceptor moiety on the first nucleic acid probe can be detected to differentiate between the first nucleic acid probe in the stem-loop structure and non-stem-loop structure. Similarly, other embodiments provide that the second nucleic acid probe further incorporates a resonance energy transfer moiety pair, such that a resonance energy transfer signal from interaction between the donor moiety and the acceptor moiety on the second nucleic acid probe can be detected to differentiate between the second nucleic acid probe in the stem-loop structure and non-stem-loop structure.

In additional embodiments, the invention provides methods for detecting a subject nucleic acid, comprising combining the composition described herein with a sample suspected of containing a subject nucleic acid, and detecting hybridization by differential resonance energy transfer signal to determine the presence or absence, and/or the expression level of the subject nucleic acid in the sample in vitro or in vivo. In some preferred embodiments, the methods can be performed in vivo. Therefore, in a preferred embodiment of this method, the sample contains a living cell. The invention provides that the methods may be performed with samples comprising living tissues and cells that are taken out of the body, or that remain in situ.

The methods of the present invention further include detection of changes in the levels of expression of a nucleic acid target, or in RNA transcript, such that alterations of gene expression can be monitored as a result of the dose-dependent cellular response to external stimuli, such as drug molecules, hormones, growth factors, temperature, shear flow, or microgravity, for example. The invention further provides that the compositions can be used to visualize, i.e., through fluorescence or luminescence, the location and relative amount of gene expression in tissues and cells.

In diagnostic or prognostic detection methods the subject nucleic acid can comprise a genetic point mutation, deletion, or insertion relative to a naturally occurring or control nucleic acid. Such screening methods can permit the detection of the subject nucleic acid indicating the presence of a genetically associated disease, such as certain cancers, in the sample. There are many well-known examples of genetic mutations already in the art that are indicative of a disease state. The methods include the detection of nucleic acids comprising K-ras, survivin, p53, p16, DPC4, or BRCA2. Furthermore, the methods can be used to detect the amount of a subject nucleic acid being produced by an organism for purposes other than diagnosis or prognosis of a disease or condition. Resonance energy transfer detections of the present invention can be performed with the assistance of single- or multiple-photon microscopy, time-resolved fluorescence microscopy or fluorescence endoscopy, as detailed below.

Peptides doubly tagged with fluorescent dyes (*Biophys. Chem.* 67 (1997), 167-176) have previously been used as fluorogenic substrates for proteinases. In these assays dye-to-dye contact diminishes the fluorescence of the participating dyes by quenching. On enzymatic cleavage of the peptide link, the dye-tagged products dissociate, breaking dye to dye contact, thus relieving quenching of the fluorescence. To observe the increase in fluorescence indicative of enzyme activity usually requires breaking of a covalent bond in the linker. Fluorescent quenching has been used (*Analytical Biochemistry* 165 (1987) 96-101) to measure the distance between a quencher and a fluorophore when attached to a peptide linker. Ai-Ping Wei et al (WO95/03429) uses antibody-antigen reaction to break dye-to-dye contact in order that molecules in the dimer state (fluorescence quenched) become monomeric (fluorescence unquenched) to relieve quenching. This was used to form assays measuring specific antibodies to a recognized peptidic epitope that linked the two dyes. In common with many other homogeneous dequenching assays, while this method can measure antibodies specific to the epitope (used to bind the dyes) in a noncompetitive manner, its adaptation to measuring other analytes, possible only in competitive mode, suffers from disadvantage in that the fluorescence signal becomes indirectly proportional to analyte concentration.

Hence, in one aspect, the invention provides a kit including a recognition molecule and a compound or a complex of the invention. Exemplary recognition molecules include biomolecules, such as whole cells, cell-membrane preparations, antibodies, antibody fragments, proteins (e.g., cell-surface receptors, such as G-protein coupled receptors), protein domains, peptides, nucleic acids, and the like.

The invention further provides kits for the detection of a subject nucleic acid comprising the nucleic acid probe compositions described herein, necessary reagents and instructions for practicing the methods of detection. Such alternative compositions, methods and kits therefor are described in more detail by way of the examples, and still others will be apparent to one of skill in the art in view of the present disclosure.

One embodiment of the present invention provides compositions and methods that measure a resonance energy transfer, for example, a fluorescent signal due to FRET or LRET as a result of direct interaction between two molecular beacons when hybridized to the same target nucleic acid of interest. This method can dramatically reduce false-positive signals in gene detection and quantification in living cells. Probe sequences are chosen such that the molecular beacons hybridize adjacent to each other on a single nucleic acid target in a way that positions their respective fluorophores in optimal configuration for FRET. Emission from the acceptor fluorophore serves as a positive signal in the FRET based detection assay.

If acceptor and donor fluorophores are well matched, excitation of the donor can be achieved at a wavelength that has little or no capacity to excite the acceptor; excitation of the acceptor will therefore only occur if both molecular beacons are hybridized to the same target nucleic acid and FRET occurs. Molecular beacons that are degraded or open due to protein interactions will result in the presence of unquenched fluorophore, however, fluorescence emitted from these species is different in character from the signal obtained from donor/acceptor FRET pair, making background and true positive signal more readily differentiated. Thus, by detecting FRET instead of direct single-molecule fluorescence, nucleic acid probe/target binding events can be distinguished from false-positives.

In one embodiment the invention provides a useful screening tool for drug discovery where a rapid specific and sensitive assay can detect in vivo changes in the expansion role of protein transcripts of interest, either at a steady state or in response to the administration of drug candidates. In another embodiment that can be used in the diagnosis or prognosis of a disease or disorder, the target sequence is a naturally occurring or wild type human genomic or RNA or cDNA sequence, mutation of which is implicated in the presence of a human disease or disorder, or alternatively, the target sequence can be the mutated sequence. In such an embodiment, optionally, the amplification reaction can be repeated for the same sample with different sets of probes that amplify, respectively, the naturally occurring sequence or the mutated version. By way of example, the mutation can be an insertion, substitution, and/or deletion of one or more nucleotides, or a translocation.

In a specific embodiment, the compound of the invention is utilized as a component of a high-throughput nucleic acid sequencing application, where 4-color or 2 color fluorophores are a necessity for the current sequencing platforms. In this embodiment, the invention utilizes multiple different acceptor fluorophores, each one excited by a separate emission band of the luminescent complex of the invention. For example, when a Tb chelate is utilized, four different fluorophores can be used as acceptors. An alternative is to use only 3 different acceptor fluorophores and the fourth color is the remaining uncoupled emission peak of the luminescent metal chelate alone.

In an exemplary embodiment, a set of conventional dyes are selected with peak absorption maxima at each of the chelate-Tb emission maxima, identified as A (490 nm), B (545 nm), C (590 nm), and D (620 nm). These conventional dyes are brought into close proximity (e.g., operative proximity) to the chelate-Tb dye for fluorescent resonance energy transfer (FRET) and a number of conceivable scenarios for this are outlined below.

Figure 3A:
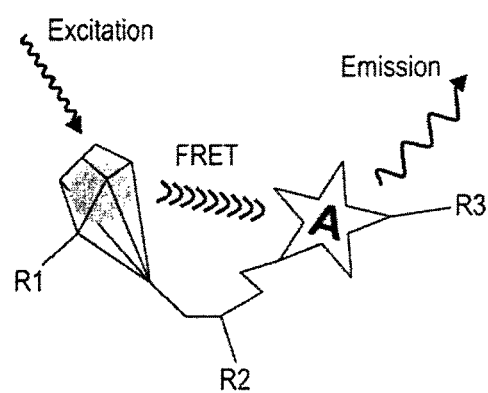
FIG. 3 Four Color FRET Transfer Dyes. A. Covalent synthetic coupling of 4-Tb with a conventional dye via a variable length linker. Various synthetic methods could allow a remaining reactive linker anchored to the 4-Tb (R1), the acceptor-linker (R2), or the Acceptor Dye (R3). B. A series of acceptor dyes are joined to the 4-Tb donor and are tuned to each of the different emission peaks.
Figure 3B:
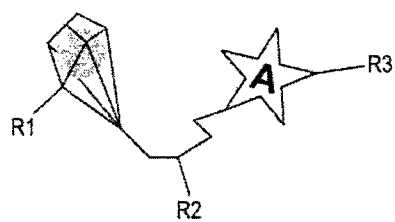
Figure 3B:
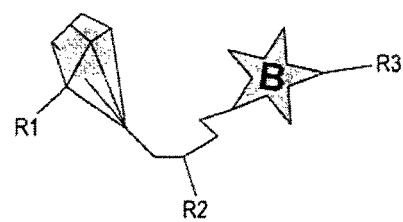
Figure 3B:
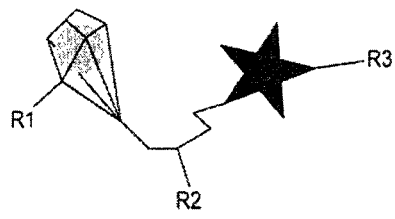
Figure 3B:
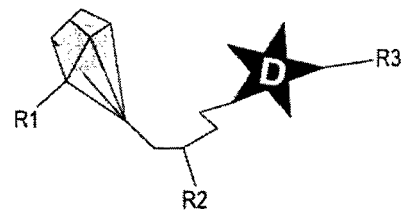

Multicolor dyes based on a luminescent metal chelate donor and various conventional acceptors can be covalently linked (FIG. 3) through synthetic coupling reactions. This has been demonstrated in previous filings as a direct fluorescein conjugate. The obvious extension of this scenario is the inclusion of other acceptors with differing emission wavelengths (FIG. 3B). The usefulness of such molecules is enhanced by an additional linkage moiety (e.g., reactive functional group convertible into a linkage fragment) for synthetic attachment of the construct to biologically relevant molecules such as carrier moieties. As shown in FIG. 3A, these reactive linkages can originate with the chelate-Tb macrocycle (R1), the synthetic linker (R2), or the conventional fluorophore (R3).

The specific linker chosen for such an application has a direct impact on the function of such a molecule in that the distance between acceptor and donor is directly related to the efficiency of energy transfer impacting both the intensity of acceptor emission and the lifetime. Other physical characteristics such as solubility and stability may also tuned by the specific nature of the linker.

Figure 4A:
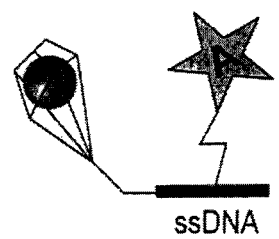
FIG. 4 Same Strand and Hybridized Strand FRET Transfer Dyes.

In another exemplary embodiment, a functionally significant variation of the covalent linkage is embodied in the attachment of both donor and acceptor to the same oligo strand, via synthetic coupling schemes. Features include the ability to tailor quite specifically the distance between donor and acceptor as well as the nature of the donor and acceptor (FIG. 4A). In future application it is envisioned that there might be 'off the shelf' luminescent chelates (e.g., Tb chelates) coupled with the 4 standard base pairs (adenine, guanine, cytosine, thymine) with appropriate chemical make-up for use in current or future automated oligo synthesizers. In a preferred embodiment, this provides an assay readable as four different colors, which are produced by excitation at a single wavelength. Accordingly, the present invention provides assays that are readable in at least two, three, four, five, six, seven, or 8 colors (wavelengths), with excitation at a single wavelength.

Figure 4B:
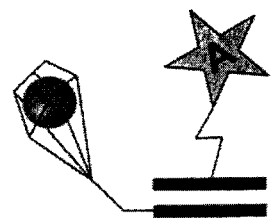
Figure 5:
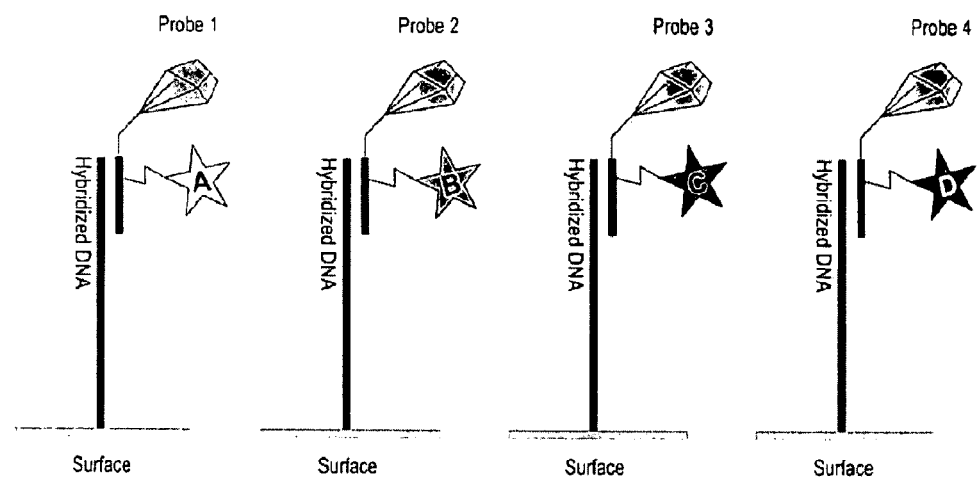
FIG. 5 Surface-Tethered Same Strand multicolored probes based on 4 donor. When different oligos are labeled with different emission colors they can be analyzed in high throughput for genome sequencing applications among others.

A further application of the technology is shown in FIG. 4B whereby two complementary probes are synthesized. One probe would have the chelate-Tb donor incorporated within the sequence and the other would have any number of appropriate acceptor fluorophores similarly incorporated. Upon hybridization the proximity would be such that efficient transfer would occur. In the case of a competing complementary strand from an analyte sample was available, a denature/anneal cycle would interrupt the FRET pair hybridization and signal change would be noted.

Figure 6A:
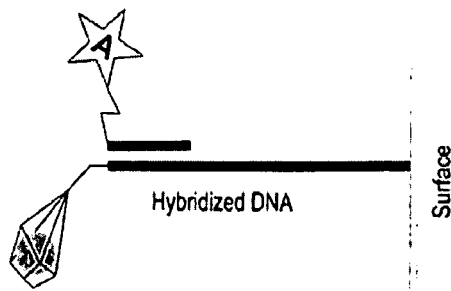
FIG. 6 shows different linking patterns for the donor and acceptor. Depending on the specifics of the application the specific location of the donor or acceptor may be different. (A) The donor is covalently linked to the surface immobilized DNA strand, the acceptor is attached to a solution phase oligo. (B) Both donor and acceptor are attached to the solution phase oligo. (C) Various acceptor fluorophores are attached to probe oligos on a surface support.
Figure 6B:
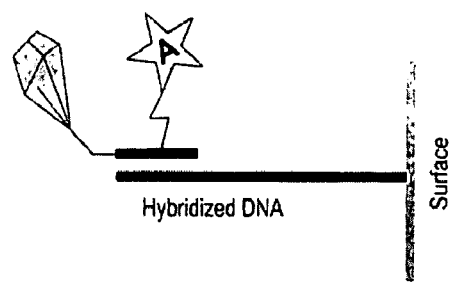
Figure 6C:
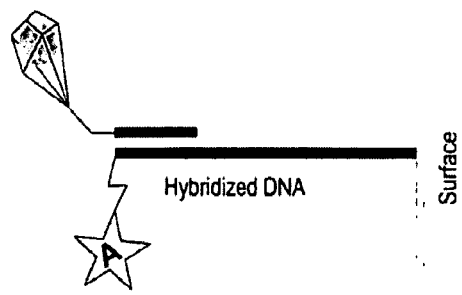

Moreover, as shown in FIG. 6, four color probes could be constructed such that each used the same chelate-Tb donor but different acceptors in differing oligo sequences. This forms the basis of conventional high throughput DNA sequencing modes.

Figure 7A:
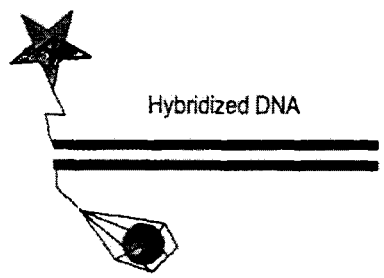
FIG. 7 exemplifies Distance Dependent Lifetime Tuning As the distance between the donor and acceptor is increased, the emission lifetime is decreased. Hybridized DNA offers an exceptionally predictable scaffold for distance tuning.
Figure 7B:
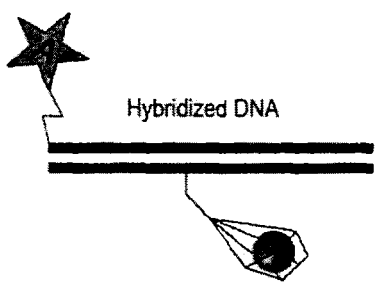
Figure 7C:
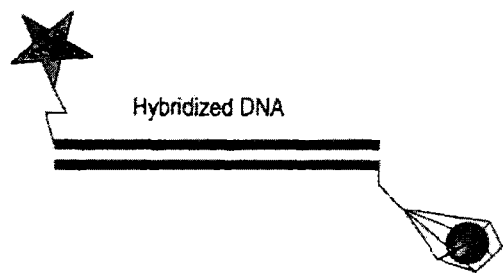
Figure 8:
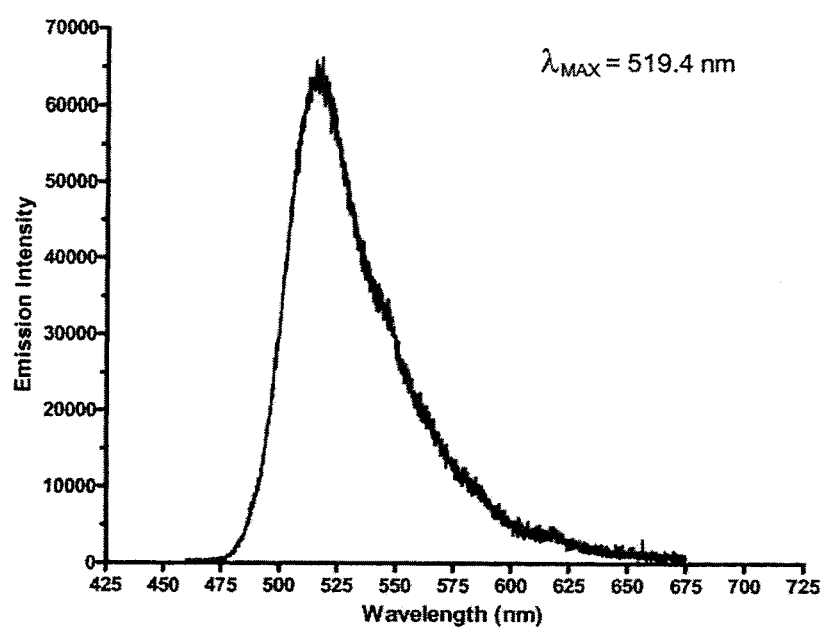
FIG. 8 is a steady-state absorption spectrum of FITC-BH22IAM conjugate.

Currently described within the literature is the relationship between donor-acceptor distance and FRET emission lifetime. As the distance between the donor and the acceptor is reduced, there is a reduction in the fluorescent lifetime of the FRET emission and an increase in the efficiency of energy transfer. DNA is an exceptionally well suited scaffold for lifetime tuning as DNA is quite rigid in the double stranded hybridized form (FIG. 7). It has also been suggested that the lifetime tuning could allow additional multiplexed options based solely on lifetime differences and not emission wavelengths. The combination of multicolor emissions and predictably tuned lifetimes have the potential to greatly increase the multiplexing options available.

Analytes

The compounds, complexes and methods of the invention can be used to detect any analyte or class of analytes in any sample. A sample may contain e.g., a biological fluid (e.g., blood of a patient) or tissue. Other samples can e.g., include solutions of synthetic molecules or extracts from a plant or microorganism (e.g., for drug screening efforts). Exemplary analytes are pharmaceutical drugs, drugs of abuse, synthetic small molecules, biological marker compounds, hormones, infectious agents, toxins, antibodies, proteins, lipids, organic and inorganic ions, carbohydrates and the like. (see, e.g., U.S. Pat. No. 6,864,103 to Raymond et al. for additional examples of analytes).

Synthesis

The compounds and complexes of the invention are synthesized by an appropriate combination of generally well-known synthetic methods. Techniques useful in synthesizing the compounds of the invention are both readily apparent and accessible to those of skill in the relevant art. The discussion below is offered to illustrate certain of the diverse methods available for use in assembling the compounds of the invention, it is not intended to limit the scope of reactions or reaction sequences that are useful in preparing the compounds of the present invention.

In one embodiment, the compounds of the invention are synthesized by reacting a cap molecule with appropriate building blocks, such as hydroxyisophthalic acid. The resulting intermediate is then reacted with a second cap molecule, preferentially containing a functional moiety. Exemplary synthetic routes are outlined in the Examples section of this application.

The syntheses of exemplary cap molecules, containing a functional group, are outlined below. Compound 13 can be prepared by following the synthetic route presented in the scheme below. Compound 13 can then be transformed into compound 9, using the synthetic approach outlined in Example 1.

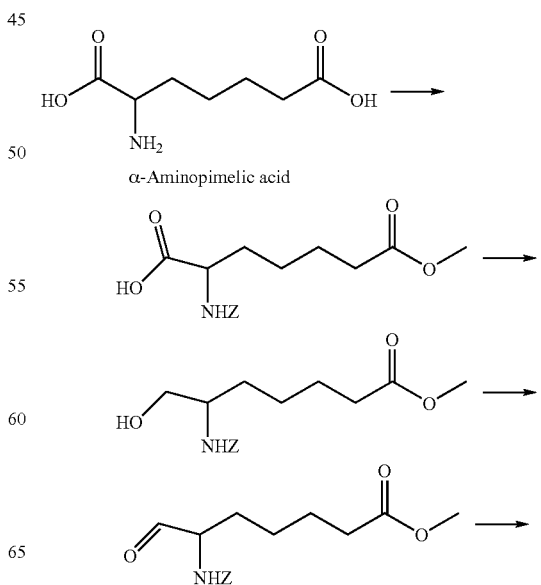

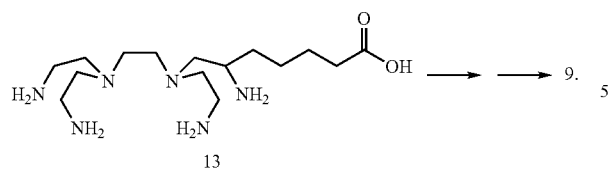

Compound 14 may be prepared using the procedure outlined in the scheme below. Compound II can be prepared from 14 following the procedure of Example 1.

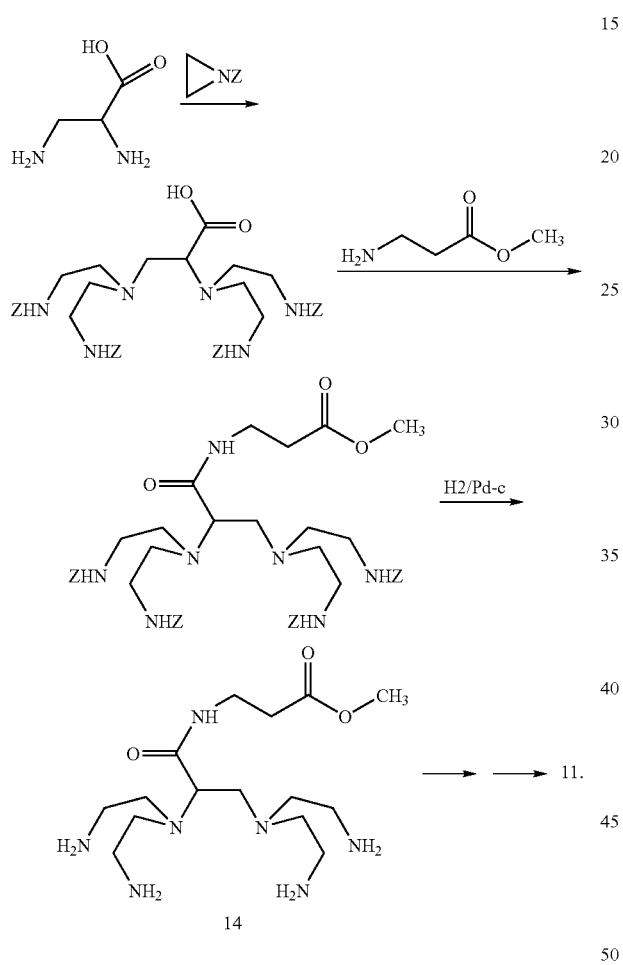

Compound 15 can be prepared using the procedure outlined in the scheme below. Subsequently, 15 can be transformed into compound 10, using the synthetic steps described in Example 1 in addition to a synthetic step useful for the reduction of the nitro group.

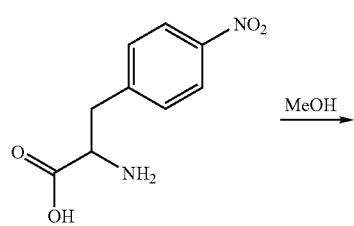

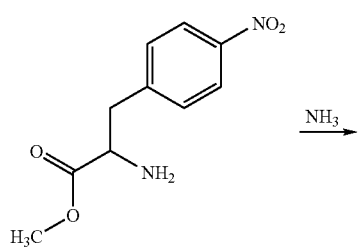

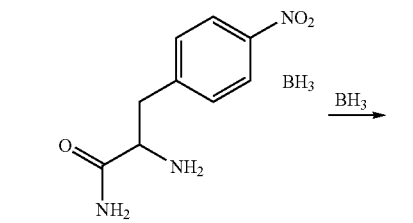

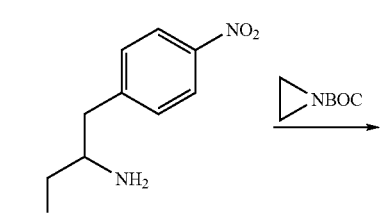

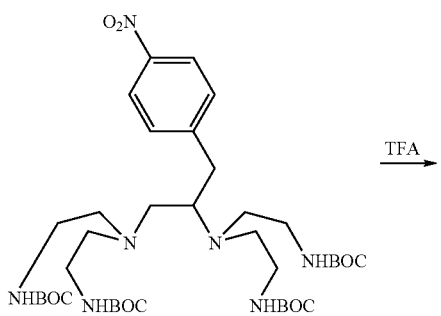

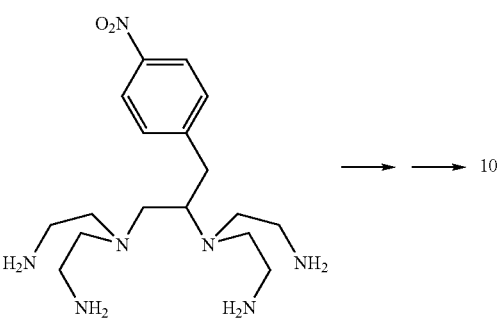

Compound 16 can be synthesized using the procedure outlined in the scheme below and can be used as the starting material to synthesize compound 12 following the synthetic steps outlined in Example 1.

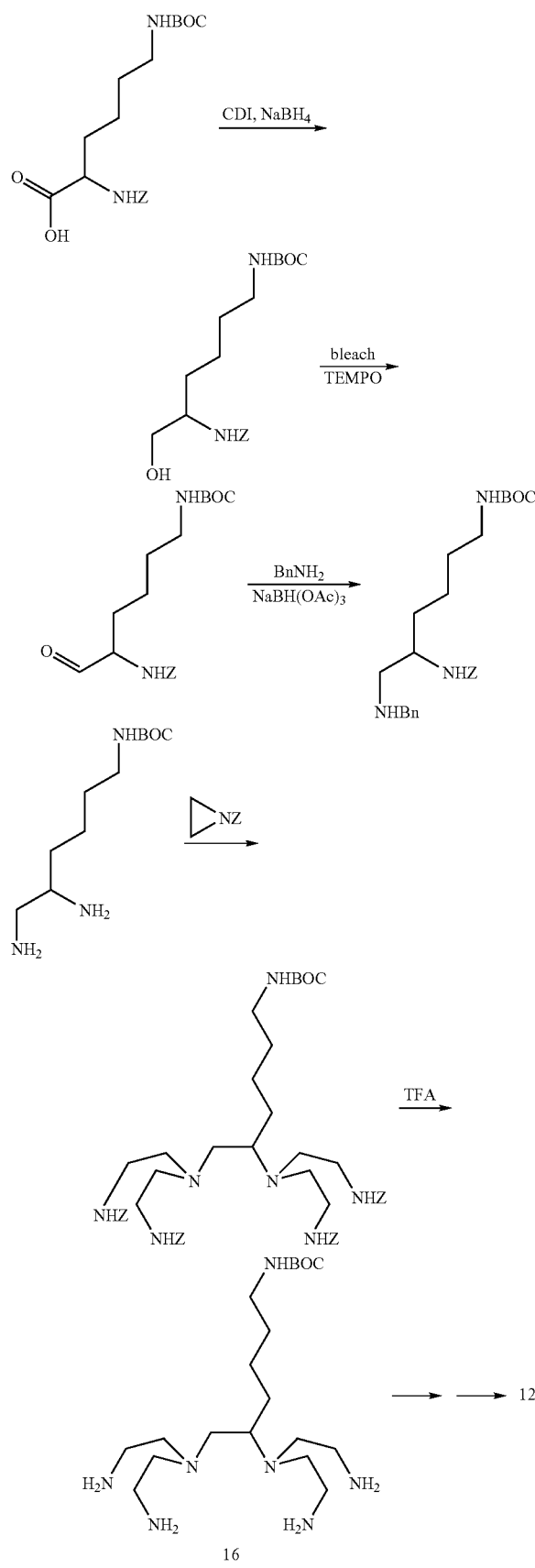

Additional Examples for the synthesis of cap molecules can be found in the Examples section of this application.

Once the ligand is formed and purified, the metal complex is synthesized by any of a wide range of art-recognized methods, including, for example, by incubating a salt of the ligand with a metal salt, such as a lanthanide salt (e.g., lanthanide trihalide, lanthanide triacetate). The reaction of the ligand with the metal ion is carried out either before or after coupling the ligand to a targeting moiety in order to generate a complex of the invention.

Figure 10A:
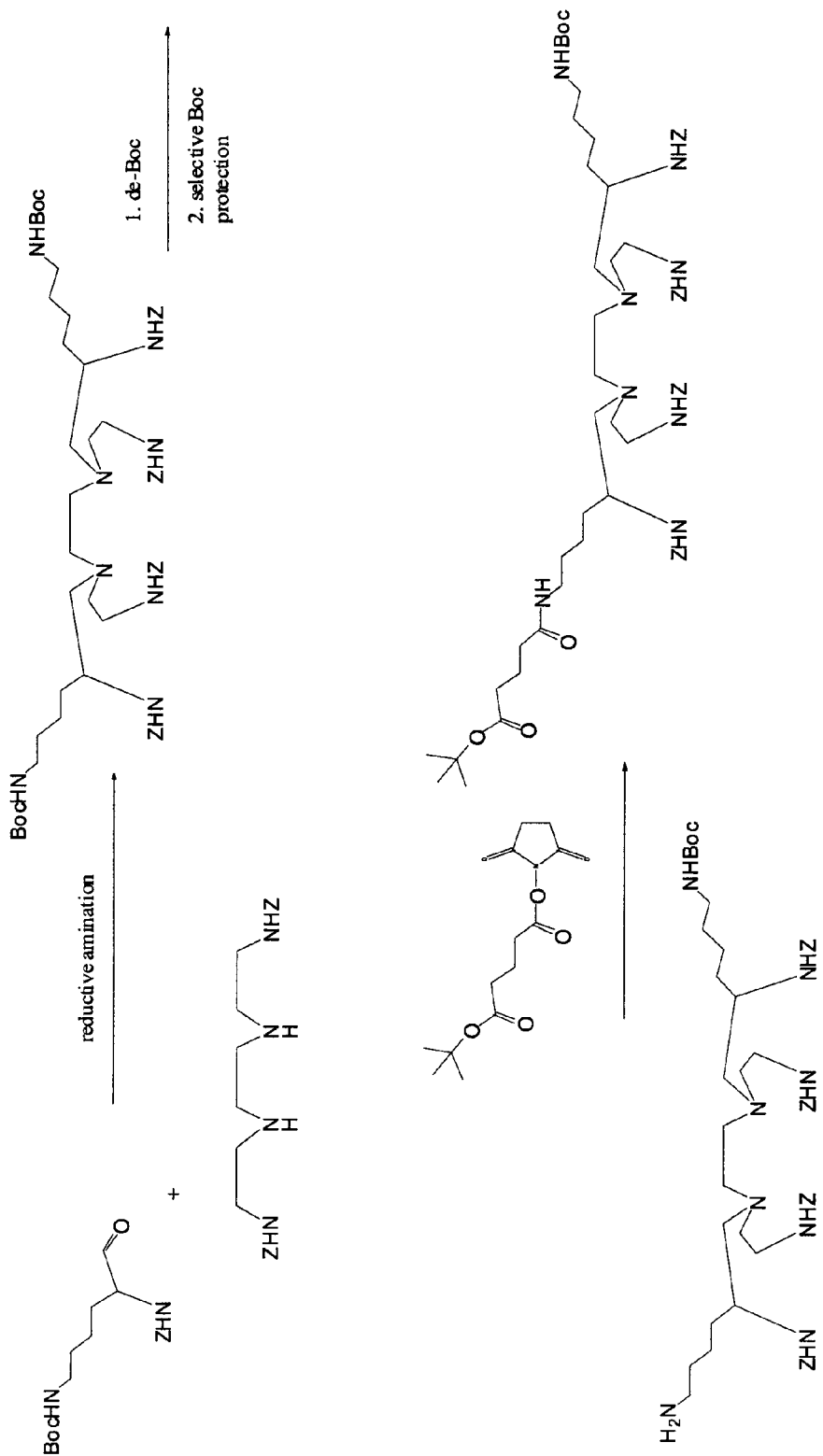
FIG. 10 is an exemplary synthetic scheme for preparing thiourea-coupled, trifunctional complex with a separate derivatization arm (i.e., a functional moiety and/or a acceptor-linker).
Figure 10B:
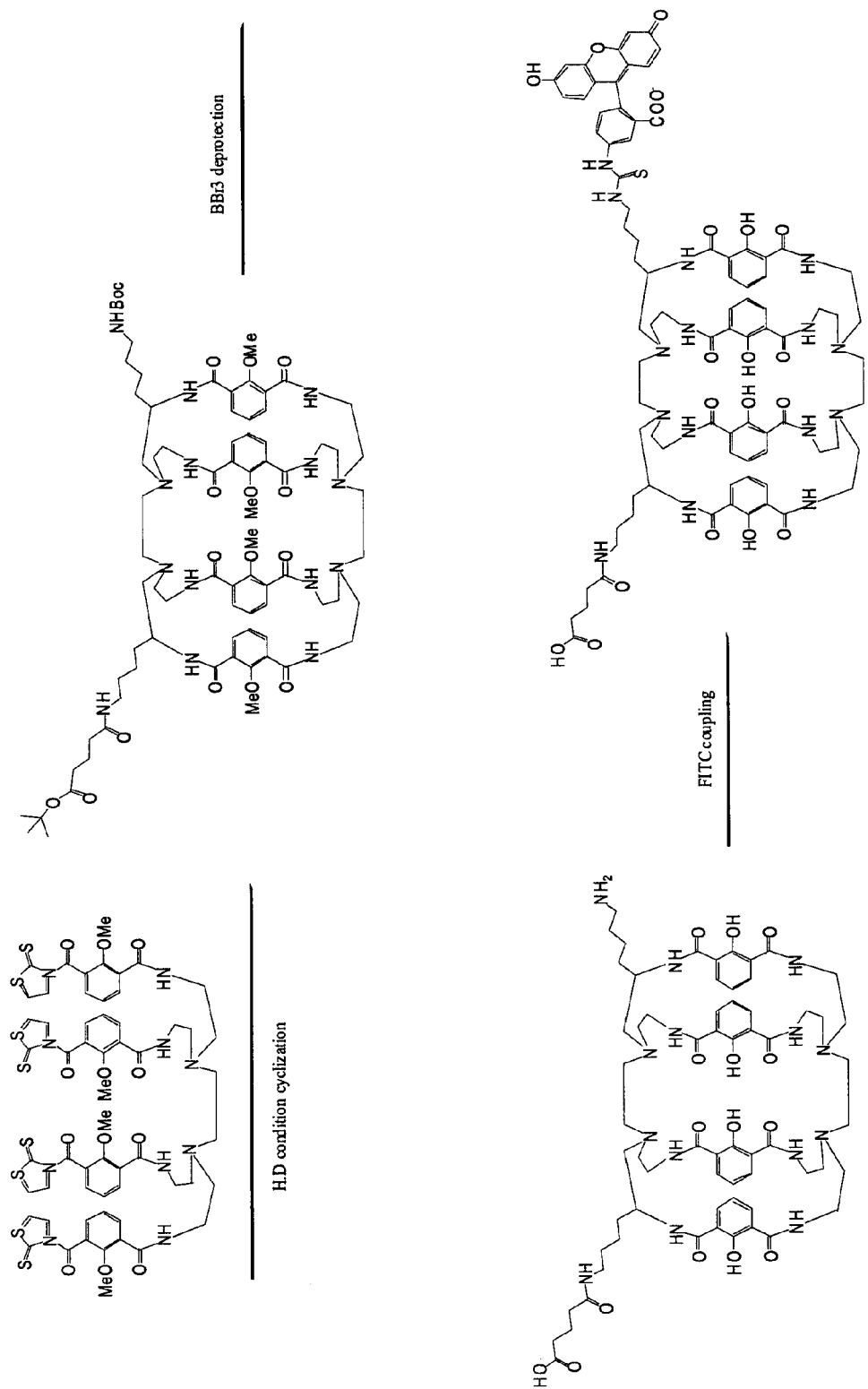
Figure 11A:
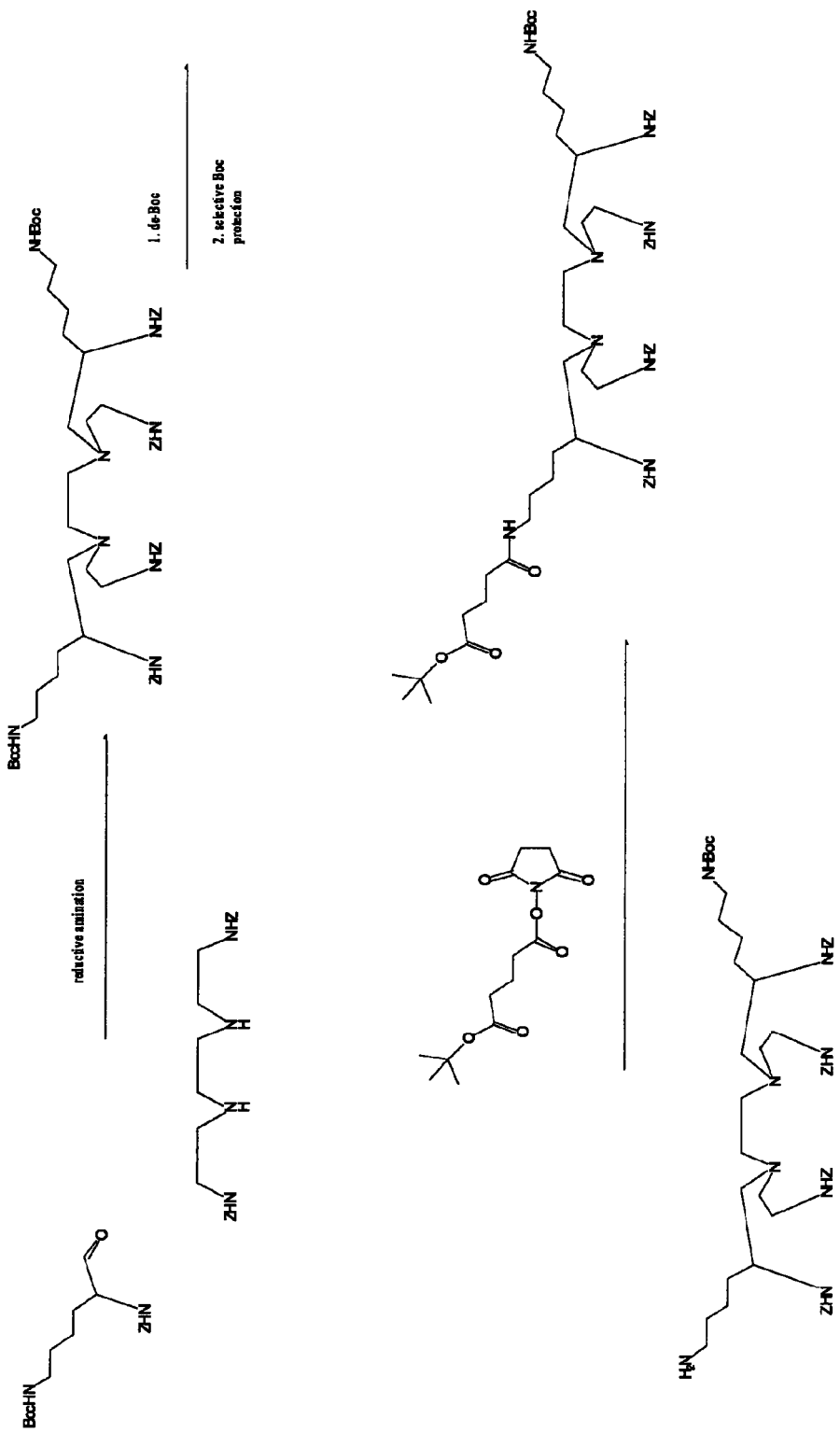
FIG. 11 is an exemplary synthetic scheme for preparing an amide-coupled, trifunctional complex with a separate derivatization arm (i.e., a functional moiety and/or a acceptor-linker).
Figure 11B:
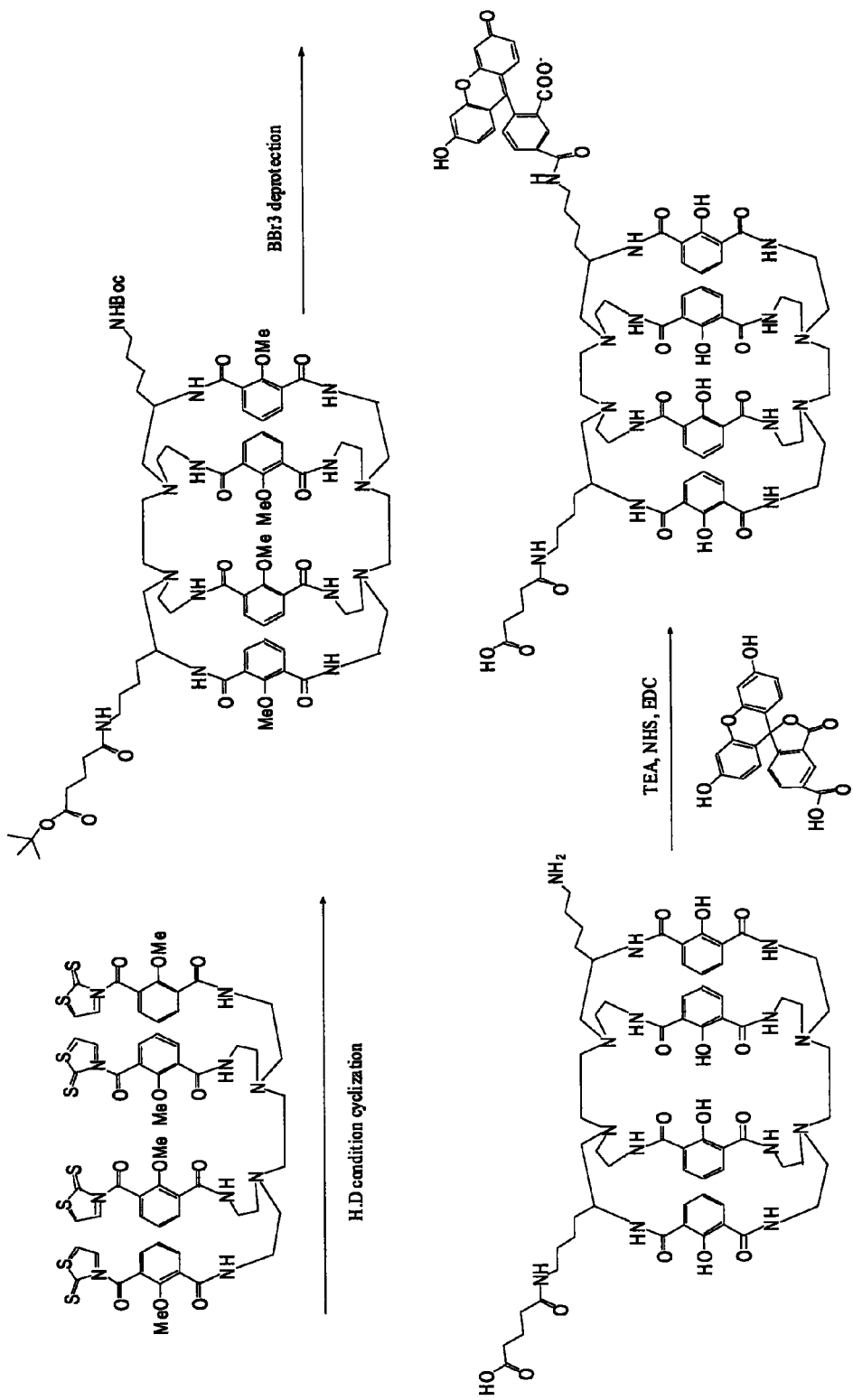
Figure 12:
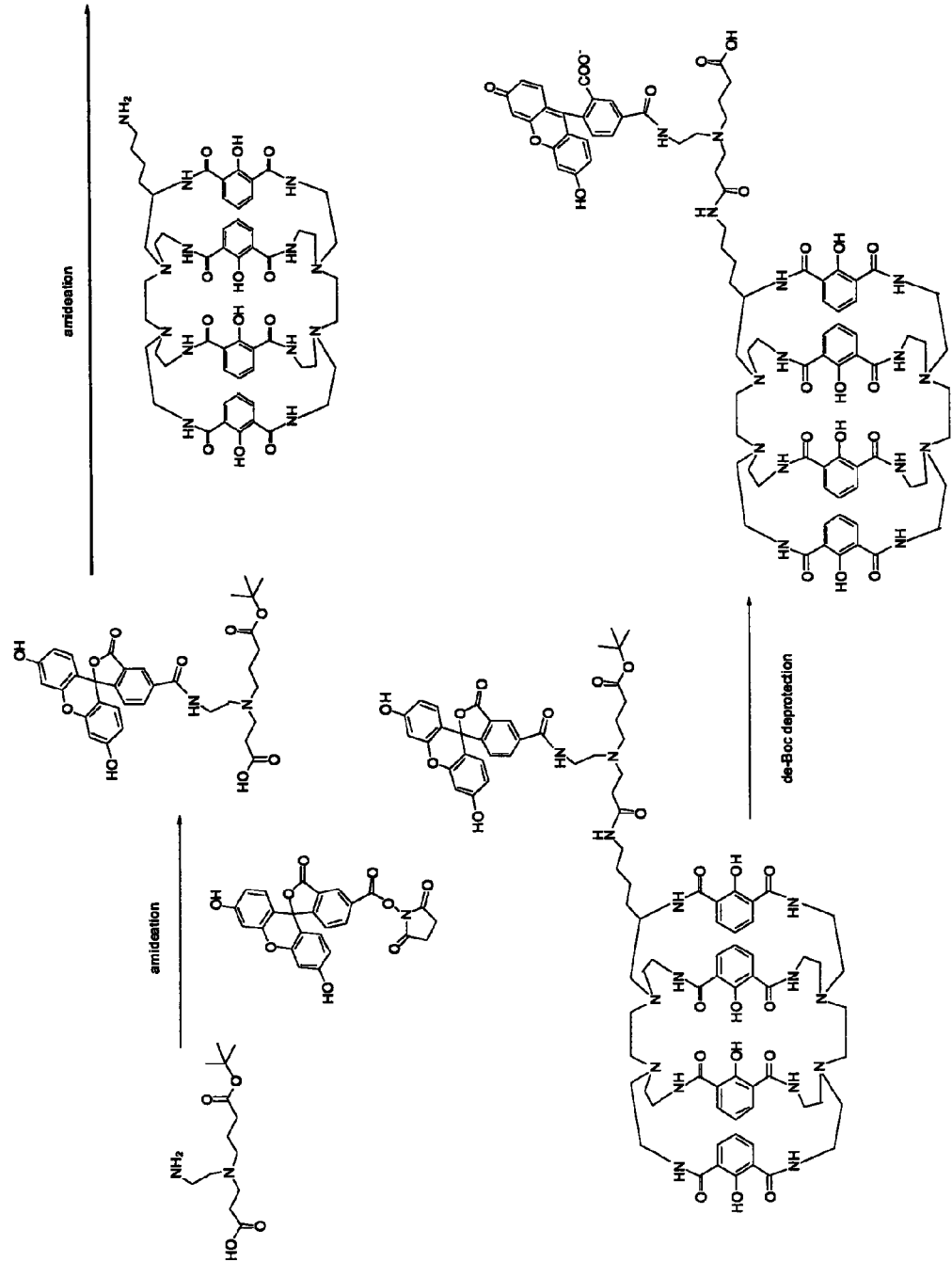
FIG. 12 is an exemplary synthetic scheme for preparing an amide coupled trifunctional complex with a single separate derivatization arm (i.e., including both a acceptor-linker and a functional moiety).
Figure 14:
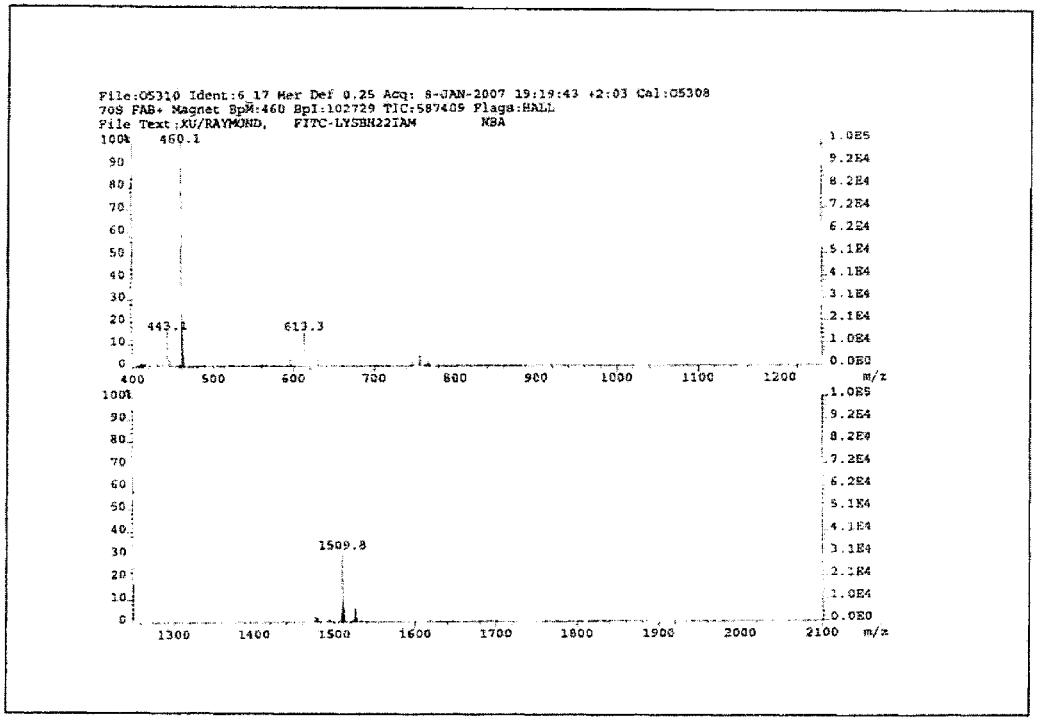
FIG. 14 is a mass spectrum of BH22IAM-FL. Correct parent mass of 1509.8 m/z is indicated for the MH+ ion.

Additional compound according to Formula I can be prepared by the methods set forth in FIG. 10, FIG. 11 and FIG. 12.

In a preferred embodiment, the invention provides a compound having a structure according to Formula I:

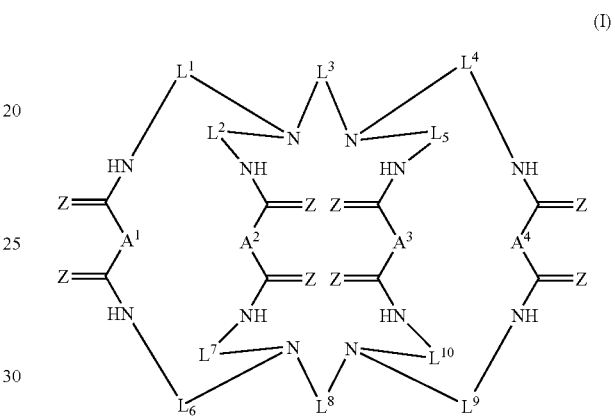

(I)

wherein each Z is a member independently selected from O and S; $L^1$, $L^2$, $L^3$, $L^4$, $L^5$, $L^6$, $L^7$, $L^8$, $L^9$ and $L^{10}$ are linker groups independently selected from substituted or unsubstituted alkyl, substituted or unsubstituted heteroalkyl, substituted or unsubstituted aryl, substituted or unsubstituted heteroaryl, substituted or unsubstituted heterocycloalkyl and nucleic acid; $A^1$, $A^2$, $A^3$ and $A^4$ are members independently selected from the general structure:

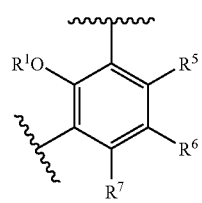

wherein each $R^1$ is a member independently selected from H, an enzymatically labile group, a hydrolytically labile group, a metabolically labile group and a single negative charge; and each $R^5$, $R^6$ and $R^7$ is a member independently selected from H, substituted or unsubstituted alkyl, substituted or unsubstituted heteroalkyl, halogen, CN, $CF_3$, acyl, —$SO_2NR^{17}R^{18}$, —$NR^{17}R^{18}$, —$OR^{17}$, —$S(O)_2R^{17}$, —$COOR^{17}$, —$S(O)_2OR^{17}$, —$OC(O)R^{17}$, —$C(O)NR^{17}R^{18}$, —$NR^{17}C(O)R^{18}$, —$NR^{17}SO_2R^{18}$, and —$NO_2$, wherein $R^6$ and a member selected from $R^5$, $R^7$ and combinations thereof are optionally joined to form a ring system which is a member selected from substituted or unsubstituted cycloalkyl, substituted or unsubstituted heterocycloalkyl, substituted or unsubstituted aryl and substituted or unsubstituted heteroaryl, $R^{17}$ and $R^{18}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and $R^{17}$ and $R^{18}$, together with the atoms to which they are attached, are optionally joined to form a 5- to 7-membered ring, and (a) a first moiety selected from $L^1, L^2, L^3, L^4, L^5, L^6, L^7, L^8, L^9, L^{10}, R^1, R^5, R^6$ and $R^7$ comprises a acceptor-linker covalently attached to a fluorophore wherein said acceptor-linker and said fluorophore are covalently joined through a linkage fragment; or (b) a first moiety selected from $L^1, L^2, L^3, L^4, L^5, L^6, L^7, L^8, L^9, L^{10}, R^1, R^5, R^6$ and $R^7$ comprises a acceptor-linker and a second moiety selected from $L^1, L^2, L^3, L^4, L^5, L^6, L^7, L^8, L^9, L^{10}, R^1, R^5, R^6$ and $R^7$ comprises a functional moiety, wherein said first moiety and said second moiety are different moieties; or (c) a first moiety selected from $L^1, L^2, L^3, L^4, L^5, L^6, L^7, L^8, L^9, L^{10}, R^1, R^5, R^6$ and $R^7$ comprises a acceptor-linker covalently joined, through a linkage fragment, to a fluorophore; and a second moiety selected from $L^1, L^2, L^3, L^4, L^5, L^6, L^7, L^8, L^9, L^{10}, R^1, R^5, R^6$ and $R^7$ comprises a functional moiety wherein said first moiety and said second moiety, each selected from $L^1, L^2, L^3, L^4, L^5, L^6, L^7, L^8, L^9, L^{10}, R^1, R^5, R^6$ and $R^7$, are different moieties; or (e) a first moiety selected from $L^1, L^2, L^3, L^4, L^5, L^6, L^7, L^8, L^9, L^{10}, R^1, R^5, R^6$ and $R^7$ comprises a acceptor-linker; and a second moiety selected from $L^1, L^2, L^3, L^4, L^5, L^6, L^7, L^8, L^9, L^{10}, R^1, R^5, R^6$ and $R^7$ comprises a functional moiety covalently joined, through a linkage fragment, to a member selected from a carrier moiety and a solid support wherein said first moiety and said second moiety, each selected from $L^1, L^2, L^3, L^4, L^5, L^6, L^7, L^8, L^9, L^{10}, R^1, R^5, R^6$ and $R^7$, are different moieties; or (f) a first moiety selected from $L^1, L^2, L^3, L^4, L^5, L^6, L^7, L^8, L^9, L^{10}, R^1, R^5, R^6$ and $R^7$ comprises a acceptor-linker covalently joined, through a linkage fragment, to a fluorophore; and a second moiety selected from $L^1, L^2, L^3, L^4, L^5, L^6, L^7, L^8, L^9, L^{10}, R^1, R^5, R^6$ and $R^7$ comprises a functional moiety covalently joined, through a linkage fragment, to a member selected from a carrier moiety and a solid support wherein said first moiety and said second moiety, each selected from $L^1, L^2, L^3, L^4, L^5, L^6, L^7, L^8, L^9, L^{10}, R^1, R^5, R^6$ and $R^7$, are different moieties a first moiety selected from $L^1, L^2, L^3, L^4, L^5, L^6, L^7, L^8, L^9, L^{10}, R^1, R^5, R^6$ and $R^7$ comprises a moiety which is both a fluorescent-linker and a functional moiety; or (g) a first moiety selected from $L^1, L^2, L^3, L^4, L^5, L^6, L^7, L^8, L^9, L^{10}, R^1, R^5, R^6$ and $R^7$ comprises a moiety which is both a fluorescent-linker and a functional moiety covalently bound, through at least one linkage fragment to at least one member selected from a fluorophore, a carrier moiety, a solid support and a combination thereof, wherein each of said at least one linkage fragment is the same or different.

In another preferred embodiment, the invention provides a compound according to the paragraph above, having the structure:

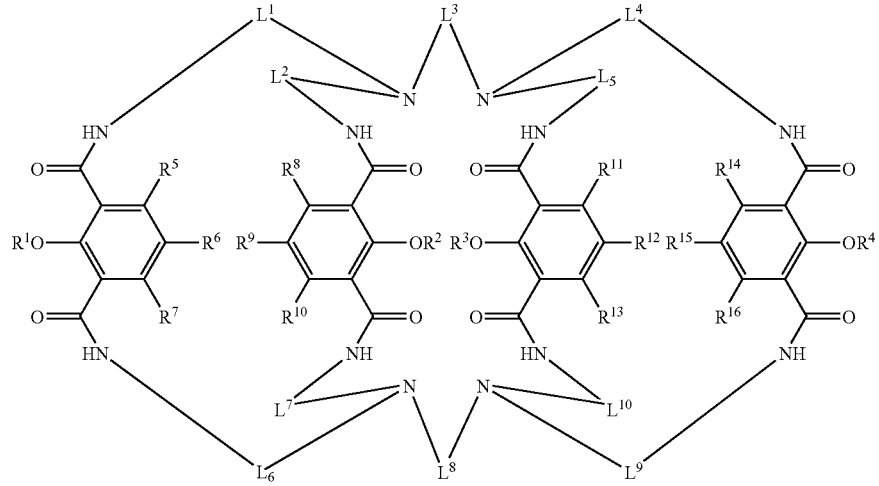

In another preferred embodiment, the invention provides a compound according to any of the paragraphs above, having a structure, which is a member selected from:

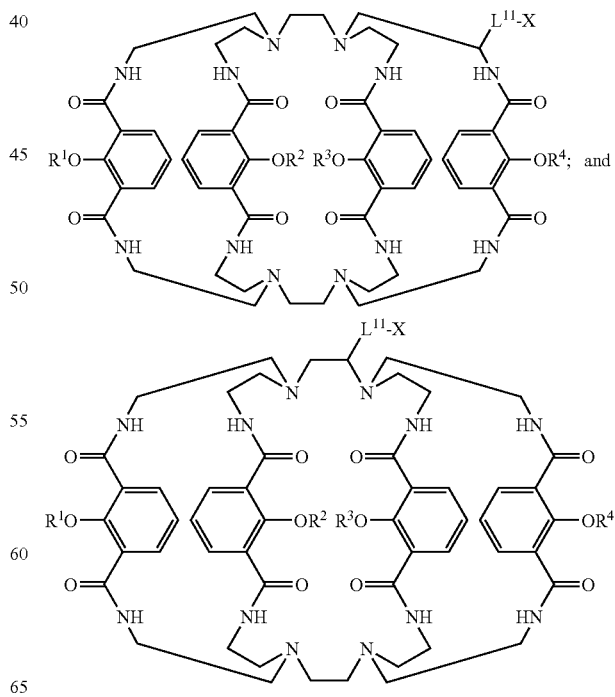

wherein $L^{11}$ is a member selected from a bond, acyl, substituted or unsubstituted alkyl, substituted or unsubstituted heteroalkyl, substituted or unsubstituted aryl, substituted or unsubstituted heteroaryl, substituted or unsubstituted heterocycloalkyl and nucleic acid; and X is a linkage fragment covalently binding a fluorophore to $L^{11}$.

In another preferred embodiment, the invention provides a compound according to any of the paragraphs above, wherein said linker moieties $L^1, L^2, L^3, L^4, L^5, L^6, L^7, L^8, L^9$ and $L^{10}$ are members independently selected from substituted or unsubstituted $C_1$ to $C_6$ alkyl.

In another preferred embodiment, the invention provides a compound according to any of the paragraphs above, wherein said linker moieties $L^1, L^2, L^3, L^4, L^5, L^6, L^7, L^8, L^9$ and $L^{10}$ are members independently selected from substituted or unsubstituted ethyl.

In another preferred embodiment, the invention provides a luminescent complex formed between at least one metal ion and a compound according to any of the paragraphs above. An exemplary metal ion is a lanthanide ion (e.g., a member selected from neodynium (Nd), samarium (Sm), europium (Eu), terbium (Tb), dysprosium (Dy) and ytterbium (Yb)).

In another preferred embodiment, the invention provides a mixture comprising: (i) a first compound having a structure according to Formula I:

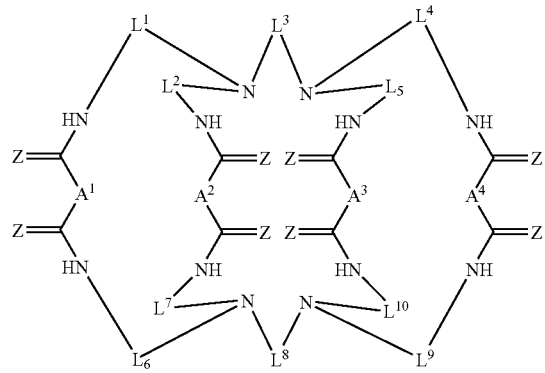

(I)

e.g., such as discussed in any of the paragraphs above, wherein each Z is a member independently selected from O and S; $L^1, L^2, L^3, L^4, L^5, L^6, L^7, L^8, L^9, L^{10}$ are linker groups independently selected from substituted or unsubstituted alkyl, substituted or unsubstituted heteroalkyl, substituted or unsubstituted aryl, substituted or unsubstituted heteroaryl and substituted or unsubstituted heterocycloalkyl;
$A^1, A^2, A^3$ and $A^4$ are members independently selected from the general structure:

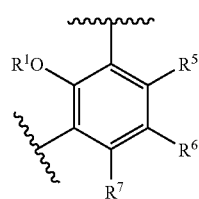

wherein each $R^1$ is a member independently selected from H, an enzymatically labile group, a hydrolytically labile group, a metabolically labile group and a single negative charge; and each $R^5, R^6$ and $R^7$ is a member independently selected from H, substituted or unsubstituted alkyl, substituted or unsubstituted heteroalkyl, halogen, CN, $CF_3$, acyl, $-SO_2NR^{17}R^{18}$, $-NR^{17}R^{18}$, $-OR^{17}$, $-S(O)_2R^{17}$, $-COOR^{17}$, $-S(O)_2OR^{17}$, $-OC(O)R^{17}$, $-C(O)NR^{17}R^{18}$, $-NR^{17}C(O)R^{18}$, $-NR^{17}SO_2R^{18}$, and $-NO_2$, wherein $R^6$ and a member selected from $R^5, R^7$ and combinations thereof are optionally joined to form a ring system which is a member selected from substituted or unsubstituted cycloalkyl, substituted or unsubstituted heterocycloalkyl, substituted or unsubstituted aryl and substituted or unsubstituted heteroaryl, $R^{17}$ and $R^{18}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and $R^{17}$ and $R^{18}$, together with the atoms to which they are attached, are optionally joined to form a 5- to 7-membered ring; and (ii) a second compound having an acceptor, e.g., a fluorophore or quencher attached thereto.

In another preferred embodiment, the invention provides a mixture according to the paragraph above wherein said compound according to Formula I is a luminescent metal ion complex, and said first compound and said second compound interact such that an energy exchange pair is formed wherein excitation energy from said first compound is transferred to said fluorophore of said second compound, forming an excited fluorophore, which detectably luminesces.

In another preferred embodiment, the invention provides a mixture according to the paragraphs above, wherein metal ion is a lanthanide ion which is a member selected from neodynium (Nd), samarium (Sm), europium (Eu), terbium (Tb), dysprosium (Dy) and ytterbium (Yb).

In another preferred embodiment, the invention provides a mixture according to the paragraphs above wherein said first compound is covalently attached through a functional moiety to a first nucleic acid.

In another preferred embodiment, the invention provides a mixture according to the paragraphs above wherein said second compound is a nucleic acid.

In another preferred embodiment, the invention provides a mixture according to the paragraphs above wherein said first nucleic acid and said second nucleic acid independently comprise from about 5 to about 50 nucleotides.

In another preferred embodiment, the invention provides a mixture according to the paragraphs above wherein said first nucleic acid and said second nucleic acid independently comprise from 10 to 40 nucleotides.

In another preferred embodiment, the invention provides a mixture according to the paragraphs above wherein said first nucleic acid and said second nucleic acid independently comprise from 15 to 30 nucleotides.

In another preferred embodiment, the invention provides a mixture according to the paragraphs above wherein one member selected from said first nucleic acid, said second nucleic acid and a combination thereof participates in both stem-loop formation and hybridization to the target sequence nucleic acid.

In another preferred embodiment, the invention provides a method of detecting an analyte in a sample, said method comprising: contacting said analyte with a compound according to any of the paragraphs above (preferably a metal chelate, e.g., a luminescent metal chelate, e.g., a luminescent lanthanide chelate), wherein an energy transfer pair is formed between said compound and a member selected from said analyte, an acceptor (e.g., a fluorophore, quencher, and the like) bound to said analyte and a combination thereof; exciting said compound such that said compound transfers excitation energy to a member selected from said analyte, said fluorophore bound to said analyte; and detecting energy transferred by the compound, e.g., by detecting luminescence emitted by a member selected from said analyte, said fluorophore bound to said analyte and a combination thereof.

In another preferred embodiment, the invention provides a method according to the paragraphs above wherein said analyte is a nucleic acid.

In another preferred embodiment, the invention provides a method according to the paragraphs above wherein the method is performed in vivo.

In another preferred embodiment, the invention provides a method according to the paragraphs above wherein the sample contains a living cell.

In another preferred embodiment, the invention provides a method according to the paragraphs above wherein said nucleic acid comprises a genetic point mutation, deletion or insertion relative to a control nucleic acid.

In another preferred embodiment, the invention provides a method according to the paragraphs above wherein the detection of said nucleic acid indicates the presence of a cancer in the sample.

In another preferred embodiment, the invention provides a method according to the paragraphs above wherein the detection of said nucleic acid indicates an alteration of the expression pattern of said nucleic acid in response to an external stimulus.

In another preferred embodiment, the invention provides a method according to the paragraphs above wherein the detecting is performed with single- or multiple-photon microscopy, time-resolved fluorescence microscopy or fluorescence endoscopy.

In another preferred embodiment according to any of the paragraphs above, detecting fluorescence can detect multiple wavelengths from one or more fluorophore with excitation of the one or more fluorophre at a single wavelength.

The following examples are provided to illustrate selected embodiments of the invention and are not to be construed as limiting its scope.

EXAMPLES

Example 1

Synthesis of the Macrocyclic Ligand (4)

A variety of synthetic routes were pursued to obtain derivatized versions of compound 3. Those efforts lead to a method for the synthesis of compound 4. The derivatized building block used in the synthesis of 4 is prepared from lysine and tris(2-aminoethyl)amine (TREN) as outlined in Scheme 1 below.

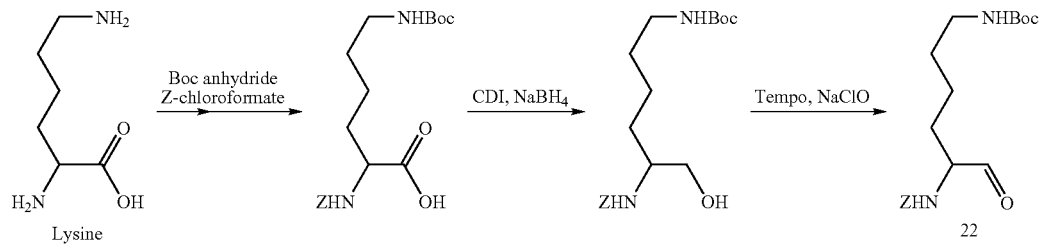

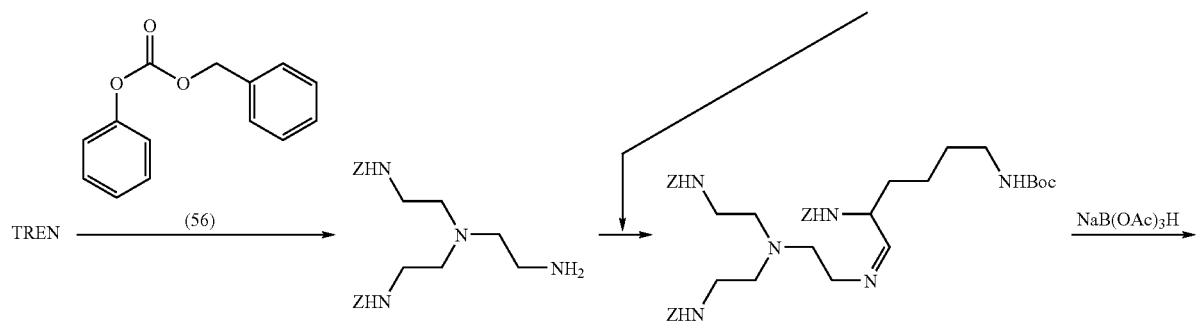

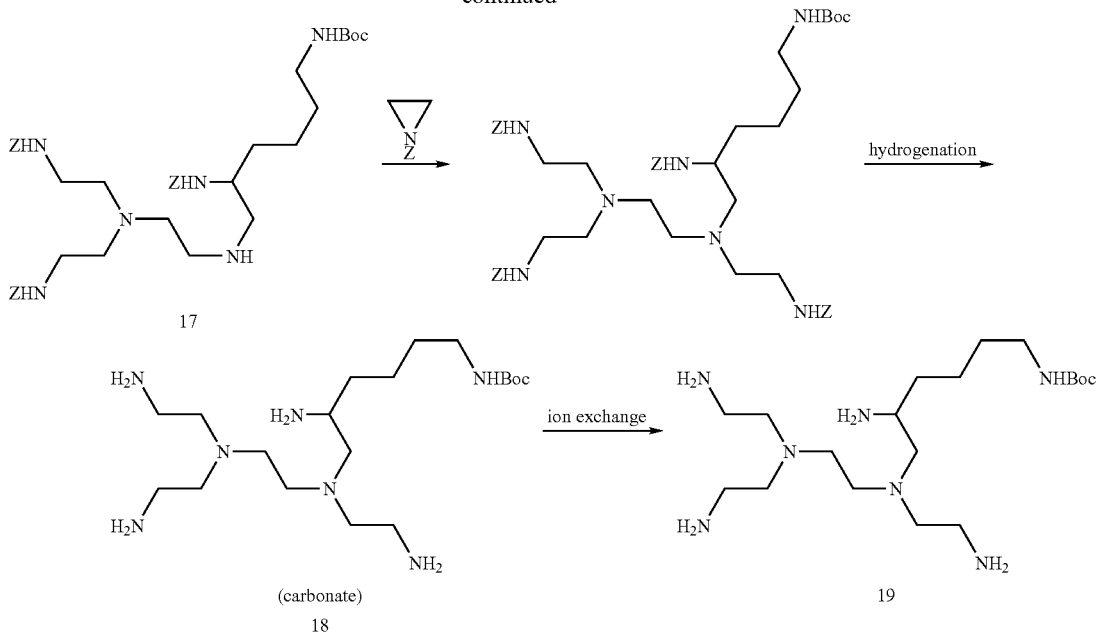

Reductive amination of the protected lysine derivative 22 using Z-protected tris(2-aminoethyl)amine (TREN) led to the intermediate 17, which was further derivatized by reaction with a protected aziridine. Removal of the Z-protection groups by hydrogenation afforded the carbonate salt 18, which was transformed into the corresponding free base. The Boc-protected molecule 19 was then used to prepare compound 4 as outlined in Scheme 2 below.

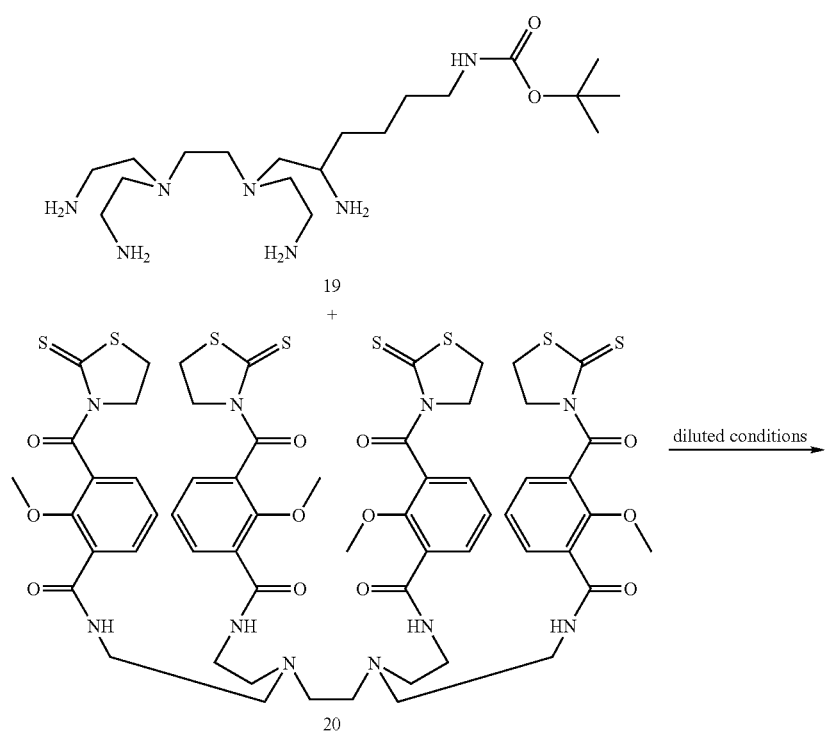

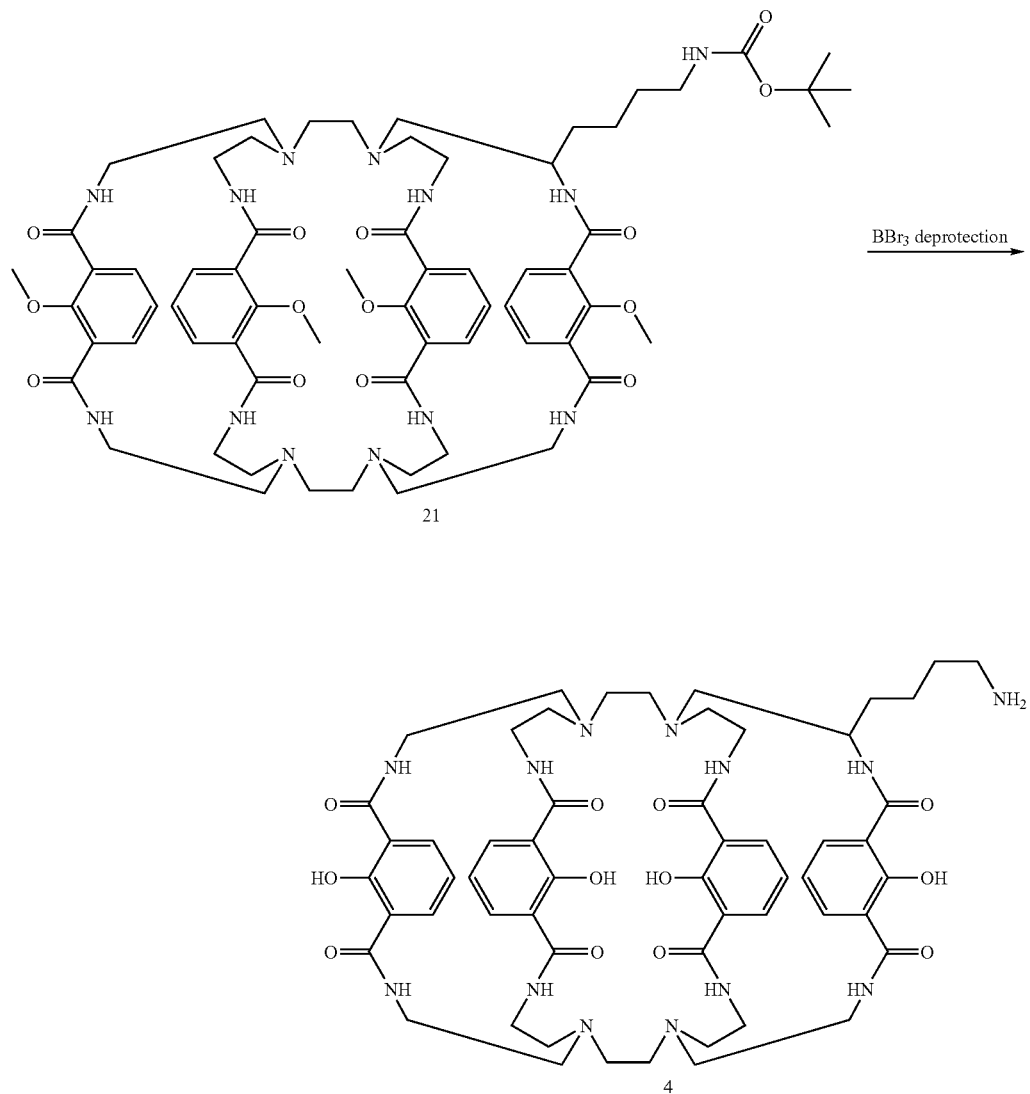

Compound 19 was reacted with compound 20 under high dilution conditions to yield the protected intermediate 21. Deprotection of the methoxy groups with boron tribromide produced the hexa-hydrobromide of the functionalized macrocyclic ligand derivative 4 as a beige colored powder. The structure was confirmed by FAB mass and elemental analysis.

The product was analyzed by mass spectroscopy. The crude mixture was separated into two main fractions. Each fraction contained several "sub-fractions" with similar $R_f$ values. Mass spectral analysis revealed that both main fractions were composed of the desired product 4. However, the first main fraction, which had a higher $R_f$ value, included trapped guests of chloroform or methylene chloride. The second main fraction, which had a lower $R_f$, showed the parent peak at 1276.7 (m/s).

A qualitative luminescent test was initiated by mixing a solution of ligand 4, a dilute terbium or europium salt solution and a few drops of sodium carbonate solution. As a control, the ligand alone was mixed with sodium carbonate solution. The mixtures containing the lanthanide complexes exhibited strong luminescence under long wave UV light (366 nm). The ligand, without complexation to a metal ion, did not show luminescence under the same conditions.

Example 2

Synthesis of the Macrocyclic Ligand (5)

Compound 5 was synthesized by coupling the primary amine group of ligand 4 to diglycolic acid according to Scheme 3 below. In an analogues manner, compound 5a was synthesized by coupling 4 to glutaric acid.

Scheme 3
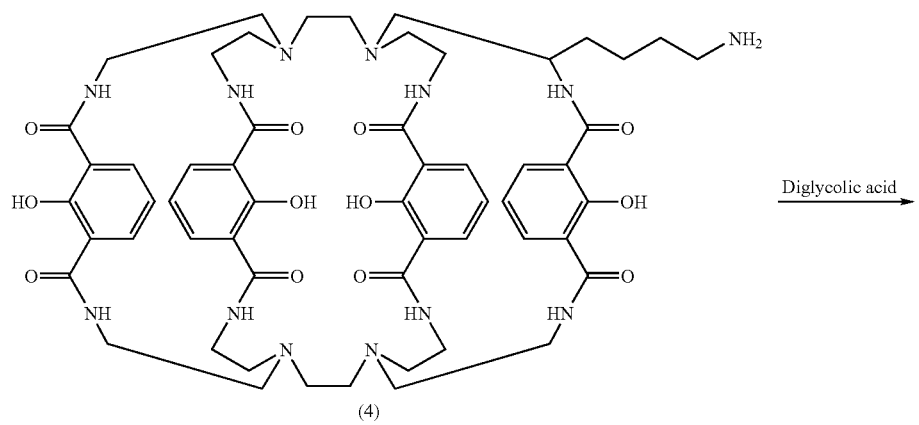
Example 5
Synthesis of Donor-Acceptor Conjugate (4a)
Scheme 4
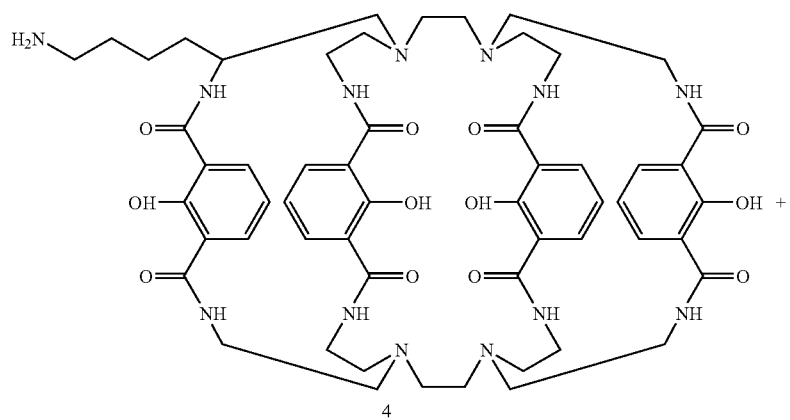

-continued

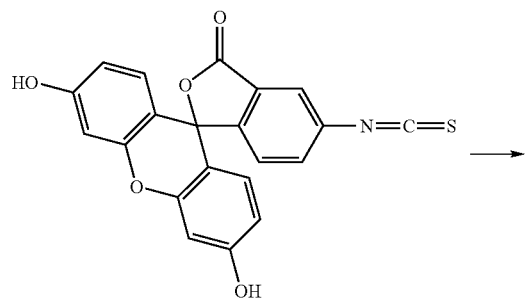

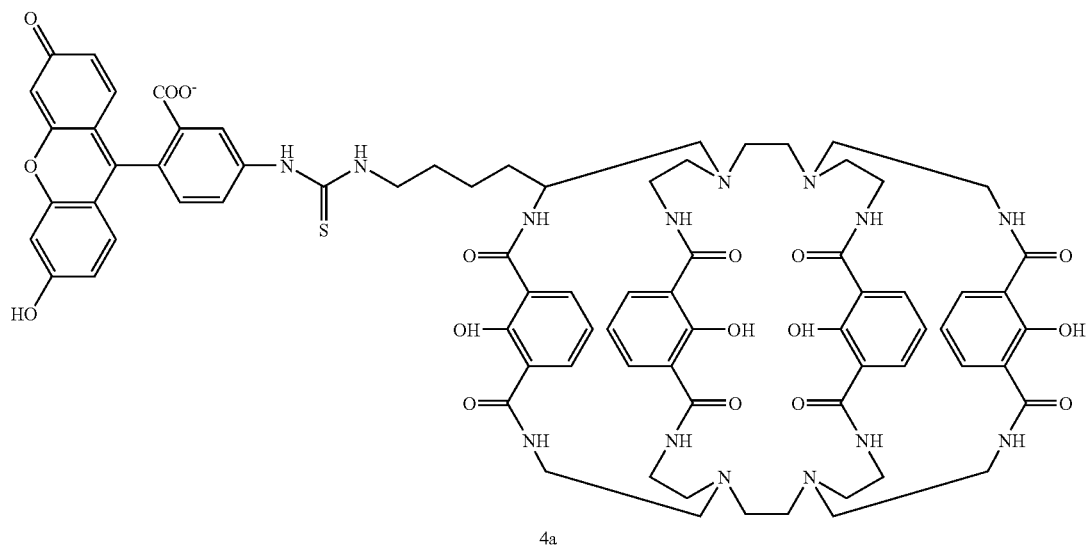

4a

According to Scheme 4, a solution of (4) BH22IAM-NH$_2$ (C$_{56}$H$_{73}$N$_{13}$O$_{12}$.5HBr.8H2O, F.W. 1668.95) (12 mg, 7.2 µmol) and dry triethylamine (50 µL) in of dry DMF (0.5 mL), FITC (fluorescein isothiocyanate isomer 1) (5.6 mg, 2 equivalents, Alfa Aesar product, 95%) was added with stirring. The mixture was capped in a closed vial overnight. The reaction mixture was filtered with a glass wool/plug glass pipette and dropped into dry ether (35 mL) with stirring to precipitate the raw product from DMF and excess triethylamine. After centrifuging at 5000 rpm for 30 min, the raw product was isolated as a yellowish brown solid.

The raw product was suspended in a mixture of methanol (10 mL) and acetonitrile (30 mL), and then centrifuged. The mother liquor contains the unconjugated FITC or its derivatives and was discarded. The solid was suspended in 30 mL of fresh methanol:acetonitrile (1:3) mixture and centrifuged under the same conditions. The mother liquor showed slight yellow color indicated the separation of un-conjugated FITC may be done. The residue was then suspended into pure methanol (5 mL) and centrifuged at 12K rpm, 10 min to remove the unconjugated macrocycle. After centrifugation the residue was resuspended in 2 mL methanol and centrifuged under the same conditions again. The color of the mother liquor was much lighter than the first time, indicating that significant product purity was obtained.

The newly synthesized molecule exhibits some properties consistent with intramolecular fluorescence resonance energy transfer (FRET) such as absorption maxima at 340 nm (BH22IAM) and 490 nm (fluorescein) as well as emission maxima at 519 nm. The fluorescent lifetime of the newly synthesized molecule possesses an intermediate lifetime of 520 nsec.

This new molecule is exemplary of the ability to generate new fluorescent compounds with lifetimes long enough to be useful in time resolved fluorescence (TRF) applications, but possessing emission wavelengths of most conventional fluorophores. The 524 nsec of the conjugated fluorescein is acquired through direct excitation of the Tb-BH22IAM complex at 340 nm, which normally has a very long lifetime (2.6 msec), followed by energy transfer to the conjugated fluorescein and emission at the characteristic wavelength for fluorescein (520 nm).

It is understood that the examples and embodiments described herein are for illustrative purposes only and that various modifications or changes in light thereof will be suggested to persons skilled in the art and are to included within the spirit and purview of this application and are considered within the scope of the appended claims. All publications, patents, and patent applications cited herein are hereby incorporated by reference in their entirety for all purposes.

What is claimed is:

1. A compound having a structure according to Formula I:

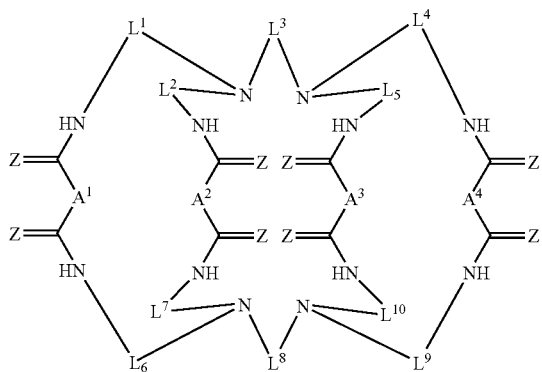

wherein
each Z is a member independently selected from O and S;
$L^1, L^2, L^3, L^4, L^5, L^6, L^7, L^8, L^9$ and $L^{10}$ are linker groups independently selected from substituted or unsubstituted $C_1$ to $C_6$ alkyl;
$A^1, A^2, A^3$ and $A^4$ are members independently selected from the general structure:

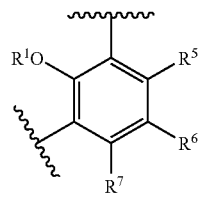

wherein
each $R^1$ is a member independently selected from H, an enzymatically labile group, a hydrolytically labile group, a metabolically labile group and a single negative charge; and
each $R^5, R^6$ and $R^7$ is a member independently selected from H, substituted or unsubstituted alkyl, substituted or unsubstituted heteroalkyl, halogen, CN, $CF_3$, acyl, $-SO_2NR^{17}R^{18}$, $-NR^{17}R^{18}$, $-OR^{17}$, $-S(O)_2R^{17}$, $-COOR^{17}$, $-S(O)_2OR^{17}$, $-OC(O)R^{17}$, $-C(O)NR^{17}R^{18}$, $-NR^{17}C(O)R^{18}$, $-NR^{17}SO_2R^{18}$, and $NO_2$,
wherein
$R^6$ and a member selected from $R^5, R^7$ and combinations thereof are optionally joined to form a ring system which is a member selected from substituted or unsubstituted cycloalkyl, substituted or unsubstituted heterocycloalkyl, substituted or unsubstituted aryl and substituted or unsubstituted heteroaryl; and
$R^{17}$ and $R^{18}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and $R^{17}$ and $R^{18}$, together with the atoms to which they are attached, are optionally joined to form a 5- to 7-membered ring; and
wherein at least one moiety selected from $L^1, L^2, L^3, L^4, L^5, L^6, L^7, L^8, L^9$, and $L^{10}$ is substituted with:

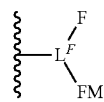

wherein
$L^F$ is an acceptor-linker;
F is a fluorophore bound to $L^F$ through a linkage fragment; and
FM is a functional moiety,
wherein said functional moiety comprises a reactive functional group, or said functional moiety is bound to a carrier moiety or solid support through a linkage fragment.

2. The compound according to claim 1, having a structure, which is a member selected from:

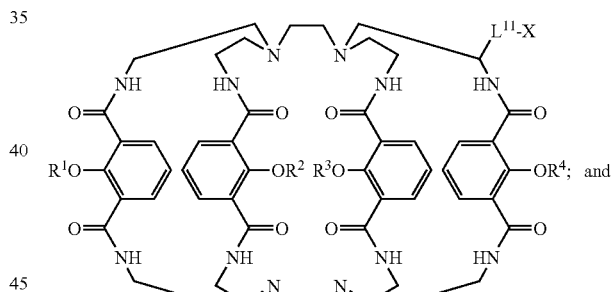

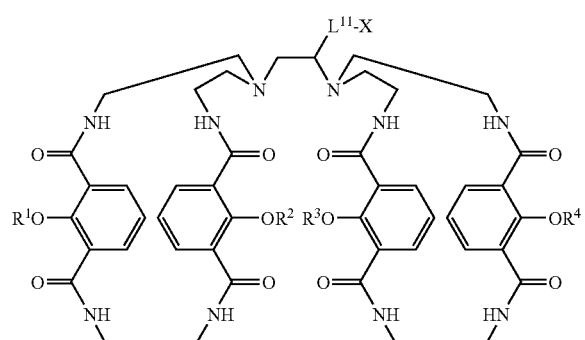

wherein
- $L^{11}$ is a member selected from a acyl, substituted alkyl, substituted heteroalkyl, substituted aryl, substituted heteroaryl, substituted heterocycloalkyl and nucleic acid; and
- X is a linkage fragment covalently binding said fluorophore to $L^{11}$.

3. The compound according to claim 1, wherein said linker moieties $L^1, L^2, L^3, L^4, L^5, L^6, L^7, L^8, L^9$ and $L^{10}$ are members independently selected from substituted or unsubstituted ethyl.

4. A luminescent complex formed between at least one metal ion and a compound according to claim 1.

5. The complex according to claim 4, wherein said metal ion is a lanthanide ion.

6. The complex according to claim 5, wherein said lanthanide is a member selected from neodymium (Nd), samarium (Sm), europium (Eu), terbium (Tb), dysprosium (Dy) and ytterbium (Yb).

7. A method of detecting an analyte in a sample, said method comprising:
   (a) combining the sample and the complex according to claim 4;
   (b) exciting the complex; and
   (c) detecting luminescence from the complex, thereby detecting said analyte.

8. The method according to claim 7 wherein said analyte is a nucleic acid.

9. The method of claim 7 wherein the method is performed in vivo.

10. The method of claim 7 wherein the sample contains a living cell.

11. The method of claim 8 wherein said nucleic acid comprises a genetic point mutation, deletion or insertion relative to a control nucleic acid.

12. The method of claim 8 wherein the detection of said nucleic acid indicates the presence of a cancer in the sample.

13. The method of claim 8 wherein the detection of said nucleic acid indicates an alteration of the expression pattern of said nucleic acid in response to an external stimulus.

14. The method of claim 7 wherein the detecting is performed with single- or multiple-photon microscopy, time-resolved fluorescence microscopy or fluorescence endoscopy.

15. The compound according to claim 1, having the structure:

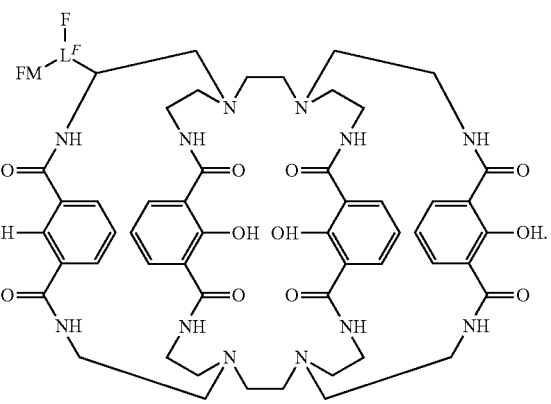

16. The compound according to claim 15, having the structure:

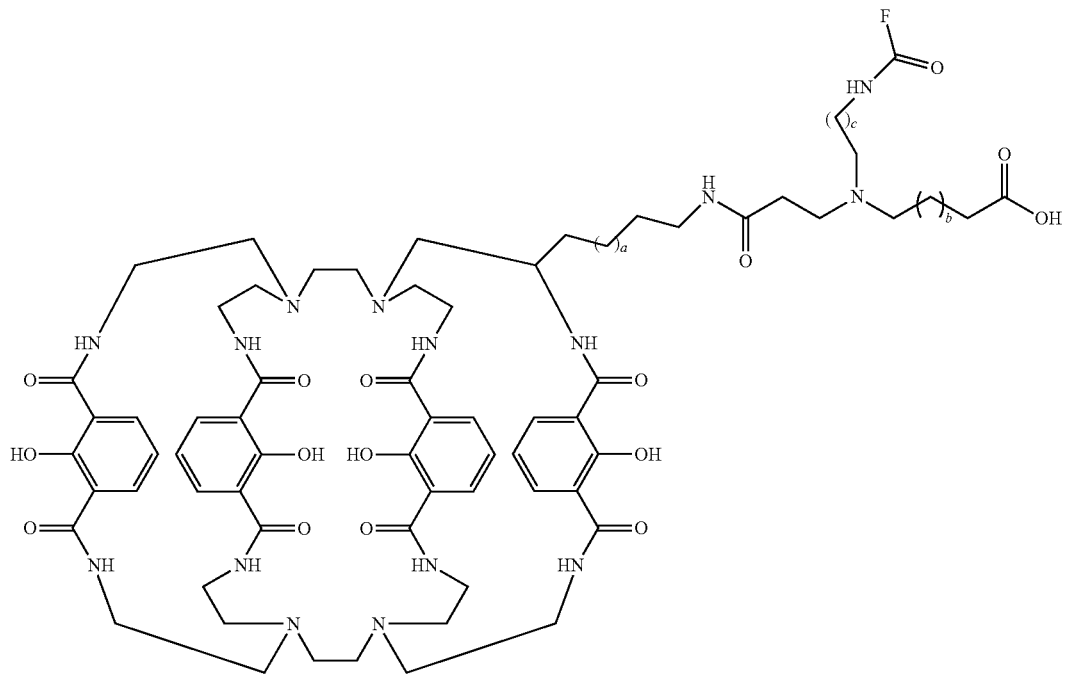

wherein a, b, and c are integers independently selected from 0 to 15.

17. The compound according to claim 16, having the structure:

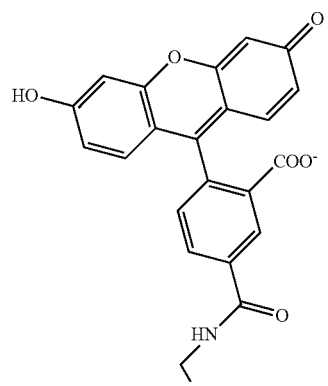

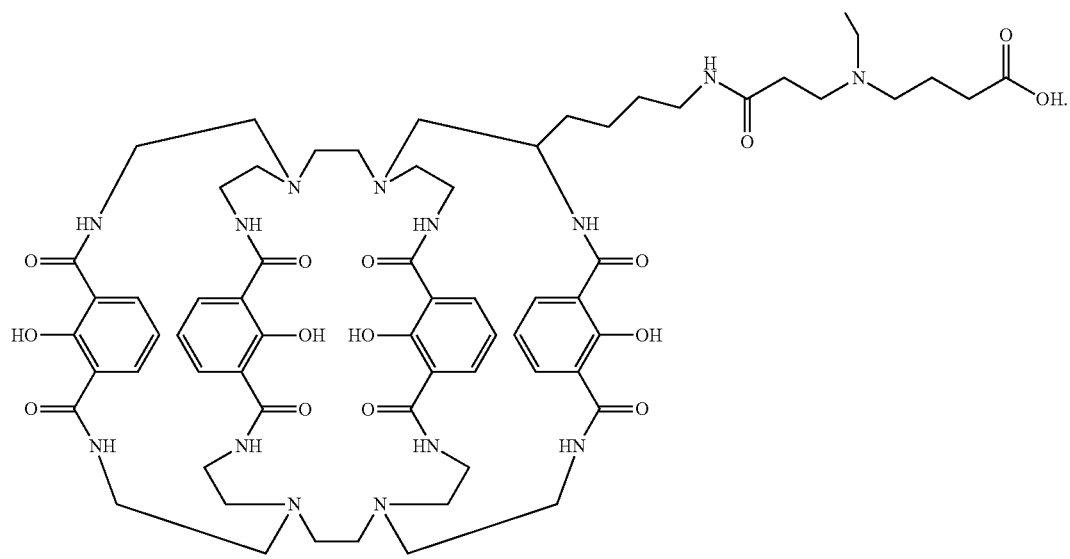

18. The compound according to claim 1, wherein the functional moiety is attached to a carrier moiety.

19. The compound according to claim 18, wherein said carrier moiety is a member selected from a nucleic acid, peptide, antibody, antibody fragment, antigen, receptor, lectin, saccharide and lipid.

20. The compound according to claim 1, having the structure:

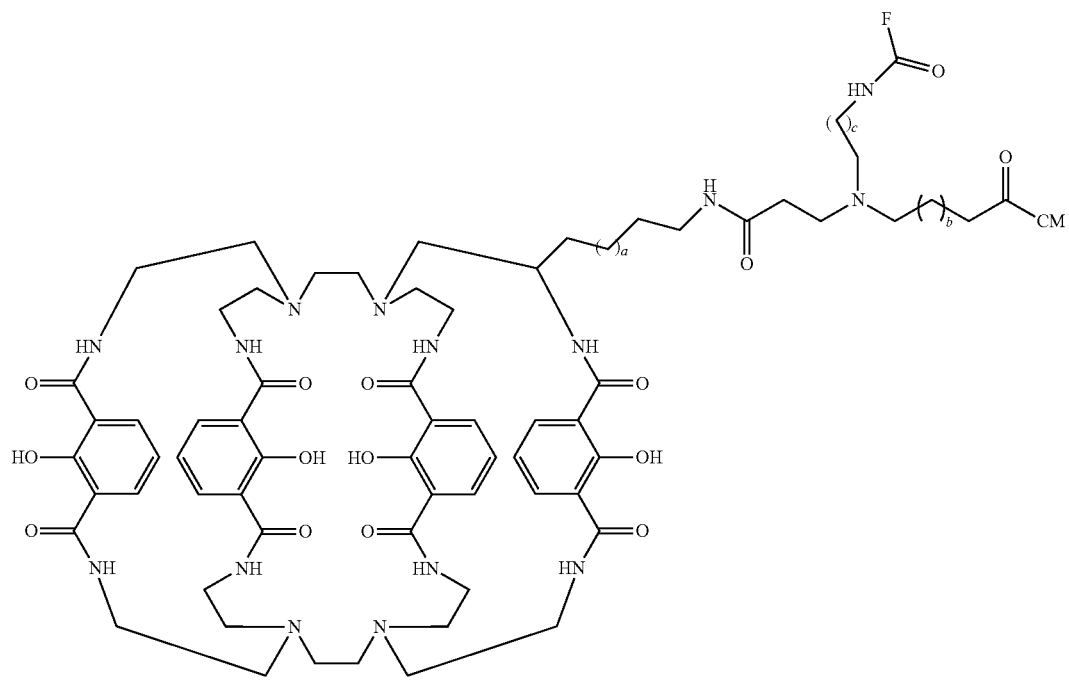

wherein a, b, and c are integers independently selected from 0 to 15; and

CM is said carrier moiety or solid support.

21. The complex according to claim 6, wherein said lanthanide is terbium (Tb).

22. A complex formed between a lanthanide ion and a compound according to claim 15.

23. The complex according to claim 22, wherein said lanthanide is a member selected from terbium (Tb), samarium (Sm), dysprosium (Dy), and europium (Eu).

24. The complex according to claim 23, wherein said lanthanide is terbium (Tb).

25. A mixture comprising at least two complexes according to claim 4, wherein the fluorophore of each complex is different; and each fluorophore is excited by a separate emission band of the complex formed between the moiety the fluorophore is attached to and the at least one metal ion.

* * * * *